(12) United States Patent
Andino et al.

(10) Patent No.: US 11,596,545 B2
(45) Date of Patent: Mar. 7, 2023

(54) SYSTEMS AND METHODS FOR OCULAR DRUG DELIVERY

(71) Applicant: CLEARSIDE BIOMEDICAL, INC., Alpharetta, GA (US)

(72) Inventors: Rafael Victor Andino, Grayson, GA (US); Thomas Edward Godfrey, Suwanee, GA (US); Shelley Eckert Hancock, Atlanta, GA (US); Samirkumar Patel, Atlanta, GA (US); Keleigh Jo Mahn, Southeast Atlanta, GA (US); Jesse Yoo, Snellville, GA (US); Vladimir Zarnitsyn, Atlanta, GA (US)

(73) Assignee: CLEARSIDE BIOMEDICAL, INC., Alpharetta, GA (US)

( * ) Notice: Subject to any disclaimer, the term of this patent is extended or adjusted under 35 U.S.C. 154(b) by 304 days.

(21) Appl. No.: 16/178,162

(22) Filed: Nov. 1, 2018

(65) Prior Publication Data

US 2019/0307606 A1 Oct. 10, 2019

Related U.S. Application Data

(63) Continuation of application No. PCT/US2017/030609, filed on May 2, 2017.
(Continued)

(51) Int. Cl.
*A61F 9/00* (2006.01)
*A61K 9/00* (2006.01)
(Continued)

(52) U.S. Cl.
CPC .......... *A61F 9/0017* (2013.01); *A61K 9/0051* (2013.01); *A61N 1/0428* (2013.01);
(Continued)

(58) Field of Classification Search
CPC ........ A61F 9/0008; A61F 9/0017; A61F 9/00; A61F 9/00781; A61F 2009/00865;
(Continued)

(56) References Cited

U.S. PATENT DOCUMENTS

| 2,187,259 A | 1/1940 | Barnhart |
| 2,841,145 A | 7/1958 | Epps |

(Continued)

FOREIGN PATENT DOCUMENTS

| CA | 2639322 | 3/2009 |
| CN | 1229679 A | 9/1999 |

(Continued)

OTHER PUBLICATIONS

How Does Iontophoresis Work?, HOMECEU, 2018 (Year: 2018).*
(Continued)

*Primary Examiner* — Bradley J Osinski
(74) *Attorney, Agent, or Firm* — Cooley LLP

(57) ABSTRACT

Devices, methods, and kits for ocular drug delivery are described herein. An apparatus can include a housing, an energy storage member, a barrel, and a hub. The housing contains the energy storage member. A proximal end portion of the barrel is coupled to a distal end portion of the housing. The barrel is configured to contain medicament and includes at least a portion of a piston and an elastomeric member. The piston is configured to move the elastomeric member within the barrel in response to a force produced by the energy storage member. The hub is coupled to a distal end portion of the barrel. An inner surface of the hub defines a nozzle through which the medicament flows when the elastomeric member moves within the barrel. The nozzle and the energy storage member are collectively configured to produce a fluid jet to access a target location within an eye.

32 Claims, 29 Drawing Sheets

Related U.S. Application Data

(60) Provisional application No. 62/378,401, filed on Aug. 23, 2016, provisional application No. 62/359,752, filed on Jul. 8, 2016, provisional application No. 62/341,149, filed on May 25, 2016, provisional application No. 62/330,501, filed on May 2, 2016.

(51) Int. Cl.
   *A61N 1/04* (2006.01)
   *A61N 1/30* (2006.01)
   *A61N 1/32* (2006.01)
   *A61F 9/007* (2006.01)
   *A61K 9/10* (2006.01)

(52) U.S. Cl.
   CPC .............. *A61N 1/30* (2013.01); *A61N 1/325* (2013.01); *A61F 9/00781* (2013.01); *A61K 9/0021* (2013.01); *A61K 9/10* (2013.01)

(58) Field of Classification Search
   CPC ........ A61F 2009/00868; A61N 1/0428; A61N 1/30; A61N 1/00; A61N 1/0444; A61N 1/0448; A61N 1/303; A61N 1/306; A61N 1/325; A61N 1/3603; A61N 1/36031; A61N 1/36046; A61K 9/0021; A61K 9/0051; A61M 5/30
   See application file for complete search history.

(56) References Cited

U.S. PATENT DOCUMENTS

| | | | |
|---|---|---|---|
| 2,939,459 | A | 6/1960 | Lazarte et al. |
| 3,376,999 | A | 4/1968 | De Hart et al. |
| 3,477,432 | A | 11/1969 | Shaw |
| 3,739,947 | A | 6/1973 | Baumann et al. |
| 3,762,540 | A | 10/1973 | Baumann et al. |
| 3,788,320 | A | 1/1974 | Dye |
| 3,838,690 | A | 10/1974 | Friedman |
| 3,892,311 | A | 7/1975 | Sneider |
| 3,962,430 | A | 6/1976 | O'Neill |
| 3,964,482 | A | 6/1976 | Gerstel et al. |
| 4,226,328 | A | 10/1980 | Beddow |
| 4,377,897 | A | 3/1983 | Eichenbaum et al. |
| 4,383,530 | A | 5/1983 | Bruno |
| 4,417,887 | A | 11/1983 | Koshi |
| 4,432,964 | A | 2/1984 | Shell et al. |
| 4,501,363 | A | 2/1985 | Isbey, Jr. |
| 4,525,346 | A | 6/1985 | Stark |
| 4,564,016 | A | 1/1986 | Maurice et al. |
| 4,601,708 | A | 7/1986 | Jordan |
| 4,615,331 | A | 10/1986 | Kramann |
| 4,689,040 | A | 8/1987 | Thompson |
| 4,708,147 | A | 11/1987 | Haaga |
| 4,717,383 | A | 1/1988 | Phillips et al. |
| 4,736,850 | A | 4/1988 | Bowman et al. |
| 4,755,169 | A | 7/1988 | Sarnoff et al. |
| 4,795,432 | A | 1/1989 | Karczmer |
| 4,804,371 | A | 2/1989 | Vaillancourt |
| 4,826,490 | A | 5/1989 | Byrne et al. |
| 4,826,871 | A | 5/1989 | Gressel et al. |
| 4,889,529 | A | 12/1989 | Haindl |
| 4,941,874 | A | 7/1990 | Sandow et al. |
| 4,966,773 | A | 10/1990 | Gressel et al. |
| 5,015,240 | A | 5/1991 | Soprani et al. |
| 5,023,087 | A | 6/1991 | Yau-Young |
| 5,024,662 | A | 6/1991 | Menes et al. |
| 5,025,811 | A | 6/1991 | Dobrogowski et al. |
| 5,057,072 | A * | 10/1991 | Phipps ................ A61N 1/0436 604/20 |
| 5,066,276 | A | 11/1991 | Wang |
| 5,098,389 | A | 3/1992 | Cappucci |
| 5,137,447 | A | 8/1992 | Hunter |
| 5,164,188 | A | 11/1992 | Wong |
| 5,172,807 | A | 12/1992 | Dragan et al. |
| 5,181,909 | A | 1/1993 | McFarlane |
| 5,206,267 | A | 4/1993 | Shulman |
| 5,273,530 | A | 12/1993 | del Cerro et al. |
| 5,279,564 | A | 1/1994 | Taylor |
| 5,295,972 | A | 3/1994 | Mischenko |
| 5,300,084 | A | 4/1994 | Johnson |
| 5,312,361 | A | 5/1994 | Zadini et al. |
| 5,320,609 | A | 6/1994 | Haber et al. |
| 5,354,286 | A | 10/1994 | Mesa et al. |
| 5,358,489 | A | 10/1994 | Wyrick |
| 5,364,373 | A | 11/1994 | Waskonig et al. |
| 5,364,374 | A | 11/1994 | Morrison et al. |
| 5,364,734 | A | 11/1994 | Morrison et al. |
| 5,395,310 | A * | 3/1995 | Untereker ............ A61N 1/0448 604/20 |
| 5,397,313 | A | 3/1995 | Gross |
| 5,399,159 | A | 3/1995 | Chin et al. |
| 5,407,070 | A | 4/1995 | Bascos et al. |
| 5,409,457 | A | 4/1995 | del Cerro et al. |
| 5,443,505 | A | 8/1995 | Wong et al. |
| 5,538,503 | A | 7/1996 | Henley et al. |
| 5,547,467 | A | 8/1996 | Pliquett et al. |
| 5,575,780 | A | 11/1996 | Saito |
| 5,632,740 | A | 5/1997 | Koch et al. |
| 5,658,256 | A | 8/1997 | Shields |
| D383,049 | S | 9/1997 | Concari et al. |
| 5,667,491 | A | 9/1997 | Pliquett et al. |
| 5,681,825 | A | 10/1997 | Lindqvist et al. |
| 5,752,942 | A | 5/1998 | Doyle et al. |
| 5,766,198 | A | 6/1998 | Li |
| 5,766,242 | A | 6/1998 | Wong et al. |
| 5,767,079 | A | 6/1998 | Glaser et al. |
| 5,779,668 | A | 7/1998 | Grabenkort |
| 5,788,679 | A | 8/1998 | Gravlee, Jr. |
| 5,792,099 | A | 8/1998 | DeCamp et al. |
| 5,817,075 | A | 10/1998 | Giungo |
| 5,824,072 | A | 10/1998 | Wong |
| 5,911,223 | A | 6/1999 | Weaver et al. |
| 5,919,158 | A | 7/1999 | Saperstein et al. |
| 5,952,378 | A | 9/1999 | Stjernschantz et al. |
| 5,968,022 | A | 10/1999 | Saito |
| 6,059,111 | A | 5/2000 | Davilla et al. |
| 6,083,199 | A | 7/2000 | Thorley et al. |
| 6,143,329 | A | 11/2000 | Kim |
| 6,154,671 | A | 11/2000 | Parel et al. |
| 6,159,218 | A | 12/2000 | Aramant et al. |
| 6,280,470 | B1 | 8/2001 | Peyman |
| 6,299,603 | B1 | 10/2001 | Hecker et al. |
| 6,309,347 | B1 | 10/2001 | Takahashi et al. |
| 6,309,374 | B1 | 10/2001 | Hecker et al. |
| 6,319,225 | B1 | 11/2001 | Sugita et al. |
| 6,319,240 | B1 | 11/2001 | Beck |
| 6,334,856 | B1 | 1/2002 | Allen et al. |
| 6,378,526 | B1 | 4/2002 | Bowman et al. |
| 6,387,078 | B1 | 5/2002 | Gillespie, III |
| 6,397,849 | B1 | 6/2002 | Bowman et al. |
| 6,413,245 | B1 | 7/2002 | Yaacobi et al. |
| 6,432,090 | B1 | 8/2002 | Brunel |
| 6,494,865 | B1 | 12/2002 | Alchas |
| 6,503,231 | B1 | 1/2003 | Prausnitz et al. |
| 6,517,523 | B1 | 2/2003 | Kaneko et al. |
| 6,524,581 | B1 | 2/2003 | Adamis |
| 6,530,904 | B1 | 3/2003 | Edwards et al. |
| 6,540,725 | B1 | 4/2003 | Ponzi |
| 6,546,283 | B1 | 4/2003 | Beck et al. |
| 6,551,299 | B2 | 4/2003 | Miyoshi et al. |
| 6,558,361 | B1 | 5/2003 | Yeshurun |
| 6,564,630 | B1 * | 5/2003 | Klemp .................. G01F 23/266 73/290 R |
| 6,569,123 | B2 | 5/2003 | Alchas et al. |
| 6,611,707 | B1 | 8/2003 | Prausnitz et al. |
| 6,622,864 | B1 | 9/2003 | Debbs et al. |
| 6,738,526 | B1 | 5/2004 | Betrisey et al. |
| 6,743,211 | B1 | 6/2004 | Prausnitz et al. |
| 6,773,916 | B1 | 8/2004 | Thiel et al. |
| D499,153 | S | 11/2004 | Kuo |
| 6,883,222 | B2 | 4/2005 | Landau |
| 6,918,889 | B1 | 7/2005 | Brunel |
| 6,929,623 | B2 | 8/2005 | Stone |

(56) References Cited

U.S. PATENT DOCUMENTS

| | | |
|---|---|---|
| 6,936,053 B1 | 8/2005 | Weiss |
| 6,979,316 B1 | 12/2005 | Rubin et al. |
| 7,025,774 B2 | 4/2006 | Freeman et al. |
| 7,150,735 B2 | 12/2006 | Hickle |
| 7,207,965 B2 | 4/2007 | Simon |
| 7,207,980 B2 | 4/2007 | Christian et al. |
| 7,211,062 B2 | 5/2007 | Kwon |
| 7,214,212 B2 | 5/2007 | Pommereau et al. |
| 7,226,439 B2 | 6/2007 | Prausnitz et al. |
| 7,316,676 B2 | 1/2008 | Peyman et al. |
| 7,425,207 B2 | 9/2008 | Miller et al. |
| 7,435,237 B2 | 10/2008 | Tan |
| 7,468,057 B2 | 12/2008 | Ponzi |
| 7,488,308 B2 | 2/2009 | Lesch, Jr. |
| D590,690 S | 4/2009 | Bertini |
| D598,543 S | 8/2009 | Vogel et al. |
| 7,569,035 B1 | 8/2009 | Wilmot et al. |
| 7,615,041 B2 | 11/2009 | Sullivan et al. |
| 7,648,482 B2 | 1/2010 | Edwards et al. |
| 7,678,077 B2 | 3/2010 | Harris et al. |
| 7,678,078 B1 | 3/2010 | Peyman et al. |
| 7,722,581 B2 | 5/2010 | Peyman |
| 7,914,803 B2 | 3/2011 | Chowhan et al. |
| 7,918,814 B2 | 4/2011 | Prausnitz et al. |
| 7,918,874 B2 | 4/2011 | Siegal |
| 7,947,660 B2 | 5/2011 | Clark et al. |
| 7,967,772 B2 | 6/2011 | McKenzie et al. |
| 8,003,124 B2 | 8/2011 | Varner et al. |
| 8,009,162 B2 * | 8/2011 | Takatori .............. G01K 1/14 257/467 |
| 8,034,105 B2 | 10/2011 | Stegmann et al. |
| 8,099,162 B2 * | 1/2012 | Roy .................. A61F 9/0017 604/521 |
| 8,114,110 B2 | 2/2012 | Bednarek et al. |
| 8,123,729 B2 | 2/2012 | Yamamoto et al. |
| 8,128,960 B2 | 3/2012 | Kabra et al. |
| 8,137,312 B2 | 3/2012 | Sundar et al. |
| 8,172,830 B2 | 5/2012 | Christian et al. |
| 8,173,617 B2 | 5/2012 | Clark et al. |
| 8,192,408 B2 | 6/2012 | Nazzaro et al. |
| 8,197,435 B2 * | 6/2012 | Prausnitz ............ A61P 27/02 604/19 |
| 8,197,443 B2 | 6/2012 | Sundar et al. |
| 8,221,353 B2 | 7/2012 | Cormier et al. |
| 8,235,967 B2 | 8/2012 | Chevallier et al. |
| D667,111 S | 9/2012 | Robinson |
| 8,287,494 B2 | 10/2012 | Ma |
| 8,303,599 B2 | 11/2012 | Hess et al. |
| D672,506 S | 12/2012 | Szymanski |
| 8,323,227 B2 | 12/2012 | Hamatake et al. |
| 8,328,772 B2 | 12/2012 | Kinast et al. |
| 8,337,421 B2 | 12/2012 | Freeman et al. |
| 8,337,509 B2 | 12/2012 | Schieber et al. |
| 8,348,924 B2 | 1/2013 | Christian et al. |
| 8,403,941 B2 | 3/2013 | Peterson et al. |
| 8,425,473 B2 | 4/2013 | Ho et al. |
| 8,430,862 B2 | 4/2013 | Peyman et al. |
| 8,448,786 B2 | 5/2013 | Tomes et al. |
| 8,460,242 B2 | 6/2013 | Paques et al. |
| 8,506,515 B2 | 8/2013 | Burns et al. |
| 8,529,492 B2 | 9/2013 | Clauson et al. |
| 8,535,333 B2 | 9/2013 | de Juan, Jr. et al. |
| 8,545,430 B2 | 10/2013 | Silvestrini |
| 8,545,554 B2 | 10/2013 | Novakovic et al. |
| 8,562,545 B2 | 10/2013 | Freeman et al. |
| 8,571,802 B2 | 10/2013 | Robinson et al. |
| 8,574,214 B2 | 11/2013 | Kuhn et al. |
| 8,574,217 B2 | 11/2013 | Peyman |
| 8,602,959 B1 | 12/2013 | Park et al. |
| 8,617,121 B2 | 12/2013 | Lanin et al. |
| 8,632,589 B2 | 1/2014 | Helmy |
| 8,636,713 B2 | 1/2014 | Prausnitz et al. |
| 8,652,118 B2 | 2/2014 | Peyman |
| 8,663,167 B2 | 3/2014 | Bartha |
| 8,663,303 B2 | 3/2014 | Horvath et al. |
| 8,668,676 B2 | 3/2014 | Chang |
| 8,685,435 B2 | 4/2014 | Nivaggioli et al. |
| 8,702,659 B2 | 4/2014 | Lanin et al. |
| 8,727,117 B2 | 5/2014 | Maasarani |
| 8,747,365 B2 | 6/2014 | De Sausmarez Lintell |
| 8,795,226 B2 | 8/2014 | Kuhn et al. |
| 8,808,225 B2 | 8/2014 | Prausnitz et al. |
| 8,808,242 B2 | 8/2014 | Paques et al. |
| D713,958 S | 9/2014 | Srinivasan et al. |
| 8,821,870 B2 | 9/2014 | Robinson et al. |
| D715,125 S | 10/2014 | Hung |
| 8,852,137 B2 | 10/2014 | Horvath et al. |
| 8,864,740 B2 | 10/2014 | Schabbach et al. |
| D718,602 S | 12/2014 | Musser |
| D719,256 S | 12/2014 | Ohashi |
| 8,920,375 B2 | 12/2014 | Gonnelli |
| D726,908 S | 4/2015 | Yu et al. |
| D733,289 S | 6/2015 | Blanchard et al. |
| D740,098 S | 10/2015 | Kuo et al. |
| 9,180,044 B2 * | 11/2015 | Touchard .............. A61F 9/0008 |
| 9,180,047 B2 | 11/2015 | Andino et al. |
| D750,223 S | 2/2016 | Andino et al. |
| 9,539,139 B2 | 1/2017 | Andino et al. |
| 9,572,800 B2 | 2/2017 | Zarnitsyn et al. |
| 9,636,253 B1 | 5/2017 | Andino et al. |
| 9,636,332 B2 | 5/2017 | Zarnitsyn et al. |
| 9,664,926 B2 | 5/2017 | Mitsui |
| 9,770,361 B2 | 9/2017 | Andino et al. |
| 9,788,995 B2 | 10/2017 | Prausnitz et al. |
| 9,931,330 B2 | 4/2018 | Zarnitsyn et al. |
| 9,937,075 B2 | 4/2018 | Andino et al. |
| 9,956,114 B2 | 5/2018 | Andino et al. |
| 10,188,550 B2 | 1/2019 | Andino et al. |
| 10,390,901 B2 | 8/2019 | Godfrey et al. |
| 10,517,756 B2 | 12/2019 | Andino et al. |
| 10,555,833 B2 | 2/2020 | Andino et al. |
| 10,632,013 B2 | 4/2020 | Prausnitz et al. |
| 10,722,396 B2 | 7/2020 | Andino et al. |
| 10,952,894 B2 | 3/2021 | Hammack et al. |
| 10,973,681 B2 | 4/2021 | Andino et al. |
| 2001/0008961 A1 | 7/2001 | Hecker et al. |
| 2001/0051798 A1 | 12/2001 | Hochman |
| 2002/0042594 A1 | 4/2002 | Lum et al. |
| 2002/0052580 A1 | 5/2002 | Ooyauchi |
| 2002/0082527 A1 | 6/2002 | Liu et al. |
| 2002/0082543 A1 | 6/2002 | Park et al. |
| 2002/0108875 A1 | 8/2002 | Feinberg et al. |
| 2002/0112981 A1 | 8/2002 | Cooper et al. |
| 2002/0142459 A1 | 10/2002 | Williams et al. |
| 2002/0156413 A1 | 10/2002 | Williams et al. |
| 2003/0009113 A1 | 1/2003 | Olson |
| 2003/0050602 A1 | 3/2003 | Pettis et al. |
| 2003/0083645 A1 | 5/2003 | Angel et al. |
| 2003/0088204 A1 * | 5/2003 | Joshi .................. A61N 1/0428 604/20 |
| 2003/0139729 A1 | 7/2003 | Stegmann et al. |
| 2003/0171722 A1 | 9/2003 | Paques et al. |
| 2003/0233070 A1 | 12/2003 | De La Serna et al. |
| 2004/0019331 A1 | 1/2004 | Yeshurun |
| 2004/0039253 A1 | 2/2004 | Peyman et al. |
| 2004/0049150 A1 | 3/2004 | Dalton et al. |
| 2004/0059256 A1 | 3/2004 | Perez |
| 2004/0072105 A1 | 4/2004 | Yeshurun et al. |
| 2004/0106904 A1 | 6/2004 | Gonnelli et al. |
| 2004/0122359 A1 | 6/2004 | Wenz et al. |
| 2004/0141925 A1 | 7/2004 | Bosch et al. |
| 2004/0164454 A1 | 8/2004 | Gartstein et al. |
| 2004/0186084 A1 | 9/2004 | Alam et al. |
| 2004/0199130 A1 | 10/2004 | Chornenky et al. |
| 2004/0215347 A1 | 10/2004 | Hayes |
| 2004/0249404 A1 | 12/2004 | Haefliger |
| 2004/0265365 A1 | 12/2004 | Daddona et al. |
| 2005/0009910 A1 | 1/2005 | Hughes et al. |
| 2005/0033230 A1 | 2/2005 | Alchas et al. |
| 2005/0055083 A1 | 3/2005 | Carranza et al. |
| 2005/0065137 A1 | 3/2005 | Jani et al. |
| 2005/0070819 A1 | 3/2005 | Poux et al. |
| 2005/0089545 A1 | 4/2005 | Kuwano et al. |
| 2005/0101582 A1 | 5/2005 | Lyons et al. |

(56) References Cited

U.S. PATENT DOCUMENTS

| | | |
|---|---|---|
| 2005/0101882 A1 | 5/2005 | Leira et al. |
| 2005/0101967 A1 | 5/2005 | Weber et al. |
| 2005/0137525 A1 | 6/2005 | Wang et al. |
| 2005/0148034 A1 | 7/2005 | Hariri et al. |
| 2005/0171507 A1 | 8/2005 | Christian et al. |
| 2005/0181017 A1 | 8/2005 | Hughes et al. |
| 2005/0203575 A1 | 9/2005 | Carson et al. |
| 2005/0209565 A1 | 9/2005 | Yuzhakov et al. |
| 2005/0244462 A1 | 11/2005 | Farooq |
| 2005/0244463 A1 | 11/2005 | Huang et al. |
| 2005/0244469 A1 | 11/2005 | Whitcup et al. |
| 2005/0245906 A1 | 11/2005 | Makower et al. |
| 2005/0256499 A1 | 11/2005 | Pettis et al. |
| 2005/0281862 A1 | 12/2005 | Karakelle et al. |
| 2006/0013859 A1 | 1/2006 | Yamada et al. |
| 2006/0032768 A1 | 2/2006 | Hamai et al. |
| 2006/0036318 A1 | 2/2006 | Foulkes |
| 2006/0055090 A1 | 3/2006 | Lee et al. |
| 2006/0084942 A1 | 4/2006 | Kim et al. |
| 2006/0086689 A1 | 4/2006 | Raju |
| 2006/0089607 A1 | 4/2006 | Chen |
| 2006/0141049 A1 | 6/2006 | Lyons et al. |
| 2006/0173418 A1 | 8/2006 | Rinaudo et al. |
| 2006/0178614 A1 | 8/2006 | Nemati |
| 2006/0189608 A1 | 8/2006 | Bingaman |
| 2006/0195187 A1 | 8/2006 | Stegmann et al. |
| 2006/0202385 A1 | 9/2006 | Xu et al. |
| 2006/0229562 A1 | 10/2006 | Marsh et al. |
| 2006/0233858 A1 | 10/2006 | Tzekov et al. |
| 2006/0259008 A1 | 11/2006 | Orilla |
| 2006/0271025 A1 | 11/2006 | Jones et al. |
| 2007/0016103 A1 | 1/2007 | Calasso et al. |
| 2007/0060927 A1 | 3/2007 | Longson et al. |
| 2007/0073197 A1 | 3/2007 | Prausnitz et al. |
| 2007/0082841 A1 | 4/2007 | Higuchi et al. |
| 2007/0093742 A1* | 4/2007 | Higuchi .................. A61N 1/306 604/20 |
| 2007/0093877 A1 | 4/2007 | Beecham et al. |
| 2008/7008284 | 4/2007 | Higuchi et al. |
| 2007/0149944 A1 | 6/2007 | Tashiro et al. |
| 2007/0151882 A1 | 7/2007 | Cocheteux et al. |
| 2007/0178197 A1 | 8/2007 | Larue et al. |
| 2007/0191863 A1 | 8/2007 | De Juan et al. |
| 2007/0202116 A1 | 8/2007 | Burnie et al. |
| 2007/0202186 A1 | 8/2007 | Yamamoto et al. |
| 2007/0224278 A1 | 9/2007 | Lyons et al. |
| 2007/0225654 A1 | 9/2007 | Hess et al. |
| 2007/0233037 A1 | 10/2007 | Gifford, III et al. |
| 2007/0260201 A1 | 11/2007 | Prausnitz et al. |
| 2007/0270745 A1 | 11/2007 | Nezhat et al. |
| 2007/0270768 A1 | 11/2007 | Dacquay et al. |
| 2007/0282405 A1 | 12/2007 | Wong et al. |
| 2007/0287985 A1 | 12/2007 | Estes et al. |
| 2007/0299386 A1 | 12/2007 | Peyman |
| 2008/0008762 A1 | 1/2008 | Robinson et al. |
| 2008/0027371 A1* | 1/2008 | Higuchi .................. A61K 31/56 604/20 |
| 2008/0033351 A1 | 2/2008 | Trogden et al. |
| 2008/0058704 A1 | 3/2008 | Hee et al. |
| 2008/0058717 A1 | 3/2008 | Spector |
| 2008/0065002 A1* | 3/2008 | Lobl .................. A61M 25/0068 604/21 |
| 2008/0071246 A1 | 3/2008 | Nazzaro et al. |
| 2008/0082841 A1 | 4/2008 | Juenemann et al. |
| 2008/0097335 A1 | 4/2008 | Trogden et al. |
| 2008/0097346 A1 | 4/2008 | Charles |
| 2008/0097390 A1 | 4/2008 | Dacquay et al. |
| 2008/0131484 A1 | 6/2008 | Robinson et al. |
| 2008/0152694 A1 | 6/2008 | Lobl et al. |
| 2008/0177239 A1 | 7/2008 | Li et al. |
| 2008/0183123 A1* | 7/2008 | Behar-Cohen .......... A61P 27/06 604/21 |
| 2008/0200883 A1 | 8/2008 | Tomono |
| 2008/0228127 A1 | 9/2008 | Burns et al. |
| 2008/0234625 A1 | 9/2008 | Dacquay et al. |
| 2009/0030381 A1 | 1/2009 | Lind et al. |
| 2009/0076463 A1 | 3/2009 | Attinger |
| 2009/0081277 A1 | 3/2009 | Robinson et al. |
| 2009/0082321 A1 | 3/2009 | Edelman et al. |
| 2009/0082713 A1* | 3/2009 | Friden .................. A61N 1/325 604/21 |
| 2009/0088721 A1 | 4/2009 | Bizemont et al. |
| 2009/0105749 A1 | 4/2009 | De Juan et al. |
| 2009/0148527 A1 | 6/2009 | Robinson |
| 2009/0187167 A1 | 7/2009 | Sexton et al. |
| 2009/0259180 A1 | 10/2009 | Choi |
| 2009/0287161 A1 | 11/2009 | Traub et al. |
| 2009/0312782 A1 | 12/2009 | Park |
| 2010/0010004 A1 | 1/2010 | Van emelen et al. |
| 2010/0010452 A1 | 1/2010 | Paques et al. |
| 2010/0012537 A1 | 1/2010 | Farrar et al. |
| 2010/0015158 A1 | 1/2010 | Robinson et al. |
| 2010/0057011 A1 | 3/2010 | Charles |
| 2010/0074957 A1 | 3/2010 | Robinson et al. |
| 2010/0098772 A1 | 4/2010 | Robinson et al. |
| 2010/0100054 A1 | 4/2010 | Cormier et al. |
| 2010/0152646 A1* | 6/2010 | Girijavallabhan .... A61F 9/0017 604/22 |
| 2010/0152667 A1 | 6/2010 | Kietzmann |
| 2010/0173866 A1 | 7/2010 | Hee et al. |
| 2010/0191176 A1 | 7/2010 | Ho et al. |
| 2010/0211079 A1 | 8/2010 | Aramant |
| 2010/0241102 A1 | 9/2010 | Ma |
| 2010/0256597 A1 | 10/2010 | Prausnitz et al. |
| 2010/0312120 A1 | 12/2010 | Meier |
| 2010/0318034 A1* | 12/2010 | Goncalves ............ A61F 9/0017 604/174 |
| 2011/0004265 A1 | 1/2011 | Wenger et al. |
| 2011/0060310 A1 | 3/2011 | Prestrelski et al. |
| 2011/0112546 A1 | 5/2011 | Juan, Jr. et al. |
| 2011/0166531 A1 | 7/2011 | Stroumpoulis et al. |
| 2011/0202012 A1 | 8/2011 | Bartlett |
| 2011/0213317 A1 | 9/2011 | Chen et al. |
| 2011/0238075 A1 | 9/2011 | Clauson et al. |
| 2011/0243999 A1 | 10/2011 | Dellamary et al. |
| 2011/0264028 A1* | 10/2011 | Ramdas ................ A61M 37/00 604/20 |
| 2011/0282298 A1 | 11/2011 | Agian et al. |
| 2011/0295152 A1 | 12/2011 | Sasaki et al. |
| 2011/0306923 A1 | 12/2011 | Roy |
| 2012/0004245 A1 | 1/2012 | May et al. |
| 2012/0008327 A1 | 1/2012 | Brennan et al. |
| 2012/0024987 A1 | 2/2012 | Nagele Nacken |
| 2012/0029360 A1 | 2/2012 | Hendriks et al. |
| 2012/0035524 A1 | 2/2012 | Silvestrini |
| 2012/0078224 A1 | 3/2012 | Lerner et al. |
| 2012/0083727 A1 | 4/2012 | Barnett |
| 2012/0095414 A1 | 4/2012 | Lanin et al. |
| 2012/0095438 A1 | 4/2012 | Lanin et al. |
| 2012/0101475 A1 | 4/2012 | Wilmot et al. |
| 2012/0116306 A1 | 5/2012 | Heald et al. |
| 2012/0123351 A1 | 5/2012 | Lanin et al. |
| 2012/0123386 A1 | 5/2012 | Tsals |
| 2012/0123437 A1 | 5/2012 | Horvath et al. |
| 2012/0123440 A1 | 5/2012 | Horvath et al. |
| 2012/0123473 A1 | 5/2012 | Hernandez |
| 2012/0130207 A1 | 5/2012 | O'dea et al. |
| 2012/0136318 A1 | 5/2012 | Lanin et al. |
| 2012/0150128 A1 | 6/2012 | Zhao |
| 2012/0157880 A1 | 6/2012 | Haselby et al. |
| 2012/0165723 A1 | 6/2012 | Horvath et al. |
| 2012/0191064 A1 | 7/2012 | Conston et al. |
| 2012/0197208 A1 | 8/2012 | Bruggemann et al. |
| 2012/0197218 A1 | 8/2012 | Timm |
| 2012/0220917 A1 | 8/2012 | Silvestrini et al. |
| 2012/0226260 A1 | 9/2012 | Prausnitz et al. |
| 2012/0232522 A1 | 9/2012 | Prausnitz et al. |
| 2012/0259288 A1 | 10/2012 | Wagner et al. |
| 2012/0265149 A1 | 10/2012 | Lerner et al. |
| 2012/0271272 A1 | 10/2012 | Hammack et al. |
| 2013/0035662 A1 | 2/2013 | Decker et al. |
| 2013/0040895 A1 | 2/2013 | Robinson et al. |
| 2013/0041265 A1 | 2/2013 | Sostek et al. |
| 2013/0060202 A1 | 3/2013 | Thorley et al. |

(56) References Cited

U.S. PATENT DOCUMENTS

| | | |
|---|---|---|
| 2013/0065888 A1 | 3/2013 | Cetina-Cizmek et al. |
| 2013/0072900 A1 | 3/2013 | Colantonio |
| 2013/0079716 A1 | 3/2013 | Thorley et al. |
| 2013/0096533 A1 | 4/2013 | Freeman et al. |
| 2013/0102973 A1 | 4/2013 | Thorley et al. |
| 2013/0116523 A1 | 5/2013 | Jung et al. |
| 2013/0138049 A1 | 5/2013 | Kemp et al. |
| 2013/0140208 A1 | 6/2013 | Hemmann |
| 2013/0150803 A1 | 6/2013 | Shetty et al. |
| 2013/0190694 A1 | 7/2013 | Barrow-Williams et al. |
| 2013/0211335 A1 | 8/2013 | Paques et al. |
| 2013/0216623 A1 | 8/2013 | Yamamoto et al. |
| 2013/0218102 A1 | 8/2013 | Iwase et al. |
| 2013/0218269 A1 | 8/2013 | Schachar et al. |
| 2013/0226103 A1 | 8/2013 | Papiorek |
| 2013/0237910 A1 | 9/2013 | Shetty et al. |
| 2013/0237916 A1 | 9/2013 | Hanson et al. |
| 2013/0245600 A1 | 9/2013 | Yamamoto et al. |
| 2013/0253416 A1 | 9/2013 | Rotenstreich |
| 2013/0289545 A1 | 10/2013 | Baerveldt et al. |
| 2013/0295006 A1 | 11/2013 | Christoforidis et al. |
| 2013/0331786 A1 | 12/2013 | Hofmann |
| 2013/0338612 A1 | 12/2013 | Smith et al. |
| 2014/0010823 A1 | 1/2014 | Robinson et al. |
| 2014/0012226 A1 | 1/2014 | Hochman |
| 2014/0018771 A1 | 1/2014 | Shekalim |
| 2014/0027326 A1 | 1/2014 | Peruzzo |
| 2014/0031833 A1 | 1/2014 | Novakovic et al. |
| 2014/0039391 A1 | 2/2014 | Clarke et al. |
| 2014/0039413 A1 | 2/2014 | Jugl et al. |
| 2014/0078854 A1 | 3/2014 | Head et al. |
| 2014/0088552 A1 | 3/2014 | Soni et al. |
| 2014/0094752 A1 | 4/2014 | Hiles |
| 2014/0102927 A1 | 4/2014 | Liversidge |
| 2014/0107566 A1 | 4/2014 | Prausnitz et al. |
| 2014/0114243 A1 | 4/2014 | Smith et al. |
| 2014/0135716 A1 | 5/2014 | Clarke et al. |
| 2014/0194834 A1 | 7/2014 | Passaglia et al. |
| 2014/0200518 A1 | 7/2014 | Ekman et al. |
| 2014/0224688 A1 | 8/2014 | Slemmen et al. |
| 2014/0231287 A1 | 8/2014 | Tomes et al. |
| 2014/0236098 A1 | 8/2014 | Mica et al. |
| 2014/0243754 A1 | 8/2014 | Clarke et al. |
| 2014/0249539 A1 | 9/2014 | Mica et al. |
| 2014/0257207 A1 | 9/2014 | Clarke et al. |
| 2014/0276482 A1 | 9/2014 | Astafieva et al. |
| 2014/0296802 A1 | 10/2014 | Geiger et al. |
| 2014/0309599 A1 | 10/2014 | Schaller |
| 2014/0323979 A1 | 10/2014 | Henley et al. |
| 2014/0323985 A1 | 10/2014 | Hourmand et al. |
| 2014/0330213 A1 | 11/2014 | Hourmand et al. |
| 2014/0350479 A1 | 11/2014 | Hourmand et al. |
| 2014/0353190 A1 | 12/2014 | Okihara et al. |
| 2015/0013827 A1 | 1/2015 | Kuhn |
| 2015/0013835 A1 | 1/2015 | Cordes |
| 2015/0025474 A1 | 1/2015 | Riedel et al. |
| 2015/0038905 A1* | 2/2015 | Andino .............. A61M 5/3293 604/117 |
| 2015/0045731 A1 | 2/2015 | Gupta et al. |
| 2015/0045744 A1 | 2/2015 | Gupta et al. |
| 2015/0051545 A1 | 2/2015 | Henderson et al. |
| 2015/0051581 A1 | 2/2015 | Andino et al. |
| 2015/0110717 A1 | 4/2015 | Distel et al. |
| 2015/0129456 A1 | 5/2015 | Miller et al. |
| 2015/0133415 A1 | 5/2015 | Whitcup |
| 2015/0157359 A1 | 6/2015 | Shinzato et al. |
| 2015/0209180 A1 | 7/2015 | Prausnitz et al. |
| 2015/0223977 A1 | 8/2015 | Oberkircher et al. |
| 2015/0258120 A1 | 9/2015 | Zarnitsyn et al. |
| 2015/0297609 A1 | 10/2015 | Shah et al. |
| 2015/0320596 A1 | 11/2015 | Gifford, III et al. |
| 2016/0015895 A1 | 1/2016 | Blondino et al. |
| 2016/0015908 A1 | 1/2016 | Uemura et al. |
| 2016/0022486 A1 | 1/2016 | Clauson et al. |
| 2016/0106584 A1 | 4/2016 | Andino et al. |
| 2016/0106587 A1 | 4/2016 | Jarrett et al. |
| 2016/0166819 A1 | 6/2016 | Simmers |
| 2016/0193080 A1 | 7/2016 | Hammack et al. |
| 2016/0199581 A1 | 7/2016 | Cachemaille et al. |
| 2016/0206628 A1 | 7/2016 | Zarnitsyn et al. |
| 2016/0213662 A1 | 7/2016 | Zarnitsyn et al. |
| 2016/0310417 A1 | 10/2016 | Prausnitz et al. |
| 2016/0331738 A1 | 11/2016 | Jarrett et al. |
| 2016/0354239 A1* | 12/2016 | Roy .................... A61N 1/30 |
| 2017/0086725 A1 | 3/2017 | Woo et al. |
| 2017/0095369 A1 | 4/2017 | Andino et al. |
| 2017/0216228 A1 | 8/2017 | Asgharian et al. |
| 2017/0224435 A1 | 8/2017 | Godfrey et al. |
| 2017/0224534 A1 | 8/2017 | Andino et al. |
| 2017/0273827 A1 | 9/2017 | Prausnitz et al. |
| 2017/0290702 A1 | 10/2017 | Yamamoto et al. |
| 2017/0333416 A1 | 11/2017 | Zarnitsyn et al. |
| 2017/0340560 A1 | 11/2017 | Yamamoto et al. |
| 2018/0028358 A1 | 2/2018 | Andino et al. |
| 2018/0028516 A1 | 2/2018 | Zarnitsyn et al. |
| 2018/0042765 A1 | 2/2018 | Noronha et al. |
| 2018/0042767 A1 | 2/2018 | Andino et al. |
| 2018/0092897 A1 | 4/2018 | Zarnitsyn et al. |
| 2018/0325884 A1 | 11/2018 | Zarnitsyn et al. |
| 2018/0333297 A1 | 11/2018 | Andino et al. |
| 2019/0000669 A1 | 1/2019 | Hammack et al. |
| 2019/0231592 A1 | 8/2019 | Andino et al. |
| 2019/0240208 A1 | 8/2019 | Zarnitsyn et al. |
| 2019/0269702 A1 | 9/2019 | White et al. |
| 2019/0290485 A1 | 9/2019 | Andino et al. |
| 2019/0350755 A1 | 11/2019 | Andino et al. |
| 2020/0030143 A1 | 1/2020 | Andino et al. |
| 2020/0061357 A1 | 2/2020 | Jung et al. |
| 2020/0237556 A1 | 7/2020 | Prausnitz et al. |
| 2020/0330269 A1 | 10/2020 | Bley et al. |
| 2020/0390692 A1 | 12/2020 | Yamamoto et al. |
| 2021/0022918 A1 | 1/2021 | Prausnitz et al. |
| 2021/0169689 A1 | 6/2021 | Bley et al. |
| 2021/0212940 A1 | 7/2021 | Yamamoto et al. |
| 2021/0220173 A1 | 7/2021 | Andino et al. |

FOREIGN PATENT DOCUMENTS

| | | |
|---|---|---|
| CN | 1604799 A | 4/2005 |
| CN | 1608587 A | 4/2005 |
| CN | 1681547 A | 10/2005 |
| CN | 1706365 | 12/2005 |
| CN | 1736474 | 2/2006 |
| CN | 1946445 A | 4/2007 |
| CN | 101052434 A | 10/2007 |
| CN | 101351239 A | 1/2009 |
| CN | 201192452 Y | 2/2009 |
| CN | 101559249 A | 10/2009 |
| CN | 201356711 Y | 12/2009 |
| CN | 201591741 U | 9/2010 |
| CN | 101854891 A | 10/2010 |
| CN | 101959519 A | 1/2011 |
| CN | 103037802 A | 4/2013 |
| CN | 103209733 A | 7/2013 |
| CN | 103857431 A | 6/2014 |
| CN | 204364577 U | 6/2015 |
| EA | 006961 | 6/2006 |
| EP | 1188456 | 3/2002 |
| EP | 1568359 | 8/2005 |
| EP | 2193821 | 6/2010 |
| EP | 2307055 | 4/2011 |
| JP | 2001-525826 | 12/2001 |
| JP | 2007-510744 | 4/2007 |
| JP | 2007-518804 | 7/2007 |
| JP | 2009-183441 | 8/2009 |
| JP | 2009-531298 | 9/2009 |
| JP | 2010-234034 | 10/2010 |
| JP | 2013-543418 | 12/2013 |
| JP | 5828535 B1 | 12/2015 |
| KR | 20040096561 A | 11/2004 |
| RU | 14351 U1 | 7/2000 |
| RU | 2344767 | 1/2009 |
| RU | 2353393 | 4/2009 |
| RU | 2428956 | 9/2011 |

(56) References Cited

FOREIGN PATENT DOCUMENTS

| | | |
|---|---|---|
| WO | WO 92/08406 | 5/1992 |
| WO | WO 92/20389 | 11/1992 |
| WO | WO 94/01124 | 1/1994 |
| WO | WO 94/12217 | 6/1994 |
| WO | WO 96/09838 | 4/1996 |
| WO | WO 98/51348 | 11/1998 |
| WO | WO 2000/007530 | 2/2000 |
| WO | WO 2000/007565 | 2/2000 |
| WO | WO 2001/041685 | 6/2001 |
| WO | WO 2002/058769 | 8/2002 |
| WO | WO 2003/002094 | 1/2003 |
| WO | WO 2003/024507 | 3/2003 |
| WO | WO 2003/039633 | 5/2003 |
| WO | WO-2004105864 A1 | 12/2004 |
| WO | WO 2005/011741 | 2/2005 |
| WO | WO 2005/032510 | 4/2005 |
| WO | WO 2005/046641 | 5/2005 |
| WO | WO 2005/069831 | 8/2005 |
| WO | WO 2005/072701 | 8/2005 |
| WO | WO 2005/074942 | 8/2005 |
| WO | WO 2005/107845 | 11/2005 |
| WO | WO 2006/004595 | 1/2006 |
| WO | WO 2006/042252 | 4/2006 |
| WO | WO 2006/058189 | 6/2006 |
| WO | WO 2006/128034 | 11/2006 |
| WO | WO 2006/138719 | 12/2006 |
| WO | WO 2007/069697 A1 | 6/2007 |
| WO | WO 2007/100745 | 9/2007 |
| WO | WO-2007099406 A2 | 9/2007 |
| WO | WO 2007/130105 | 11/2007 |
| WO | WO 2007/131050 | 11/2007 |
| WO | WO 2007/150018 | 12/2007 |
| WO | WO 2008/082637 | 7/2008 |
| WO | WO 2009/067325 | 5/2009 |
| WO | WO 2009/105534 | 8/2009 |
| WO | WO 2009/114521 | 9/2009 |
| WO | WO 2010/009034 | 1/2010 |
| WO | WO 2010/054660 | 5/2010 |
| WO | WO 2010/132751 | 11/2010 |
| WO | WO 2011/057065 | 5/2011 |
| WO | WO 2011/123722 | 10/2011 |
| WO | WO 2011/139713 | 11/2011 |
| WO | WO 2012/019136 | 2/2012 |
| WO | WO 2012/051575 | 4/2012 |
| WO | WO 2012/118498 | 9/2012 |
| WO | WO 2012/125869 | 9/2012 |
| WO | WO 2012/125872 | 9/2012 |
| WO | WO 2012/162459 | 11/2012 |
| WO | WO 2013/050236 | 4/2013 |
| WO | WO 2013/098166 | 7/2013 |
| WO | WO 2013/151904 | 10/2013 |
| WO | WO 2014/028285 | 2/2014 |
| WO | WO 2014/036009 | 3/2014 |
| WO | WO 2014/074823 | 5/2014 |
| WO | WO 2014/179698 | 11/2014 |
| WO | WO 2014/197317 | 12/2014 |
| WO | WO 2015/015467 | 2/2015 |
| WO | WO 2015/095772 | 6/2015 |
| WO | WO-2015110660 A1 | 7/2015 |
| WO | WO 2015/195842 | 12/2015 |
| WO | WO 2015/196085 | 12/2015 |
| WO | WO 2016/042162 | 3/2016 |
| WO | WO 2016/042163 | 3/2016 |
| WO | WO 2017/120600 | 7/2017 |
| WO | WO 2017/120601 | 7/2017 |
| WO | WO 2017/139375 | 8/2017 |
| WO | WO 2017/190142 | 11/2017 |
| WO | WO 2017/192565 | 11/2017 |

OTHER PUBLICATIONS

Examination Report No. 1 for Australian Application No. 2014259694, dated May 24, 2018, 2 pages.
First Office Action for Chinese Application No. 201480025034.4, dated Apr. 24, 2018, 10 pages.
Office Action for Eurasian Application No. 201592109, dated Apr. 1, 2016, 4 pages.
Office Action for Eurasian Application No. 201592109, dated Jan. 31, 2018, 2 pages.
Extended Search Report for European Application No. 14791646.4, dated Nov. 21, 2016, 6 pages.
Office Action for European Application No. 14791646.4, dated Dec. 4, 2017, 5 pages.
Office Action for European Application No. 14791646.4, dated Sep. 17, 2018, 5 pages.
Office Action for Israeli Application No. 242395, dated May 7, 2019, 7 pages.
Office Action for Mexican Application No. MX/a/2015/015282, dated May 15, 2019, 8 pages.
Notice of Reasons for Rejection for Japanese Application No. 2016-512068, dated Mar. 26, 2018, 4 pages.
Office Action for New Zealand Application No. 714172, dated Feb. 1, 2018, 4 pages.
Office Action for New Zealand Application No. 714172, dated Jul. 24, 2018, 4 pages.
Office Action for New Zealand Application No. 714172, dated Dec. 12, 2018, 3 pages.
Search Report and Written Opinion for Singapore Application No. 11201509051V, dated Nov. 2, 2016, 6 pages.
Examination Report for Singapore Application No. 11201509051V, dated Feb. 1, 2017, 4 pages.
International Search Report and Written Opinion for International Application No. PCT/US2014/036590, dated Dec. 10, 2014, 10 pages.
Office Action for U.S. Appl. No. 14/268,687, dated May 19, 2016, 6 pages.
Partial European Search Report for European Application No. 18176172.7, dated Oct. 30, 2018, 13 pages.
Extended European Search Report for European Application No. 18176172.7, dated Feb. 6, 2019, 11 pages.
Notice of Reasons for Rejection for Japanese Application No. 2018-142345, dated Jun. 6, 2019, 6 pages.
Office Action for U.S. Appl. No. 14/523,243, dated Feb. 27, 2015, 14 pages.
Office Action for U.S. Appl. No. 15/946,838, dated Jun. 27, 2019, 7 pages.
Office Action for U.S. Appl. No. 16/381,213, dated May 31, 2019, 7 pages.
Partial Supplementary European Search Report for European Application No. 15810459.6, dated Dec. 22, 2017, 13 pages.
Extended European Search Report for European Application No. 15810459.6, dated Apr. 16, 2018, 11 pages.
Notice of Reasons for Rejection for Japanese Application No. 2016-574090, dated Mar. 4, 2019, 18 pages.
Office Action for Russian Application No. 2017101660, dated Mar. 5, 2019, 7 pages.
Office Action for U.S. Appl. No. 15/383,582, dated May 5, 2017, 10 pages.
International Search Report and Written Opinion for International Application No. PCT/US2015/036715, dated Jan. 19, 2016, 9 pages.
International Search Report and Written Opinion for International Application No. PCT/US2017/030609, dated Oct. 6, 2017, 12 pages.
International Search Report and Written Opinion for International Application No. PCT/US2017/065796, dated Apr. 12, 2018, dated Apr. 12, 2018, 9 pages.
International Search Report and Written Opinion for International Application No. PCT/US2017/046553, dated Dec. 13, 2017, 14 pages.
Abbott Laboratories Inc., Abbott Park, Illinois, USA, Abbott Medical Optics, "HEALON5 OVD," 2004, [online]. Retrieved from the Interent: <URL: http://abbottmedicaloptics.com/products/cataract/ovds/healon5-viscoelastic>. Retrieved from the Internet on: Aug. 16, 2016, 5 pages.
Anthem, USA, "Medical Policy. Suprachoroidal Injection of a Pharmacologic Agent," Last Review Date: Nov. 14, 2013, [online].

(56) References Cited

OTHER PUBLICATIONS

Retrieved from the Internet: <URL: http://www.anthem.com/medicalpolicies/policies/mp_pw_b076412.htm>. Retrieved from the Internet on: Oct. 24, 2014, American Medical Association, 3 pages.
Berglin, L. C. et al., "Tracing of Suprachoroidally Microneedle Injected Labled Drugs and Microbeads in Human, Pig and Rabbit Tissue Using Liquid Nitrogen Snap-Freeze Thaw and Lypholization Techniques," Invest Ophthalmol Vis Sci., 51:E-Abstract 5330 (2010), 2 pages.
Careforde Inc., Careforde Healthcare, Chicago, IL, "B Braun Glass Loss-Of-Resistance Syringes #332155—5cc Glass Loss-Of-Resistance Syringe, Luer Lock Metal Tip, 10/cs," [online]. Retrieved from the Internet: <http://careforde.com/b-braun-glass-loss-of-resistance-syringes-332155-5cc-glass-loss-of-resistance-syringe-luer-lock-metal-tip-10-cs/>. Retrieved from the Interneton: Oct. 16, 2014, (2014), 2 pages.
Careforde Healthcare, B Braun Glass Loss-Of-Resistance Syringes # 332158—10cc Glass Loss-Of-Resistance Syringe, Luer Slip Metal Tip, 10/cs, (2014), 2 pages.
Careforde Inc., Careforde Healthcare, Chicago, IL, "B Braun Perifix Plastic Loss-Of-Resistance Syringes # 332152—8cc Plastic Luer Lock Loss-of-Resistance Syringe, 50/cs," [online]. Retrieved from the Internet: <http://careforde.com/b-braun-perifix-plastic-loss-of-resistance-syringes-332152-8cc-plastic-luer-lock-loss-of-resistance-syringe-50-cs/>. Retrieved from the Internet on: Oct. 16, 2014, (2014), 2 pages.
Cho, S. W. et al., "Drug delivery to the suprachoroidal space," Chap. 12 in: Ocular Drug Delivery Systems: Barriers and Application of Nanoparticulate Systems, Thassu, D. et al. (eds.), CRC Press, pp. 235-258 (2012).
Doncaster and Bassetlaw Hospitals, NHS Foundation Trust, Department of Ophthalmology, "Intravitreal injection of triamcinolone," Jul. 2010, [online]. Retrieved from the Internet: <URL: http://www.dbh.nhs.uk/Library/Patient_Information_Leaflets/WPR32110%20IIT%20No%20crops.pdf>, 2 pages.
Edwards, A. et al., "Fiber matrix model of sclera and corneal stroma for drug delivery to the eye," AIChE Journal, 44(1):214-225 (1998).
Einmahl, S. et al., "Evaluation of a novel biomaterial in the suprachoroidal space of the rabbit eye," Invest. Ophthalmol. Vis. Sci., 43(5):1533-1539 (2002).
Einmahl, S. et al., "Ocular biocompatibility of a poly(ortho ester) characterized by autocatalyzed degradation," J. Biomed. Mater. Res., 67(1):44-53 (2003).
"Epidural," Wikipedia [online], retrieved from the internet on Sep. 3, 2014, <URL: http:/en.wikipedia.org/wiki/Epidural>, 21 pages.
Falkenstein, I. A. et al., "Comparison of visual acuity in macular degeneration patients measured with Snellen and Early Treatment Diabetic Retinopathy study charts," Ophthalmology 115(2):319-323 (Feb. 2008).
Feldkamp, L. A. et al., "Practical cone-beam algorithm," J. Opt. Soc. Am. A, 1(6):612-619 (1984).
Furrer, P. et al., "Ocular tolerance of preservatives and alternatives," European Journal of Pharmaceutics and Biopharmaceutics, 53(3):263-280 (2002).
Geroski, D. H. et al., "Drug delivery for posterior segment eye disease," Invest. Ophthalmol. Vis. Sci., 41(5):961-964 (2000).
Gilger, B. C. et al., "Treatment of acute posterior uveitis in a porcine model by injection of triamcinolone acetonide into the suprachoroidal space using microneedles," Investigative Ophthalmology & Visual Science, 54(4):2483-2492 (2013).
Gilger, et al., "A Novel Bioerodible Deep Scleral Lamellar Cyclosporine Implant for Uveitis," Invest Ophthalmol Vis Sci, vol. 47, Issue 6, 2006, pp. 2596-2605.
Hanekamp, S. et al., "Inhibition of Corneal and Retinal Angiogenesis by Organic Integrin Antagonists After Intrascleral or Intravitreal Drug Delivery," Invest Ophthalmol Vis Sci., 43: E-Abstract 3710, ARVO (2002), 2 pages.
Heller, J., Ocular delivery using poly(ortho esters), Adv. Drug. Deliv. Rev., 57(14):2053-2062 (2005).
Haller, J. A., "Intraocular Steroids in the Office. New formulations offer preservative-free triamcinolone without relying on compounding pharmacies," Retinal Physician [online]. Retrieved from the Internet: <URL: https://www.retinalphysician.com/supplements/2009/february-2009/special-edition/intraocular-steroids-in-the-office>, Feb. 1, 2009, 4 pages.
Haller, J. A. et al., "Evaluation of the safety and performance of an applicator for a novel intravitreal dexamethasone drug delivery system for the treatment of macular edema," Retina, 29(1):46-51 (2009).
Hogan et al., Chapter Eight, Choroid, In Histology of the Human Eye, 9 pages (1971).
Jain, A., "Pseudo loss of resistance in epidural space localization: A complication of subcutaneous emphysema or simply a faulty technique," Saudi J. Anaseth, 5(1):108-109 (2011) (Abstract).
Jiang, J. et al., "Measurement and Prediction of Lateral Diffusion within Human Sclera," Investigative Ophthalmology & Visual Science, 47(7):3011-3016 (2006).
Jiang, J. et al., "Coated Microneedles for Drug Delivery to the Eye," Investigative Ophthalmology & Visual Science, 48(9):4038-4043 (2007).
Jiang, J. et al., "Intrascleral drug delivery to the eye using hollow microneedles," Pharmaceutical Research, 26(2):395-403 (2009).
Kadam, R. S. et al., "Suprachoroidal delivery in a rabbit ex vivo eye model: influence of drug properties, regional differences in delivery, and comparison with intravitreal and intracameral routes," Molecular Vision, 19:1198-1210 (May 2013).
Karim, R. et al., "Interventions for the treatment of uveitic macular edema: a systematic review and meta-analysis," Clinical Ophthalmology, 7:1109-1144 (2013).
Lee, S-B et al., "Drug delivery through the sclera: effects of thickness, hydration and sustained release systems," Experimental Eye Research, 78:599-607 (2004).
Lee et al., "Thixotropic property in pharmaceutical formulations," Journal of Controlled Release (2009) 136:88-98.
Lindfield, D. et al., "Suprachoroidal Devices in Glaucoma. The Past, Present, and Future of Surgery for Suprachoroidal Drainage," Cataract & Refractive Surgery Today Europe, [online], Oct. 2013, Retrieved from the Internet: <URL: http://bmctoday.net/crstodayeurope/2013/10/article.asp?f=suprachoroidal-devices-in-glaucoma>. Retrieved from the Internet on: Oct. 24, 2014, Bryn Mawr Communications LLC, Wayne, PA, USA, 3 pages.
Loewen, N., "The suprachoroidal space in glaucoma surgery," Jul. 2012, 4 pages.
Maurice, D., "Review: Practical Issues in Intravitreal Drug Delivery," J. Ocul. Pharmacol. Ther., 17(4):393-401 (2001).
McAllister, D. V. et al., "Microfabricated needles for transdermal delivery of macromolecules and nanoparticles: Fabrication methods and transport studies," Proc. Nat'l Acad. Sci USA, 100(24):13755-13760 (2003).
Norman, D., Epidural analgesia using loss of resistance with air versus saline: Does it make a difference? Should we reevaluate our practice?, AANA Journal, 71(6):449-453 (Dec. 2003).
Olsen, T. W. et al., "Cannulation of the Suprachoroidal Space: A Novel Drug Delivery Methodology to the Posterior Segment," American J. Opthamology, 142(5):777-787 (2006).
Olsen, T., "Drug Delivery to the Suprachoroidal Space Shows Promise," Retina Today, pp. 36-39 (Mar./Apr. 2007).
Ozkiris, A., "Intravitreal Triamcinolone Acetonide Injection for the Treatment of Posterior Uveitis," Ocular Immunology and Inflammation, vol. 14, Issue 4, pp. 233-238 (May 2006), Published online: Jul. 8, 2009 (Abstract).
Patel, S. R. et al., "Targeted administration into the suprachoroidal space using a microneedle for drug delivery to the posterior segment of the eye," Investigative Ophthalmology & Visual Science, 53(8):4433-4441 (Jul. 2012).
Patel, S. et al., "Suprachoroidal Drug Delivery Using Microneedles," Invest. Ophthalmol. Vis. Sci., 49:E-Abstract 5006 (2008), 2 pages.
Patel, S. et al., "Drug Binding to Sclera," Invest Ophthalmol Vis Sci., 50:E-Abstract 5968 (2009), 2 pages.
Patel, S. R. et al., "Intraocular Pharmacokinetics of Suprachoroidal Drug Delivery Administered Using Hollow Microneedles," Invest Ophthalmol Vis Sci., 51:E-Abstract 3796 (2010), 2 pages.

(56) References Cited

OTHER PUBLICATIONS

Patel, S. R. et al., "Suprachoroidal drug delivery to the back of the eye using hollow microneedles," Pharmaceutical Research, 28(1):166-176 (2011). Published online: Sep. 21, 2010.
Penkov, M. A. et al., "A ten-year experience with usage of the method of supra-choroidal administration of medicinal substances," Oftalmol. Zh., 35(5):281-285 (1980) (Translated from Russian).
Prausnitz, M. R. et al., "Permeability of cornea, sclera and conjunctiva: A literature analysis for drug delivery to the eye," Journal of Pharmaceutical Sciences, 87(12):1479-1488 (1998).
Prausnitz, M. R. et al., "Measurement and prediction of transient transport across sclera for drug delivery to the eye," Industrial and Engineering Chemistry Research, 37(8):2903-2907 (1998).
Prausnitz, M. R., "Microneedles for Ocular Drug Delivery," Review of Olsen, T., Drug Delivery to the Suprachoroidal Space Shows Promise, Retina Today, Mar./Apr. 2007, p. 39.
Rowe-Rendleman, C. L. et al., "Prophylactic Intra-Scleral Injection of Steroid Compounds in Rabbit Model of Retinal Neovascularization," Invest Ophthalmol Vis. Sci.,43:E-Abstract 3872, ARVO (2002), 2 pages.
Saberski, L. R. et al., "Identification of the epidural space: Is loss of resistance to air a safe technique? A review of the complications related to the use of air," Regional Anesthesia, 22(1):3-15 (1997).
Sallam, A. et al., "Repeat intravitreal triamcinolone acetonide injections in uveitic macular oedema," Acta Ophthalmologica, 90(4):e323-e325 (2012).
Scott, I. U. et al., "Baseline characteristics and response to treatment of participants with hemiretinal compared with branch retinal or central retinal vein occlusion in the standard care vs. corticosteroid for retinal vein occlusion (SCORE)," Arch. Ophthalmol., 130(12):1517-1524 (Dec. 2012).
Shuler, R. K. et al., "Scleral Permeability of a Small, Single-Stranded Oligonucleotide," Journal of Ocular Pharmacology and Therapeutics, 20(2):159-168 (2004) (Abstract).
Wang, P. M. et al., "Minimally Invasive Extraction of Dermal Interstitial Fluid for Glucose Monitoring Using Microneedles," Diabetes Technology & Therapeutics, 7(1):131-141 (2005).
You, X. D. et al., "Chitosan drug delivery system implanting into suprachoroidal space for perforating ocular injury in rabbits," International Journal of Ophthalmology, 5(1):74-76 (2005) [English Abstract].
Office Action for U.S. Appl. No. 16/591,067, dated Nov. 18, 2019, 7 pages.
International Search Report and Written Opinion for International Application No. PCT/US2018/030688, dated Aug. 8, 2018, 22 pages.
Keraliya, R. A. et al., "Osmotic Drug Delivery System as a Part of Modified Release Dosage Form," ISRN Pharmaceuticals, 2012, vol. 2012, Article ID 528079. doi: 10.5402/2012/528079. Epub Jul. 17, 2012, 9 pages.
Office Action for U.S. Appl. No. 15/619,065, dated Nov. 27, 2020, 23 pages.
Office Action for Korean Application No. 10-2015-7034411, dated Nov. 16, 2020, 8 pages.
First Office Action for Chinese Application No. 201910430078.X, dated Feb. 1, 2021, 8 pages.
Office Action for European Application No. 18199418.7, dated Nov. 10, 2020, 5 pages.
First Office Action for Chinese Application No. 201780062253.3, dated Dec. 25, 2020, 22 pages.
Office Action for U.S. Appl. No. 11/743,535, dated Aug. 19, 2010, 7 pages.
Office Action for U.S. Appl. No. 11/743,535, dated Dec. 29, 2009, 6 pages.
International Search Report and Written Opinion for International Application No. PCT/US2007/068055, dated Nov. 7, 2007, 13 pages.
Office Action for Canadian Application No. 2797258, dated Nov. 21, 2016, 3 pages.
Extended European Search Report for European Application No. 11777924.9, dated Feb. 4, 2015, 7 pages.
Office Action for European Application No. 11777924.9, dated Oct. 1, 2019, 5 pages.
Office Action for Indian Application No. 10099/DELNP/2012, dated Jul. 2, 2019, 5 pages.
Office Action for Russian Application No. 2012147341, dated Feb. 26, 2015, 8 pages.
Office Action for U.S. Appl. No. 12/767,768, dated Jun. 10, 2011, 5 pages.
International Search Report and Written Opinion for International Application No. PCT/US2011/033987, dated Feb. 14, 2012, 7 pages.
Examination Report No. 1 for Australian Application No. 2015230874, dated Jul. 28, 2017, 11 pages.
Office Action for Japanese Application No. 2016-068174, dated Mar. 1, 2017, 8 pages.
Office Action for U.S. Appl. No. 13/447,246, dated Oct. 28, 2013, 5 pages.
Office Action for U.S. Appl. No. 13/453,407, dated Mar. 20, 2013, 5 pages.
Office Action for U.S. Appl. No. 14/136,657, dated Dec. 16, 2016, 7 pages.
Office Action for U.S. Appl. No. 15/708,779, dated Jul. 15, 2019, 8 pages.
Office Action for U.S. Appl. No. 16/826,443, dated Jun. 1, 2020, 6 pages.
Office Action for Canadian Application No. 2,882,184, dated May 1, 2019, 3 pages.
Office Action for Canadian Application No. 2,882,184, dated Jan. 24, 2020, 6 pages.
Office Action for Canadian Application No. 2,882,184, dated Aug. 18, 2020, 3 pages.
Extended Search Report for European Application No. 13833318.2, dated Apr. 1, 2016, 7 pages.
Office Action for European Application No. 13833318.2, dated Aug. 26, 2020, 5 pages.
Office Action for U.S. Appl. No. 14/424,685, dated Jun. 10, 2016, 10 pages.
Office Action for U.S. Appl. No. 14/424,685, dated Dec. 12, 2016, 15 pages.
International Search Report and Written Opinion for International Application No. PCT/US2013/056863, dated Nov. 26, 2013, 8 pages.
Office Action for U.S. Appl. No. 15/619,065, dated Jun. 13, 2019, 30 pages.
Office Action for U.S. Appl. No. 15/619,065, dated Jan. 28, 2020, 24 pages.
Preliminary Office Action for Brazilian Application No. 112015027762-4, dated Jan. 17, 2020, 6 pages.
Office Action for Canadian Application No. 2,911,290, dated Jun. 18, 2020, 5 pages.
Office Action for European Application No. 14791646.4, dated Feb. 11, 2020, 5 pages.
Office Action for Israeli Application No. 242395, dated Aug. 10, 2020, 12 pages.
Office Action for European Application No. 18176172.7, dated Feb. 7, 2020, 4 pages.
Office Action for Brazilian Application No. PI 0708133-2, dated Feb. 26, 2019, 11 pages.
Office Action for Chinese Application No. 200780014501.3, dated Mar. 11, 2010, 6 pages.
Office Action for Chinese Application No. 200780014501.3, dated Aug. 26, 2010, 10 pages.
Office Action for European Application No. 07751620.1, dated Sep. 13, 2013, 7 pages.
Extended European Search Report for European Application No. 07751620.1, dated Jan. 15, 2013, 10 pages.
Office Action for European Application No. 07751620.1, dated Dec. 11, 2014, 5 pages.
Invitation pursuant to Article 94(3) and Rule 71(1) for European Application No. 07751620.1, dated Feb. 29, 2016, 3 pages.

(56) References Cited

OTHER PUBLICATIONS

Summons to Attend Oral Proceedings Pursuant to Rule 115(1) EPC for European Application No. 07751620.1, dated Jun. 13, 2017, 8 pages.
Office Action for Japanese Application No. 2008-556462, dated Jul. 24, 2012, 15 pages.
Office Action for Indian Application No. 3345/KOLNP/2008, dated May 21, 2015, 3 pages.
Office Action for Singapore Application No. 200805936-2, dated Oct. 15, 2012, 7 pages.
Search Report and Written Opinion for Singapore Application No. 200805936-2, dated Jun. 8, 2010, 13 pages.
Supplementary Search Report for Singapore Application No. 200805936-2, dated May 6, 2011, 8 pages.
Supplementary Search Report for Singapore Application No. 200805936-2, dated May 26, 2011, 8 pages.
Office Action for U.S. Appl. No. 11/709,941, dated Jun. 24, 2014, 11 pages.
Office Action for U.S. Appl. No. 11/709,941, dated Mar. 23, 2011, 9 pages.
Office Action for U.S. Appl. No. 11/709,941, dated Feb. 11, 2015, 14 pages.
Office Action for U.S. Appl. No. 11/709,941, dated Oct. 27, 2011, 8 pages.
Office Action for U.S. Appl. No. 11/709,941, dated Apr. 12, 2016, 25 pages.
Office Action for U.S. Appl. No. 11/709,941, dated Dec. 27, 2016, 28 pages.
Office Action for U.S. Appl. No. 11/709,941, dated Jan. 16, 2018, 32 pages.
Office Action for U.S. Appl. No. 11/709,941, dated Dec. 14, 2018, 17 pages.
International Search Report and Written Opinion for International Application No. PCT/US2007/004874, dated Jun. 4, 2008, 6 pages.
Office Action for Chinese Application No. 201110093644.6, dated Mar. 26, 2012, 11 pages.
Office Action for Chinese Application No. 201110093644.6, dated Sep. 7, 2012, 8 pages.
Office Action for Chinese Application No. 201110093644.6, dated Dec. 14, 2012, 3 pages.
Extended European Search Report for European Application No. 18176149.5, dated Jan. 22, 2019, 11 pages.
Office Action for U.S. Appl. No. 13/842,218, dated Jul. 5, 2016, 11 pages.
Office Action for U.S. Appl. No. 13/842,288, dated Oct. 6, 2015, 10 pages.
Office Action for U.S. Appl. No. 15/398,538, dated Jul. 20, 2018, 12 pages.
Office Action for U.S. Appl. No. 15/398,538, dated Apr. 16, 2019, 8 pages.
First Office Action for Chinese Application No. 201180060268.9, dated Oct. 10, 2014, 9 pages.
Second Office Action for Chinese Application No. 201180060268.9, dated Jun. 18, 2015, 4 pages.
Third Office Action for Chinese Application No. 201180060268.9, dated Feb. 5, 2016, 6 pages.
Examination Report for European Application No. 11776049.6, dated Oct. 25, 2016, 4 pages.
Office Action for Japanese Application No. 2013-534049, dated Sep. 1, 2015, 11 pages.
Office Action for U.S. Appl. No. 13/273,775, dated Feb. 12, 2015, 13 pages.
Office Action for U.S. Appl. No. 13/273,775, dated Jul. 3, 2014, 12 pages.
International Search Report and Written Opinion for International Application No. PCT/US2011/056433, dated Apr. 25, 2012, 17 pages.
Office Action for Chinese Application No. 201510144330.2, dated Apr. 5, 2016, 17 pages.
Second Office Action for Chinese Application No. 201510144330.2, dated Dec. 20, 2016, 13 pages.
Third Office Action for Chinese Application No. 201510144330.2, dated Jun. 28, 2017, 3 pages.
Extended European Search Report for European Application No. 18199418.7, dated Jul. 5, 2019, 9 pages.
Office Action for U.S. Appl. No. 14/821,310, dated Jul. 14, 2017, 11 pages.
First Office Action for Chinese Application No. 201610805842.3, dated Jul. 21, 2017, 4 pages.
Office Action for U.S. Appl. No. 15/872,206, dated May 1, 2020, 8 pages.
Office Action for U.S. Appl. No. 15/872,206, dated Oct. 19, 2020, 9 pages.
Extended European Search Report for European Application No. 17880800.2, dated Jun. 2, 2020, 13 pages.
Office Action for U.S. Appl. No. 15/675,035, dated Jun. 11, 2020, 14 pages.
Beer, P. J. et al., "Photographic Evidence of Vitreous Wicks After Intravitreal Injections," Retina Today, 2(2):24-39 (Mar. 2007).
Choy, Y. B. et al., "Mucoadhesive microdiscs engineered for ophthalmic drug delivery: effect of particle geometry and fomulation on preocular residence time," Investigative Ophthalmology & Visual Science, 49:4808-4815 (2008).
Dinning, W. J., "Steroids and the eye-indications and complications," Postgraduate Medical Journal, vol. 52, 1976, pp. 634-638.
Examination Report for Indian Application No. 201917009102, dated Jul. 16, 2021, 6 pages.
First Examination Report for Indian Application No. 10270/DELNP/2015, dated Apr. 5, 2021, 7 pages.
Notice of Reasons for Rejection for Japanese 2018-557826, dated Mar. 29, 2021, 13 pages.
Office Action for European Application No. 13833318.2, dated Apr. 20, 2021, 4 pages.
Office Action for European Application No. 17755007.6, dated Jun. 25, 2021, 6 pages.
Office Action for U.S. Appl. No. 15/619,065, dated Jun. 11, 2021, 18 pages.
Office Action for U.S. Appl. No. 17/217,455, dated Jun. 23, 2021, 13 pages.
Preliminary Office Action for Brazilian Application No. 112012027416-3, dated Jul. 11, 2021, 2 pages.
Second Office Action for Chinese Application No. 201910430078.X, dated Aug. 18, 2021, 5 pages.

* cited by examiner

SYSTEMS AND METHODS FOR OCULAR DRUG DELIVERY

CROSS-REFERENCE TO RELATED APPLICATIONS

This application is a continuation of International Patent Application PCT/US2017/030609, filed May 2, 2017, entitled "Systems and Methods for Ocular Drug Delivery," which claims priority to and the benefit of U.S. Provisional Patent Application Ser. No. 62/330,501, entitled "Systems and Methods for Defining Drug Delivery Pathways in Bodily Tissues," filed May 2, 2016; U.S. Provisional Patent Application Ser. No. 62/341,149, entitled "Systems and Methods for Delivering Drugs Using Electronic Fields," filed May 25, 2016; U.S. Provisional Patent Application Ser. No. 62/359,752, entitled "Systems and Methods for Ocular Drug Delivery," filed Jul. 8, 2016; and U.S. Provisional Patent Application Ser. No. 62/378,401, entitled "Systems and Methods for Preparing Bodily Tissue for Drug Delivery," filed Aug. 23, 2016, each of the disclosures of which is incorporated herein by reference in its entirety.

BACKGROUND

The embodiments described herein relate generally to the field of drug delivery and more particularly to systems, devices, methods, and kits for targeted delivery of a substance into ocular tissues for treatment of the eye.

The anterior region of the eye refers to the front portion of the eye (i.e., the portion of the eye in front of, and including, the lens), and includes structures in front of the vitreous humour such as the cornea, iris, ciliary body and lens. The posterior region of the eye refers to the back portion of the eye (i.e., the portion of the eye behind the lens), and includes the vitreous humor, retina, choroid, and optic nerve. The sclera (a.k.a., the white of the eye) is an opaque, fibrous, protective outer layer of the eye. The sclera includes connective tissue that maintains the shape of the eye by offering resistance to internal and external forces. The suprachoroidal space is the area between the sclera and choroid in the posterior region of the eye. Many inflammatory and proliferative diseases in the posterior region of the eye require long-term pharmaceutical treatment.

Although there are known methods of delivery of substances (e.g., drugs) into the posterior region of the eye, there is a need for improved devices and methods. It is often difficult to deliver effective doses of a drug to the back of the eye using conventional delivery methods such as topical application, intravitreal administration (IVT), or systemic administration. For example, topical applications, such as eye drops, are useful in treating conditions affecting the exterior surface of the eye or tissues at the front of the eye, however, eye drops are often not sufficiently conveyed to the back of the eye, as may be required for treatment of some retinal diseases such as macular degeneration, diabetic retinopathy, uveitis, and the like. Moreover, there is a short drug-eye contact time using eye drops, which can lead to more frequent applications of the drug. Other topical applications, such as ointments, allow a prolonged drug-eye contact time, thus requiring less frequent applications, but the application process increases the possibility of contamination since the drug is often applied via a person's hand. Furthermore, drugs that are administered via topical application are hindered from reaching the posterior region of the eye by components of the anterior region of the eye, as well as physiologic processes such as tears, blinking, drug metabolism, and drug binding.

Some known methods of treatment employ intravitreal (IVT) administration. IVT administration can include multiple injections due to the limited half-life of many compounds in the vitreous, potentially causing trauma and increase the risk of cataract, retinal detachment, hemorrhage and endophthalmitis.

The delivery of drugs to the posterior region of the eye through systemic administration is limited by the outer and inner blood-retinal barriers. Moreover, other limitations for systemic application of drugs include potentially reduced time of therapeutic effects and potency due to the dilution and degradation of the drug before reaching the target tissue. Thus, systemic administration usually requires an increase in the quantity of drugs necessary to achieve therapeutic concentrations at the target tissue, which increases the risk of adverse effects due to the accumulation of the drug in other tissues throughout the body.

Although injection is used for transdermal and intraocular drug delivery, there remains a need for improved injection systems, devices, kits, and methods, particularly for targeted delivery of substances (e.g., drugs) into the posterior region of the eye. For example, in certain situations, direct injection of a medicament into the eye (e.g., into the vitreous) using conventional 27 gauge or 30 gauge needles and syringes can be effective. Direct injection, however, can be associated with significant safety risks, and physicians often require professional training to effectively perform such methods. Such risks include, for example, controlling the needle depth and placement to deliver the medicament to the desired location (e.g., the suprachoroidal space (SCS) of the eye or the subretinal space (SRS) of the eye), infection, retinal detachment, and vitreous hemorrhage. In some instances, targeted injection of a therapeutic agent is desirable. In such instances, however, the relatively small anatomic structures of the eye often result in significant challenges to placing a needle at a target location using known devices and methods, especially as they pertain to placing the distal end of the needle at the desired depth within the eye.

In addition, many known methods of direct injection of a drug into the eye include inserting a needle or a cannula at an acute angle relative to a surface of the eye, which can make controlling the depth of insertion challenging. For example, some such methods include controlling the angular orientation of the needle such that the injected substance exits the needle at a particular location. Moreover, some known methods of injecting substances into ocular tissue include using complicated visualization system to control the placement of the needle or cannula.

Needle insertion and injection can be further complicated in procedures where, due to the small needle size and/or the characteristics of the injected drug, delivery involves the use of force levels higher than that which users are comfortable with applying. For example, some studies have shown that users (e.g., medical practitioners) generally do not like to apply more than 2 N force against the eye during ocular injection. Accordingly, in certain situations a user may not properly deliver the medicament using known systems and methods because of their reluctance to apply the force to fully expel the medicament.

Moreover, some known systems do not provide a convenient way to prevent leakage from an insertion site, which can lead to discomfort and loss of medicament. For example, intraocular injection can lead to leakage of intraocular fluids (e.g., aqueous and vitreous humour) or the medicament from a delivery passageway formed by the needle penetrating into the ocular tissue. If the medicament is delivered to the sclera instead of the target ocular tissue layer, for example, the SCS and/or the SRS, the high backpressure of the sclera can force the medicament to leak from the insertion site. This can prolong treatment as well as increase costs associated with treatment.

Moreover, injection into different target layers of the eye can cause variability in the amount of the force required for insertion of the needle and/or injection of the medicament. Different layers of the eye can have different densities. For example, the sclera generally has a higher density than the conjunctiva, the SCS, or the SRS. Differences in the density of the target region or layer can produce different backpressure against the needle exit, i.e., the top of the needle from which the fluid emerges. Thus, injection into a relatively dense ocular material such as the sclera requires more motive pressure to expel the medicament from the needle than is required when injecting a medicament into the SCS or the SRS.

Thus, a need exists for improved systems, devices, methods, and kits for localized or targeted delivery of drugs/compounds to treat infections and diseases affecting the eye (e.g., the posterior region of the eye).

SUMMARY

Devices, methods, and kits for ocular drug delivery are described herein. In some embodiments, an apparatus includes a housing, an energy storage member, a barrel, and a hub. The housing has a proximal end portion and a distal end portion, and contains the energy storage member. The barrel has a proximal end portion and a distal end portion. The proximal end portion of the barrel is coupled to the distal end portion of the housing. The barrel is configured to contain a medicament and includes at least a portion of a piston and an elastomeric member. The piston is configured to move the elastomeric member within the barrel in response to a force produced by the energy storage member when the energy storage member is actuated. The hub is coupled to the distal end portion of the barrel, and includes an inner surface and an outer surface. The inner surface of the hub defines a nozzle through which the medicament flows when the elastomeric member moves within the barrel. The nozzle and the energy storage member are collectively configured to produce a fluid jet to access a target location within an eye when the energy storage member is actuated. The outer surface of the hub forms a fluid-tight seal with a surface of the eye.

DETAILED DESCRIPTION

Figure 1:
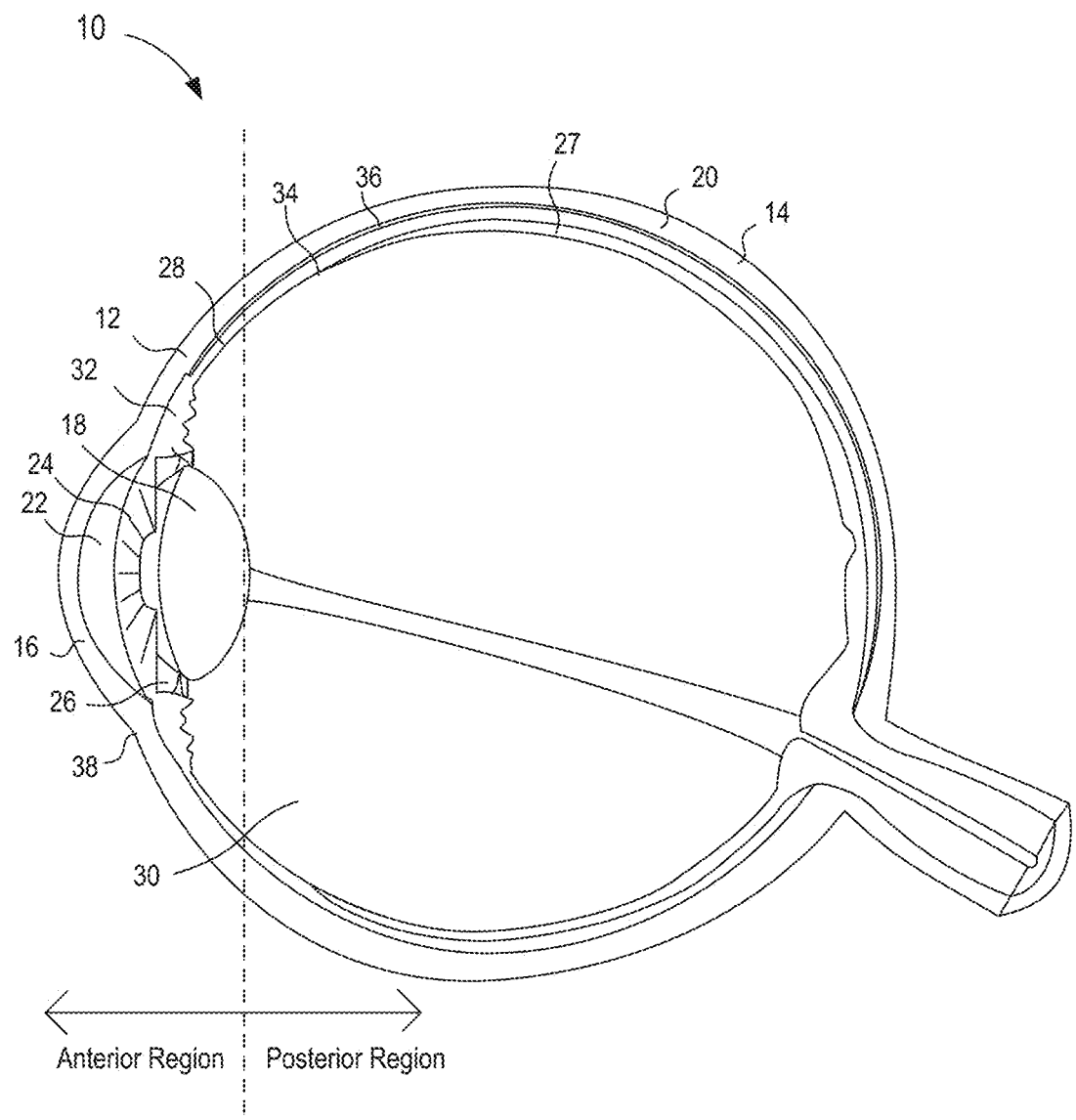
FIG. 1 is a cross-sectional view of an illustration of the human eye.

Devices, methods, and kits for ocular drug delivery are described herein. In some embodiments, an apparatus includes a housing, an energy storage member, a barrel, and a hub. The housing has a proximal end portion and a distal end portion, and contains the energy storage member. The barrel has a proximal end portion and a distal end portion. The proximal end portion of the barrel is coupled to the distal end portion of the housing. The barrel is configured to contain a medicament and includes at least a portion of a piston and an elastomeric member. The piston is configured to move the elastomeric member within the barrel in response to a force produced by the energy storage member when the energy storage member is actuated. The hub is coupled to the distal end portion of the barrel, and includes an inner surface and an outer surface. The inner surface of the hub defines a nozzle through which the medicament flows when the elastomeric member moves within the barrel. The nozzle and the energy storage member are collectively configured to produce a fluid jet to access a target location within an eye when the energy storage member is actuated. The outer surface of the hub forms a fluid-tight seal with a surface of the eye.

In some embodiments, a method includes moving a distal end portion of a hub of a medical injector into contact with a surface of an eye. A force is exerted to maintain contact between the distal end portion of the hub and the surface of the eye, such that an outer surface of the hub forms a fluid-tight seal with the surface of the eye. The medical injector is then actuated to cause the medical injector to: A) convey a fluid jet of a medicament from a nozzle defined by the hub, the fluid jet characterized by a first pressure sufficient to penetrate a sclera of the eye, B) adjust, after the fluid jet is initially conveyed, a pressure of the fluid jet to a second pressure, the second pressure sufficient to form or expand a suprachoroidal space, and C) adjust the pressure of the fluid jet to a third pressure, the third pressure sufficient to deliver the medicament to the targeted ocular tissue via the suprachoroidal space. In some embodiments, the adjustment of the pressure of the fluid jet after the initial conveyance occurs in response to the back pressure applied to the fluid in the injector (e.g. via the resistance of the tissue) is changed. Specifically, when the fluid jet reaches the suprachoroidal space, the resistance to the fluid can decrease. In response to this decrease, the method can include adjusting the pressure to prevent the jet from penetrating through the choroid. Similarly, in some embodiments, the adjustment of the pressure of the fluid jet after the suprachoroidal space is expanded or formed occurs in response to the back pressure applied to the fluid in the injector.

In some embodiments, an apparatus includes a barrel, a hub, and an energy source. The barrel has a proximal end portion and a distal end portion. The barrel is configured to contain a medicament and includes a piston and an elastomeric member. The piston is configured to move the elastomeric member within the barrel in response to a force. The hub is coupled to the distal end portion of the barrel, and includes an inner surface that defines an opening through which the medicament flows when the elastomeric member moves within the barrel. The energy source is configured to deliver a focused energy beam to a targeted tissue. The focused energy beam produces a delivery pathway within the targeted tissue through which the medicament flows from the opening of the hub.

In some embodiments, the focused energy beam can be any suitable mechanism to ablate, separate and/or disrupt the targeted tissue to form the delivery pathway. For example, in some embodiments, the focused energy beam can be an electrical energy beam, a magnetic energy beam, a light energy beam, a non-visible beam of electromagnetic energy (e.g., ultraviolet radiation), a beam of heat (or infrared) energy, or an acoustic energy beam.

In some embodiments, a method includes producing an energy source from a medicament delivery device to a surface of an eye to deliver a focused energy beam having a prescribed focal depth to produce a pathway to a targeted ocular tissue, such as the suprachoroidal space, the subretinal space, the ciliary muscle, the trabecular meshwork or other ocular region. The method further includes actuating the medicament delivery device to cause the medicament delivery device to convey a medicament from a barrel and through the pathway to deliver the medicament to the targeted ocular tissue.

In some embodiments, an apparatus includes a housing and a rigid member. The housing has a distal end portion and contains the rigid member. The rigid member has a distal end portion that is coated with a medicament. The rigid member is configured to move within the housing in response to a force such that the distal end portion of the rigid member extends beyond the distal end portion of the housing into a targeted tissue. When the distal end portion of the rigid member enters into a targeted tissue, the medicament is transferred from the distal end portion of the rigid member to the targeted tissue.

In some embodiments, a method includes placing a distal end portion of a housing of a medicament delivery device into contact with a surface of an eye. A rigid member of the medicament delivery device is moved within the housing in response to a force such that a distal end portion of the rigid member extends beyond a distal portion of the housing into a targeted ocular tissue. A medicament is then delivered to the targeted ocular tissue via the distal end portion of the rigid member.

In some embodiments, a method includes administering a medicament into a suprachoroidal space of an eye. A probe is then applied to the surface of the eye. The probe is then actuated to convey energy into the eye to facilitate movement of the medicament to a targeted tissue.

In some embodiments, an apparatus includes a housing and an electrode. The housing has a distal end portion that is configured to contact a surface of an eye and to separate an outer portion of the eye. The housing defines a reservoir that is configured to contain a medicament having an ionic charge. The electrode is coupled to the housing. The electrode is configured to produce a charge that is sufficient to convey the medicament from the reservoir to a targeted region within the eye.

In some embodiments, an apparatus includes a housing, a contact member, and an electrode. The housing has a distal end portion that is configured to contact a surface of an eye. The housing defines a reservoir that is configured to contain a medicament having an ionic charge. The contact member is coupled to the housing and is configured to separate an outer portion of the eye to define a first pathway through which the distal end portion of the housing is disposed. The electrode is also coupled to the housing. The electrode is configured to produce a charge that is sufficient to convey the medicament from the reservoir to a targeted region within the eye through a second pathway below the outer portion of the eye.

In some embodiments, an apparatus includes a housing, an electrode, and a controller. The housing has a distal end portion that is configured to contact a surface of an eye. The housing defines a reservoir that is configured to contain a medicament having an ionic charge. The electrode is coupled to the housing. The electrode is configured to produce a charge that is sufficient to convey the medicament from the reservoir to a targeted region within the eye. The controller is configured to adjust the charge to convey the medicament to a medicament delivery depth within a predetermined range.

In some embodiments, a method includes moving a distal end portion of a housing of a medicament delivery device into contact with a surface of an eye. The medicament delivery device is then actuated to cause the medicament delivery device to: A) cut a first pathway through an outer portion of the eye, and B) apply a voltage to an electrode of the medicament delivery device to convey a medicament within the medicament delivery device through a second pathway below the outer portion of the eye to a targeted region within the eye.

In some embodiments, a method includes moving a distal end portion of a housing of a medicament delivery device into contact with a surface of an eye. The medicament delivery device is then actuated to cause the medicament delivery device to: A) apply a voltage to an electrode of the medicament delivery device to convey a medicament within the medicament delivery device through a pathway to a targeted region within the eye, and B) adjust the voltage to convey the medicament to a medicament delivery depth within a predetermined range.

In some embodiments, an apparatus is a medicament delivery membrane that is configured to be disposed at least partially within an eye between a conjunctiva and a sclera and includes a reservoir. The reservoir is configured to contain a medicament.

In some embodiments, an apparatus includes a housing, a contact member, and a delivery member. The housing has a distal end portion that is configured to contact a surface of an eye. The contact member is movably disposed within the housing and is configured to separate a conjunctiva of the eye to define a pathway. The delivery member is movably disposed within one of the housing or the contact member. The delivery member is configured to convey a medicament delivery membrane through the pathway and position the medicament delivery membrane on a surface of a sclera of the eye.

In some embodiments, a method includes positioning a medicament delivery device on a surface of an eye, the medicament delivery device including a housing and a contact member. The contact member of the medicament delivery device is then moved relative to the housing of the medicament delivery device to produce a pathway through a conjunctiva of the eye. A medicament delivery membrane is then delivered through the pathway such that the medicament delivery membrane is disposed between the conjunctiva and a sclera of the eye.

In some embodiments, a method includes positioning a medicament delivery device on a surface of an eye, the medicament delivery device including a housing having a distal end portion. The distal end portion of the housing of the medicament delivery device is then moved such that it creates a pathway through a conjunctiva of the eye. A medicament delivery membrane is then delivered through the pathway and disposed between the conjunctiva and a sclera of the eye.

In some embodiments, a method includes delivering a medicament to a vitreous of an eye. A magnetic field is then produced at a location outside of an outer surface of the eye to move the medicament from the vitreous of the eye to a targeted region within the eye.

In some embodiments, a method includes placing a medicament delivery device on a surface of an eye. The medicament delivery device is then actuated to cause the medicament delivery device to: A) deliver a medicament to a vitreous of an eye, and B) apply a charge to an electrode of the medicament delivery device to move the medicament from the vitreous of the eye to a targeted region within the eye. The targeted region can be, for example, the suprachoroidal space (SCS), the subretinal space (SRS), or any other suitable region within the eye.

In some embodiments, an anatomical positioning apparatus includes a guide member configured to be disposed about a portion of a face surrounding an eye. The guide member has a side wall defining an opening through which a puncture member can be disposed to define a pathway within the eye. The guide member includes at least one index portion configured to receive an anatomical landmark of the face (such as the bridge of the nose, the top of an ear, etc.) to position the side wall at a predetermined position relative to the eye.

In some embodiments, a method includes inserting a distal end portion of a puncture member of a medical injector into a target tissue to define a delivery passageway within the target tissue. The puncture member defines a lateral opening through which a medicament can be conveyed. The method also includes exerting, after inserting, a force on an actuation rod of the medical injector. The force has a magnitude of less than a threshold value. The force produces movement of the actuation rod within a medicament container when the lateral opening is disposed within a first region of the target tissue. Movement of a distal end portion of the actuation rod within the medicament container is limited when the lateral opening is disposed within a second region of the target tissue. The method further includes conveying, in response to the exerting, the medicament from the medicament container into the first region of the target tissue via the lateral opening in response to movement of the actuation rod.

In some embodiments, a method includes inserting a distal end portion of a delivery assembly of a medical injector into a target tissue to define a delivery passageway within the target tissue. The delivery assembly includes an outer member, an inner member, and an actuator. The method also includes exerting a force on the actuator, the force having magnitude of less than a threshold value and which is sufficient to convey a first substance from the delivery assembly when the distal end portion of the delivery assembly is disposed within a first region of the target tissue. However, the force is insufficient to convey the first substance from the delivery assembly when the distal end portion of the delivery assembly is disposed within a second region of the target tissue. The method includes moving the inner member relative to the outer member after the first substance is conveyed from the delivery assembly. The method further includes conveying a second substance from the inner member into the target tissue after the inner member is moved.

In some embodiments, an apparatus includes a housing, a delivery member, and an electronic circuit system. The housing defines an opening configured to receive a portion of a medicament container therein. The delivery member is coupled to a distal end portion of the housing such that a proximal end portion of the delivery member is in fluid communication with the medicament container and a distal end portion of the delivery member is disposed outside of the housing. The electronic circuit system includes a sensor and an output device. The sensor is coupled to one of the housing or the delivery member. The sensor is configured to produce a feedback signal associated with a depth of the distal end portion of the delivery member within a target tissue. For example, in some embodiments, the sensor can produce a signal associated with the distance through which the needle has traveled (e.g., 900 µm, 1100 µm, etc.). In other embodiments, the sensor can produce a signal when there is a loss of resistance that occurs when the device enters the suprachoroidal space. The electronic circuit system is configured to produce an electronic output via the output device in response to the feedback signal.

In some embodiments, an apparatus includes a lens member and a microneedle assembly. The lens member has a central portion and a peripheral portion. The lens member is configured to be coupled to a surface of an eye such that the central portion is disposed about a cornea. The central portion has an optical property to facilitate vision therethrough. The microneedle assembly is coupled to the peripheral portion. The microneedle assembly includes an outer ember and an inner member. The inner member is configured to move within the outer member between a first position and a second position. The inner member is configured to penetrate the surface of the eye when the lens member is coupled to the surface of the eye and the inner membrane is in the second position. The inner member defines a lumen through which a medicament can be conveyed.

In some embodiments, a method includes administering a carrier to a vascular system of a patient. The carrier is formulated to contain a medicament. The method then includes actuating an energy source at a location outside of an outer surface of an eye to produce an energy beam to degrade the carrier thereby releasing the medicament such that the medicament is moved from a choroidal blood vessel to a targeted region within the eye.

In some embodiments, a method includes administering a medicament into a choroidal blood vessel of an eye. The medicament is formulated to be in an inactive form. The method also includes actuating an energy source at a location outside of an outer surface of the eye to produce an energy beam. The energy beam degrades a portion of the medicament thereby activating the medicament.

In some embodiments, an apparatus includes a housing, an electronic circuit system, and a delivery member. The housing defines a reservoir that is configured to contain a medicament. The housing also includes an energy source that is configured to apply an energy to the medicament. The electronic circuit system is configured to adjust the energy to regulate a temperature of the medicament. In some embodiments, the delivery member is configured to move within the housing in response to a force such that a distal end portion of the delivery member extends beyond a distal end portion of the housing into a target tissue for delivery of the medicament.

In some embodiments, an apparatus includes a housing, an energy source, an electronic circuit system, a delivery member, and an actuator. The housing has a distal end portion and defines a reservoir that is configured to contain a medicament. The energy source is coupled to the distal end portion of the housing and is configured to deliver energy to a target tissue. The electronic circuit system is configured to adjust the energy source to regulate a temperature of the target tissue during delivery of the energy. In some embodiments, the delivery member is movably coupled to the housing and it is configured to convey the medicament to the target tissue. The actuator is configured to move a distal end portion of the delivery member relative to the housing and expel the medicament from the reservoir when actuated.

In some embodiments, an apparatus includes a housing, a delivery member, and an electronic circuit system. The housing has a distal end portion and defines a reservoir configured to contain a medicament. The delivery member is coupled to the distal end portion of the housing. The delivery member is configured to convey the medicament to a target tissue. A distal end portion of the delivery member includes an energy source that is configured to deliver energy to the target tissue. The electronic circuit system is configured to adjust the energy source to regulate a temperature of the target tissue.

The term "about" when used in connection with a referenced numeric indication means the referenced numeric indication plus or minus up to 10 percent of that referenced numeric indication. For example, "about 100" means from 90 to 110.

As used herein, the singular forms "a," "an," and "the" include plural referents unless the context clearly dictates otherwise. Thus, for example, the term "a member" is intended to mean a single member or a combination of members, "a material" is intended to mean one or more materials, or a combination thereof.

As used herein, the words "proximal" and "distal" refer to the direction closer to and away from, respectively, an operator (e.g., surgeon, physician, nurse, technician, etc.) who would insert the medical device into the patient, with the tip-end (i.e., distal end) of the device inserted inside a patient's body first. Thus, for example, the end of an injection device described herein first inserted inside the patient's body would be the distal end, while the opposite end of the injection device (e.g., the end of the medical device being manipulated by the operator) would be the proximal end of the device.

As used herein, a "set" can refer to multiple features or a singular feature with multiple parts. For example, when referring to set of walls, the set of walls can be considered as one wall with distinct portions, or the set of walls can be considered as multiple walls.

As used herein, the terms "medicament container", and "medicament containment chamber" are used interchangeably to refer to an article configured to contain a volume of a substance, for example, a medicament. A medicament container can include a vial, ampule, inner portion of a syringe, or the like.

As used in this specification and the appended claims, the term "medicament" includes any constituent of a therapeutic substance. A medicament can include such constituents regardless of their state of matter (e.g., solid, liquid or gas). Moreover, a medicament can include the multiple constituents that can be included in a therapeutic substance in a mixed state, in an unmixed state and/or in a partially mixed state. A medicament can include both the active constituents and inert constituents of a therapeutic substance. Accordingly, as used herein, a medicament can include non-active constituents such as, water, colorant or the like. A medicament can also include a therapeutic substance that is encapsulated or otherwise contained within a carrier such as a liposome, nanoparticle, microparticle, or the like.

The term "fluid-tight" is understood to encompass both a hermetic seal (i.e., a seal that is gas-impervious) as well as a seal that is only liquid-impervious. The term "substantially" when used in connection with "fluid-tight," "gas-impervious," and/or "liquid-impervious" is intended to convey that, while total fluid imperviousness is desirable, some minimal leakage due to manufacturing tolerances, or other practical considerations (such as, for example, the pressure applied to the seal and/or within the fluid), can occur even in a "substantially fluid-tight" seal. Thus, a "substantially fluid-tight" seal includes a seal that prevents the passage of a fluid (including gases, liquids and/or slurries) therethrough when the seal is maintained at a constant position and at fluid pressures of less than about 5 pounds per square inch gage (psig), less than about 10 psig, less than about 20 psig, less than about 30 psig, less than about 50 psig, less than about 75 psig, less than about 100 psig and all values in between. Similarly, a "substantially liquid-tight" seal includes a seal that prevents the passage of a liquid (e.g., a liquid medicament) therethrough when the seal is maintained at a constant position and is exposed to liquid pressures of less than about 5 psig, less than about 10 psig, less than about 20 psig, less than about 30 psig, less than about 50 psig, less than about 75 psig, less than about 100 psig and all values in between.

Figure 2:
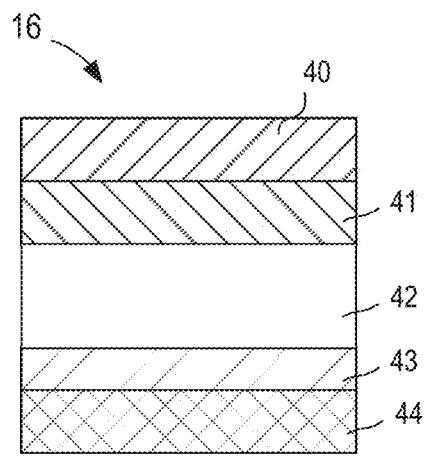
FIG. 2 is a cross-sectional view of a portion of the human eye of FIG. 1 taken along the line 2-2.
Figure 3:
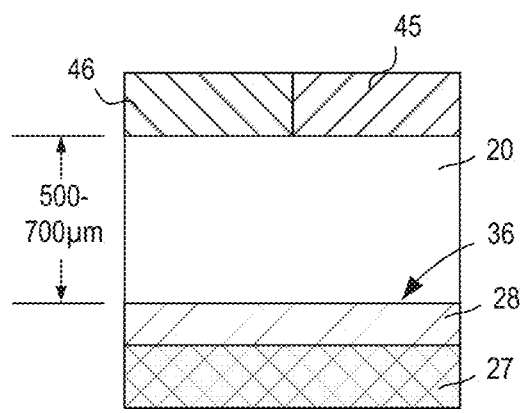
FIGS. 3 and 4 are cross-sectional views of a portion of the human eye of FIG. 1 taken along the line 3-3, illustrating the suprachoroidal space without and with, respectively, the presence of a fluid.
Figure 4:
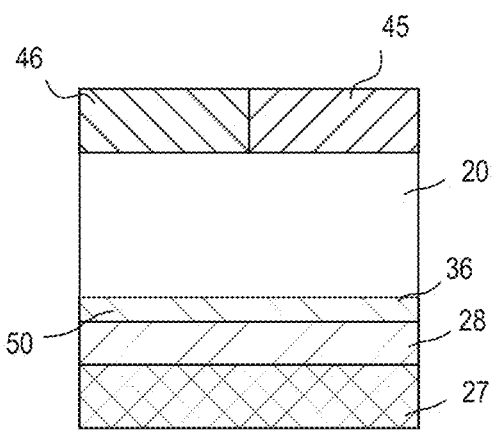

As used herein, "ocular tissue" and "eye" include both the anterior segment of the eye (i.e., the portion of the eye in front of the lens) and the posterior segment of the eye (i.e., the portion of the eye behind the lens). For reference, FIGS. 1-4 are a various views of an eye 10 (with FIGS. 2-4 being cross-sectional views). While specific regions are identified, those skilled in the art will recognize that the proceeding identified regions do not constitute the entirety of the eye 10, rather the identified regions are presented as a simplified example suitable for the discussion of the embodiments herein. The eye 10 includes both an anterior segment 12 (the portion of the eye in front of and including the lens) and a posterior segment 14 (the portion of the eye behind the lens). The anterior segment 12 is bounded by the cornea 16 and the lens 18, while the posterior segment 14 is bounded by the sclera 20 and the lens 18. The anterior segment 12 is further subdivided into the anterior chamber 22, between the iris 24 and the cornea 16, and the posterior chamber 26, between the lens 18 and the iris 24. The cornea 16 and the sclera 20 collectively form a limbus 38 at the point at which they meet. The exposed portion of the sclera 20 on the anterior segment 12 of the eye is protected by a clear membrane referred to as the conjunctiva 45 (see e.g., FIGS. 2 and 3). Underlying the sclera 20 is the choroid 28 and the retina 27, collectively referred to as retinachoroidal tissue. A vitreous humour 30 (also referred to as the "vitreous") is disposed between a ciliary body 32 (including a ciliary muscle and a ciliary process) and the retina 27. The anterior portion of the retina 27 forms an or a serrata 34. The loose connective tissue, or potential space, between the choroid 28 and the sclera 20 is referred to as the suprachoroid. FIG. 2 illustrates the cornea 16, which is composed of the epithelium 40, the Bowman's layer 41, the stroma 42, the Descemet's membrane 43, and the endothelium 44. FIG. 3 illustrates the sclera 20 with surrounding Tenon's Capsule 46 or conjunctiva 45, suprachoroidal space 36, choroid 28, and retina 27, substantially without fluid and/or tissue separation in the suprachoroidal space 36 (i.e., the in this configuration, the space is "potential" suprachoroidal space). As shown in FIG. 3, the sclera 20 has a thickness between about 500 µm and 700 µm. FIG. 4 illustrates the sclera 20 with the surrounding Tenon's Capsule 46 or the conjunctiva 45, suprachoroidal space 36, choroid 28, and retina 27, with fluid 50 in the suprachoroidal space 36.

Figure 5:
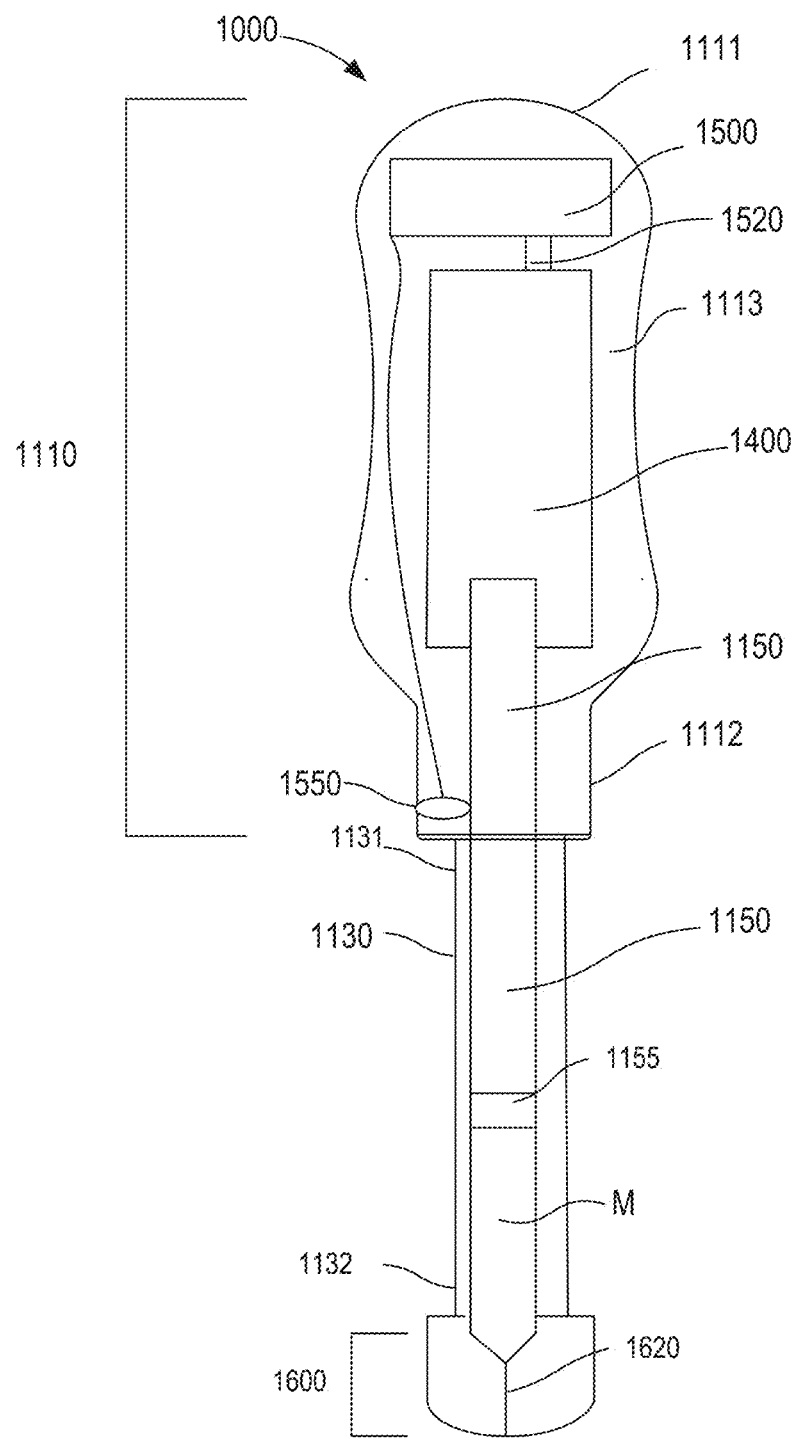
FIG. 5 is a schematic illustration of a jet injector apparatus according to an embodiment.
Figure 6:
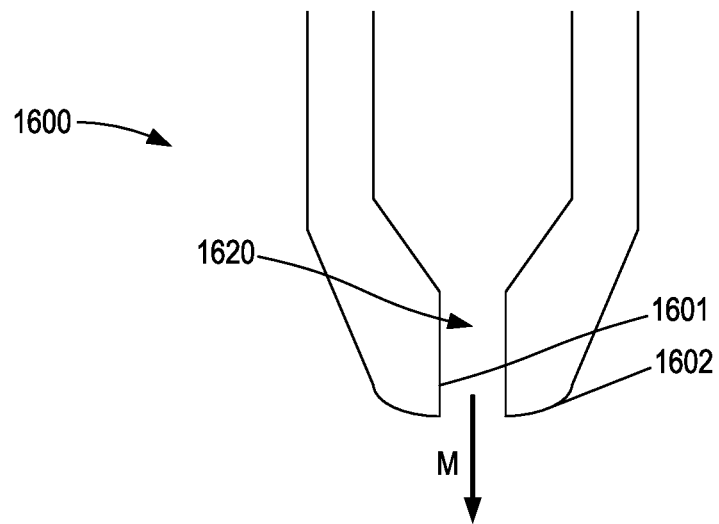
FIG. 6 is a close up view of the hub of the jet injector apparatus shown in FIG. 5.

In some embodiments, an apparatus can facilitate targeted delivery of a drug to a specific ocular tissue via a fluid jet. For example, FIGS. 5 and 6 show various views of a jet injector apparatus 1000 according to an embodiment. The jet injector apparatus 1000 includes a housing 1110, an energy storage member 1400, a barrel (also referred to as a medicament container) 1130, and a hub 1600.

As shown in FIG. 5, the housing 1110 has a proximal end portion 1111 and a distal end portion 1112, and defines an inner volume 1113. The energy storage member 1400 is contained in the inner volume 1113. In some embodiments, the inner volume 1113 can optionally contain components of an electronic control system, such as a controller 1500, connectors 1520, or sensors 1550. The housing 1110 is configured to be coupled to the barrel 1130. The housing 1110 can be a monolithic housing or it can include two or more portions which can be joined together to form the housing 1110.

As shown in FIG. 5, the barrel 1130 has a proximal end portion 1131 and a distal end portion 1132. The proximal end portion 1131 of the barrel 1130 is coupled to the distal end portion 1111 of the housing 1110. The barrel 1130 can be coupled to the housing 1110 by any suitable mechanism. For example, in some embodiments, the barrel 1130 can include a flange (not shown) that is coupled within the inner volume 1113 of the housing 1110 by a fastening feature (e.g., mounts, notches, grooves, indents, slots, shoulders, or the like). In other embodiments, the barrel 1130 can be threadedly coupled to the distal end portion 1112 of the housing 1110. The barrel (or medicament container) 1130 is configured to contain a medicament M, and includes at least a portion of a piston 1150 and an elastomeric member 1155. The medicament M, and any other medicaments described herein can be any suitable drug, medicament or therapeutic agent of the types mentioned herein.

The barrel (or medicament container) 1130 can be any suitable container that can receive and/or contain the medicament M and be coupled to the housing 1110 and the hub 1600 as described herein. For example, in some embodiments the barrel 1130 can be a commercially available syringe such as, for example, a BD™ 1 CC syringe, or any other commercially available syringe. In other embodiments, the barrel 1130 can be a cartridge, vial or ampule within which the medicament M can be contained. Moreover, the barrel 1130 can have any suitable volume and/or size. In some embodiments, the volume of the barrel 1130 can about 0.5 mL or less. In other embodiments, the volume of the barrel 1130 can be about 0.1 mL or less.

The proximal end portion of the piston 1150 is operatively coupled to the energy storage member 1400 contained in the housing 1110. The piston 1150 is configured to move the elastomeric member 1155 within the barrel 1130 in response to a force produced by the energy storage member 1400 when the energy storage member 1400 is actuated. The force causes the elastomeric member 1155 to expel the medicament M from the barrel 1130 into and/or through the hub 1600 to produce a fluid jet J to access a target location within the eye, as described in more detail below.

The energy storage member 1400 can be any suitable mechanism for producing the force to move the piston 1150 and/or the elastomeric member 1155. For example, in some embodiments, the energy storage member 1400 can include a compressed gas container, or a container containing a propellant. In other embodiments, the energy storage member 1400 can include a magnetic energy storage member, an electronic energy storage member (e.g., a battery or a capacitor) or the like. In yet other embodiments, the energy storage member can include a mechanism for converting the stored energy to a linear force to move the piston 1150. For example, in some embodiments, the energy storage member can include a motor or other linear actuator.

The hub 1600 is coupled to the distal end portion 1132 of the barrel 1130. FIG. 6 shows an expanded view of the hub 1600. As shown, the hub 1600 includes an inner surface 1601 and an outer surface 1602. The inner surface 1601 of the hub 1600 defines a nozzle 1620 through which the medicament M flows when the elastomeric member 1155 moves within the barrel 1130. The nozzle 1620 and the energy storage member 1400 are collectively configured to produce a fluid jet J (see FIG. 7) to access a target location within an eye when the energy storage member 1400 is actuated. More specifically, as described below, the force produced by the energy storage member 1400 and the size and flow characteristics of the nozzle 1620 are such that the pressure of the fluid jet J exiting the hub 1600 can define a delivery pathway within the ocular tissue having a desired depth. For example, in some embodiments, the nozzle 1620 and the energy storage member 1400 are collectively configured such that the fluid jet J defines a delivery pathway within the ocular tissue that reaches, but does not extend significantly deeper than, the suprachoroidal space (SCS) and/or the subretinal space (SRS). In some embodiments, the nozzle 1620 and the energy storage member 1400 are collectively configured such that the fluid jet J defines a delivery pathway within the ocular tissue having a depth of between about 800 μm and about 1200 μm. In other embodiments, the nozzle 1620 and the energy storage member 1400 are collectively configured such that the fluid jet J defines a delivery pathway within the ocular tissue having a depth of between about 600 μm and about 1400 μm.

The outer surface 1602 of the hub 1600 forms a substantially fluid-tight seal with a surface of the eye. More particularly, the outer surface 1602 forms a substantially fluid-tight seal with a target surface around the delivery pathway to limit the amount of leakage during use. The outer surface 1602 of the hub 1600 can be any suitable shape, size, and/or configuration and can be configured to contact a portion of the ocular tissue during an injection event. For example, as shown in FIG. 6, the outer surface 1602 has a convex distal end surface, which is configured to contact a target surface of a target tissue when a substance is conveyed through the nozzle 1620 into the target tissue. In some embodiments, the distal end surface includes a sealing portion (not identified in the FIGS.) configured to define a substantially fluid-tight seal with the target surface when the distal end surface is in contact with the target surface. For example, the distal end surface of the outer surface 1602 can deform the target surface such that the sealing portion is contiguous with the target surface and forms the substantially fluid-tight seal.

In some embodiments, the outer surface 1602 can be formed from a material or combination of materials that is/are relatively flexible and/or that has/have a relatively low durometer. In some embodiments, the outer surface 1602 can be formed from a material with a durometer that is sufficiently low to limit and/or prevent damage to the ocular tissue when placed in contact therewith. In some embodiments, the outer surface 1602 can be configured to deform (e.g., elastically or plastically) when placed in contact with the ocular tissue. In other embodiments, the outer surface 1602 can be formed from a material of sufficient hardness such that the target tissue (and not the outer surface 1602) is deformed when the outer surface 1602 is placed in contact with and/or pressed against the target tissue. In some embodiments, for example, the outer surface 1602 is constructed from a medical grade stainless steel, and has a surface finish of less than about 1.6 μm Ra. In this manner, the surface finish can facilitate the formation of a substantially fluid-tight seal between the outer surface 1602 and the target tissue.

The hub 1600 can be coupled to the barrel 1130 using any suitable coupling features, for example, Luer connectors, threads, snap-fit, latch, lock, friction fit, or any other suitable coupling features. Although the hub 1600 is shown and described as being a separate component from the barrel 1130, in other embodiments, the barrel 1130 and the hub 1600 can be monolithically constructed.

In some embodiments, the housing 1110 includes a controller 1500 that can control the amount of force produced by the energy storage member 1400 and/or the pressure of the fluid jet J conveyed from the hub 1600. In this manner, the jet injector apparatus 1000 can actively control the penetration depth of the fluid jet J exiting the hub 1600. In such embodiments, the controller 1500 can include a memory, a processor, and an input/output module (or interface). In some embodiments, the controller 1500 can also include a pressure feedback module (not shown) that receives a pressure signal from the pressure sensor 1550. A pressure feedback module includes circuitry, components, and/or code to produce a control signal that can facilitate controlling movement of the elastomeric member 1155 by the energy storage member 1400. In some embodiments, the controller 1500 can also include a position feedback module (not shown) that receives a position, velocity, and/or acceleration information associated with movement of the piston 1150. The controller 1500 can be coupled to a computer (not shown) or other input/output device via the input/output module (or interface).

The processor (and any of the processors described herein) can be any processor configured to, for example, write data into and read data from the memory of the controller 1500, and execute the instructions and/or methods stored within the memory. Furthermore, the processor can be configured to control operation of the other modules within the controller (e.g., the pressure feedback module and the position feedback module). Specifically, the processor can receive a signal including user input, pressure data, distance measurements or the like and determine an amount of power to be exerted on the piston 1150, the desired timing and sequence of the piston pulses and the like. In other embodiments, the processor (and any of the processors described herein) can be, for example, an application-specific integrated circuit (ASIC) or a combination of ASICs, which are designed to perform one or more specific functions. In yet other embodiments, the microprocessor can be an analog or digital circuit, or a combination of multiple circuits.

The memory device of the controller (and any of the memory devices described herein) can be any suitable device such as, for example, a read only memory (ROM) component, a random access memory (RAM) component, electronically programmable read only memory (EPROM), erasable electronically programmable read only memory (EEPROM), registers, cache memory, and/or flash memory. Any of the modules (the pressure feedback module and the position feedback module) can be implemented by the processor and/or stored within the memory.

The electrode controller 1500 includes a pressure feedback module. The pressure feedback module includes circuitry, components and/or code to produce a control signal (not shown in FIG. 5) that can facilitate controlling movement of the elastomeric member 1155 by the energy storage member 1400.

Figure 7:
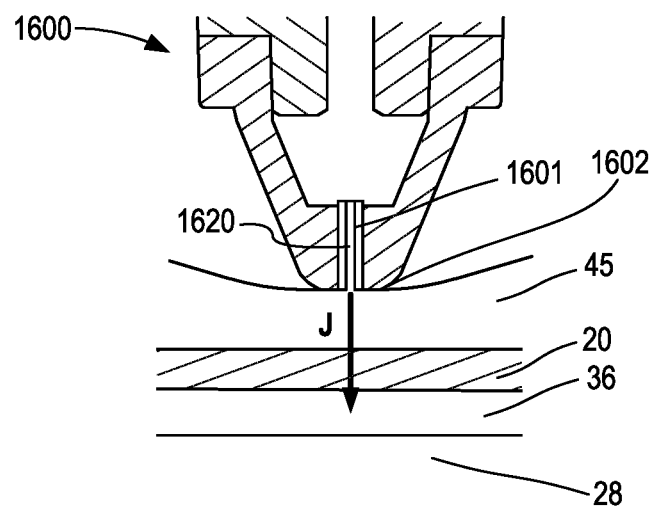
FIG. 7 shows the hub of the jet injector apparatus shown in FIGS. 5 and 6 in contact with a surface of an eye and a fluid jet being injected from the hub of the jet injector apparatus into a sclera of the eye.

In some embodiments, a method includes delivering a fluid jet of medicament to a targeted ocular tissue. This method is shown in FIG. 7, which illustrates a portion of the jet injector 1000 delivering a fluid jet J within the eye. Although shown as being performed using the jet injector 1000, in other embodiments, the method can be performed using any suitable device. The method includes moving an outer surface 1602 of a hub 1600 of a jet injection apparatus 1000 into contact with a surface of an eye. More particularly, the outer surface 1602 is moved into contact with and/or can deform the conjunctiva 45. In some embodiments, the method includes exerting a force so that the outer surface 1602 of the hub 1600 forms a substantially fluid-tight seal with the surface of the eye. The jet injection apparatus 1000 is actuated to cause the jet injection apparatus 1000 to convey a fluid jet J of a medicament from a nozzle defined by the inner surface 1601 of the hub 1600. The force produced by the energy storage member 1400 and the size and flow characteristics of the nozzle 1620 are such that the pressure of the fluid jet J defines a delivery pathway through the conjunctiva 45 and the sclera 20 having a desired depth. In this manner, the fluid jet J can reach and/or define the suprachoroidal space 36 between the sclera 20 and the choroid 28. For example, in some embodiments, the method includes defining, via a fluid jet J, a delivery pathway within the ocular tissue that reaches, but does not extend significantly deeper than, the suprachoroidal space 36. In some embodiments, the nozzle 1620 and the energy storage member 1400 are collectively configured such that the fluid jet J defines a delivery pathway within the ocular tissue having a depth of between about 800 μm and about 1200 μm. In other embodiments, the energy storage member 1400 are collectively configured such that the fluid jet J defines a delivery pathway within the ocular tissue having a depth of between about 600 μm and about 1400 μm.

In some embodiments, the method can include varying the pressure of the fluid jet J to facilitate delivery of the medicament M to the desired location (e.g., the suprachoroidal space 36). For example, in some embodiments, the jet injection apparatus 1000 can be actuated to produce a first pressure, which is sufficient to cause the medicament M to penetrate a sclera 20 of an eye. After the medicament M is initially conveyed, the jet injection apparatus 1000 can adjust the fluid jet J to a second pressure, which is sufficient to form or expand a suprachoroidal space 36. The jet injection apparatus 1000 then adjusts the fluid jet J to a third pressure, which is sufficient to deliver the medicament M to the targeted ocular issue via the suprachoroidal space 36.

Figure 8:
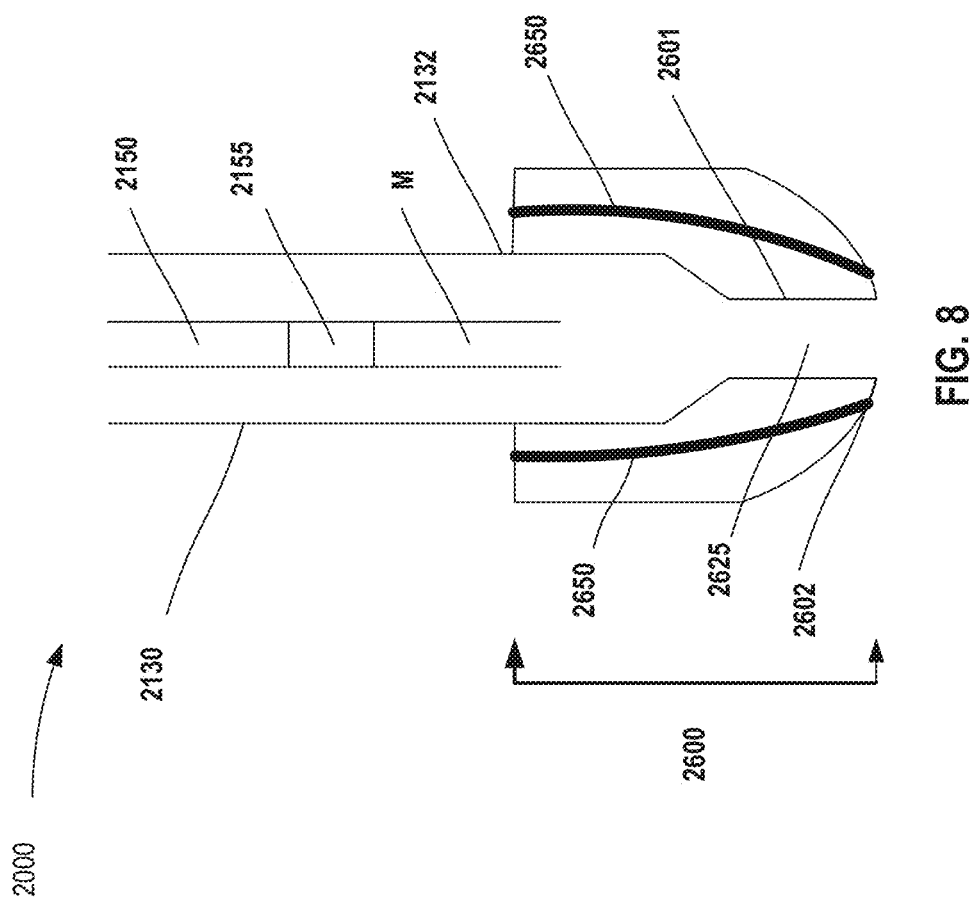
FIG. 8 is a schematic illustration of a medicament delivery device according to an embodiment.
Figure 9:
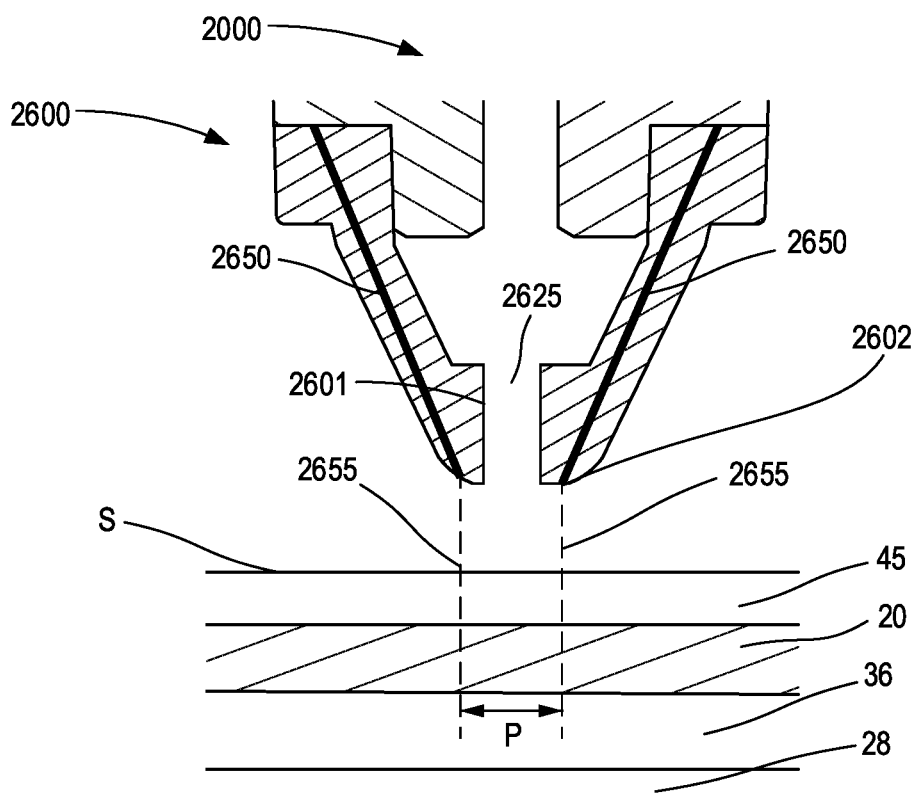
FIGS. 9 and 10 are close-up views of a portion of the medicament delivery device shown in FIG. 8 in various stages of use.
Figure 10:
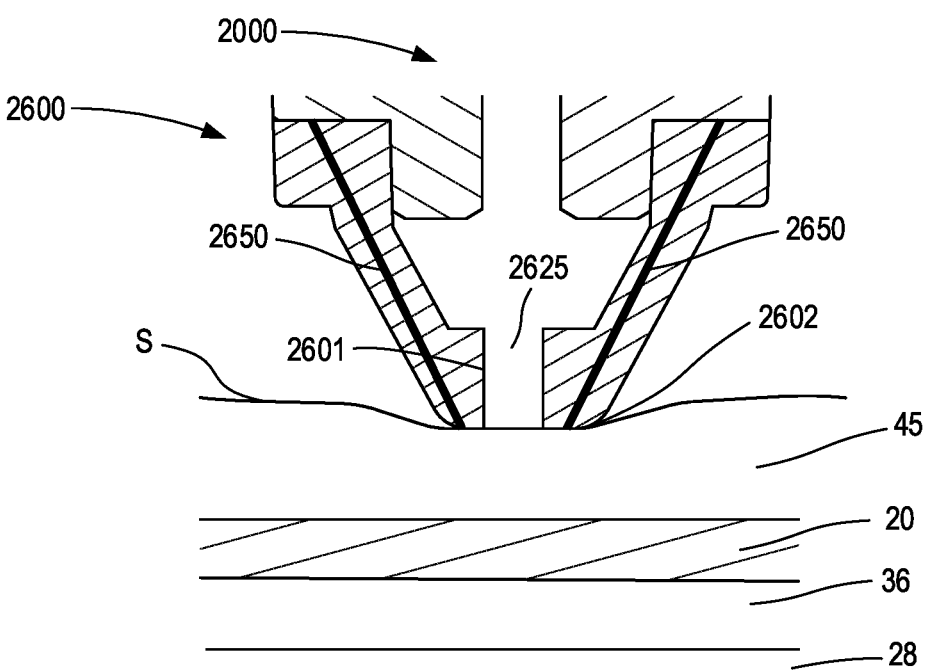

Although the device 1000 is shown and described above as including a nozzle 1620 that produces a fluid jet J to define a delivery pathway to the desired region of tissue (e.g., the suprachoroidal space 36), in other embodiments a medicament delivery device can define a delivery pathway within a bodily tissue using any suitable mechanism. For example, in some embodiments, a device can include an energy source that defines a pathway within a bodily tissue through which a drug can be delivered. Moreover, in some embodiments, a device can include a distal end surface that is spaced apart from the target surface when the pathway is being defined (e.g., the device can be a "non-contact" system) that produces the pathway. For example, FIGS. 8-10 show various views of a medicament delivery device 2000 that provides a pathway via a non-contact system according to an embodiment. The medicament delivery device 2000 includes a barrel (also referred to as a medicament container) 2130, a hub 2600, and an energy source 2650.

As shown in FIG. 8, the barrel (or medicament container) 2130 has a distal end portion 2132 that is coupled to a proximal end portion the hub 2600 using any suitable coupling features, for example, Luer connectors, threads, snap-fit, latch, lock, friction fit, or any other suitable coupling features. Although the hub 2600 is shown and described as being a separate component from the barrel 2130, in other embodiments, the barrel 2130 and the hub 2600 can be monolithically constructed.

The barrel (or medicament container) 2130 is configured to contain a medicament M. The medicament M, and any other medicaments described herein can be any suitable drug, medicament or therapeutic agent of the types mentioned herein.

The barrel (or medicament container) 2130 can be any suitable container that can receive and/or contain the medicament M. For example, in some embodiments the barrel 2130 can be a commercially available syringe such as, for example, a BD™ 1 CC syringe, or any other commercially available syringe. In other embodiments, the barrel 2130 can be a cartridge, vial or ampule within which the medicament M can be contained. Moreover, the barrel 2130 can have any suitable volume and/or size. In some embodiments, the volume of the barrel 2130 can about 0.5 mL or less. In other embodiments, the volume of the barrel 2130 can be about 0.1 mL or less.

The barrel 2130 includes a piston 2150 and an elastomeric member 2155. The piston 2150 is configured to move the elastomeric member 2155 within the barrel 2130 in response to a force exerted on the piston 2150. The force causes the elastomeric member 2155 to expel the medicament M from the barrel 2130 into and/or through the hub 2600, as described in more detail below.

The hub 2600 is coupled to the distal end portion 2132 of the barrel 2130. FIG. 9 shows an expanded view of the hub 2600. As shown, the hub 2600 includes an inner surface 2601 and an outer surface 2602. The inner surface 2601 of the hub 2600 defines an opening 2625 through which the medicament M flows when the elastomeric member 2155 moves within the barrel 2130.

The hub 2600 also includes an energy source 2650 that is configured to deliver a focused energy beam to a targeted portion of a tissue. Thus, when actuated the energy source 2650 can define a delivery pathway P for a medicament M within a tissue having a desired depth. Because the delivery pathway P is defined by the energy beam produced by the energy source 2650, the energy source 2650 need not be disposed within the target tissue. For example, in some embodiments, the hub 2600 does not contact the target tissue, but rather causes the energy source 2650 to deliver a focused energy beam 2655 having a prescribed focal depth to produce a delivery pathway P within a tissue. In this manner, the delivery pathway P can be produced without the device (e.g., the hub 2600 and/or the energy source 2650) contacting the target tissue. FIG. 9 shows such an embodiment. In FIG. 9, the energy source 2650 delivers focused energy beams 2655 to produce a delivery pathway P to and/or below the surface of an eye S. In some embodiments, the delivery pathway P reaches, but does not extend significantly deeper than, the suprachoroidal space 36. In some embodiments, the energy source 2650 is configured and/or controlled such that the focused energy beams 2655 define a delivery pathway P within the ocular tissue having a depth of between about 800 µm and about 1200 µm. In other embodiments, the energy source 2650 is configured and/or controlled such that the focused energy beams 2655 define a delivery pathway P within the ocular tissue having a depth of between about 600 µm and about 1400 µm.

The energy source 2650 can be any suitable energy source that produces and/or delivers the focused energy beam 2655. For example in some embodiments, the energy source 2650 can include one or more electrodes configured to produce an electrical energy beam. In other embodiments, an electrode can produce a beam of magnetic energy. In other embodiments, the energy source 2650 can include one or more light-emitting devices (e.g., lasers, light-emitting diodes, or the like) configured to produce a beam of light energy. Such a light emitting devices can be configured to produce an energy beam at any suitable frequency for defining the delivery pathway P. For example, some embodiments, the energy source 2650 can produce a non-visible beam of electromagnetic energy (e.g., ultraviolet radiation). In some embodiments, the energy source 2650 can produce a beam of heat (or infrared) energy. In yet other embodiments, the energy source 2650 can include one or more acoustic energy devices (e.g., piezo-electric crystals) configured to produce a beam of acoustic energy (sonic energy, ultrasonic energy, or the like).

Although the energy source 2650 is shown and described coupled to or a portion of the hub 2600, in other embodiments, the energy source 2650 can be included in any portion of the device 2000. For example, in some embodiments, the energy source 2650 can be included in a stand-alone housing through which the barrel 2130 and/or the hub 2600 are disposed. For example, in some embodiments, the energy source 2650 can be included in an engagement member, such as the engagement member 12280 (or any other engagement member) shown and described in U.S. Pat. No. 9,180,047, entitled "APPARATUS AND METHODS FOR OCULAR INJECTION," which is incorporated herein by reference in its entirety.

After the delivery pathway P has been formed, the medicament M can be delivered to the targeted tissue via the delivery pathway P. For example, in some embodiments, the hub 2600 is placed in contact with the surface of the eye S to allow the outer surface 2602 of the hub 2600 to form a substantially fluid-tight seal with a surface of the eye S. More particular, the outer surface 2602 forms a substantially fluid-tight seal with a target surface around the delivery pathway P to limit the amount of leakage of medicament M during application. The outer surface 2602 of the hub 2600 can be any suitable shape, size, and/or configuration and can be configured to contact a portion of the ocular tissue during an application event. For example, as shown in FIG. 10, the outer surface 2602 has a convex distal end surface, which is configured to contact a target surface of a target tissue when a medicament M is conveyed through the opening 2625 into the target tissue. In some embodiments, the outer surface 2602 includes a sealing portion (not shown in the FIGS.) configured to define a substantially fluid-tight seal with the target surface when the outer surface 2602 is in contact with the target surface. For example, the outer surface 2602 can deform the target surface such that the sealing portion is contiguous with the target surface and forms the substantially fluid-tight seal.

In some embodiments, the outer surface 2602 can be formed from a material or combination of materials that is/are relatively flexible and/or that has/have a relatively low durometer. In some embodiments, the outer surface 2602 can be formed from a material with a durometer that is sufficiently low to limit and/or prevent damage to the ocular tissue when placed in contact therewith. In some embodiments, the outer surface 2602 can be configured to deform (e.g., elastically or plastically) when placed in contact with the ocular tissue. In other embodiments, the outer surface 2602 can be formed from a material of sufficient hardness such that the target tissue (and not the outer surface 2602) is deformed when the outer surface 2602 is placed in contact with and/or pressed against the target tissue. In some embodiments, for example, the outer surface 2602 is constructed from a medical grade stainless steel, and has a surface finish of less than about 1.6 µm Ra. In this manner, the surface finish can facilitate the formation of a substantially fluid-tight seal between the outer surface 2602 and the target tissue.

In some embodiments, the delivery device includes a controller (not shown in the FIGS.) that can control the application of focused energy beams 2655 conveyed from the energy source 2650 to create the delivery pathway P. In this manner, the medicament delivery device 2000 can actively control the penetration depth of the focused energy beams 2655 exiting the hub 2600. In such embodiments, the controller can include a memory, a processor, and an input/output module (or interface). The controller can be coupled to a computer or other input/output device via the input/output module (or interface).

The processor (and any of the processors described herein) can be any processor configured to, for example, write data into and read data from the memory of the controller, and execute the instructions and/or methods stored within the memory. Furthermore, the processor can be configured to control operation of the other modules within the controller. Specifically, the processor can receive a signal including user input, distance measurements or the like and determine the amount of focused energy beams to deliver, the desired timing and the like. In other embodiments, the processor (and any of the processors described herein) can be, for example, an application-specific integrated circuit (ASIC) or a combination of ASICs, which are designed to perform one or more specific functions. In yet other embodiments, the microprocessor can be an analog or digital circuit, or a combination of multiple circuits.

The memory device of the controller (and any of the memory devices described herein) can be any suitable device such as, for example, a read only memory (ROM) component, a random access memory (RAM) component, electronically programmable read only memory (EPROM), erasable electronically programmable read only memory (EEPROM), registers, cache memory, and/or flash memory.

In some embodiments, a method includes actuating an energy source from a medicament delivery device to the surface of an eye to deliver one or more focused energy beams having a prescribed focal depth to produce a delivery pathway to a targeted ocular tissue. A medicament is then delivered from the medicament delivery device to the targeted ocular tissue via the delivery pathway. This method is shown schematically in FIGS. 9 and 10, which illustrate a portion of the medicament delivery device 2000 applying focused energy beams 2655 via an energy source 2650 to and/or below the surface of an eye S, and then delivering a medicament to a targeted tissue in the eye (e.g., the suprachoroidal space 36) through the delivery pathway P. Although shown as being performed using the medicament delivery device 2000, in other embodiments, the method can be performed using any suitable device. The method includes moving an outer surface 2602 of a hub 2600 of a medicament delivery device 2000 above a surface S of an eye. In some embodiments, the hub 2600 and/or the energy source 2650 can be maintained at predetermined distance from the surface S by any suitable mechanism. In some embodiments, for example, the device 2000 can include a guide member or housing (not shown) to assist the user in positioning the energy source 2650 and/or the hub 2600.

The method includes applying focused energy beams 2655 to the eye to form a delivery pathway P within and/or to a targeted tissue. In some embodiments, the focused energy beams 2655 have a prescribed focal depth, which produces a delivery pathway P through the conjunctiva 45 and the sclera 20 to reach the targeted tissue, such as the suprachoroidal space 36. After the delivery pathway P is defined, the outer surface 2602 of the hub 2600 is placed in contact with the surface S of the eye, and the medicament is delivered via the pathway P. Specifically, the medicament delivery device 2000 is then actuated to cause a medicament to be expelled from a barrel 2130 of the device through an opening 2625 defined by the inner surface 2601 of the hub 2600. In this manner, the medicament M can reach and/or define the suprachoroidal space 36 between the sclera 20 and the choroid 28.

In some embodiments, the hub 2600 is contacted with the surface S to form a substantially fluid-tight seal with the surface of the eye, as described above.

In some embodiments, the method includes defining, via a focused energy beam, a delivery pathway within the ocular tissue that reaches, but does not extend significantly deeper than, the suprachoroidal space 36. In some embodiments, the energy source is configured such that the focused energy beam defines a delivery pathway within the ocular tissue having a depth of between about 800 µm and about 1200 µm. In other embodiments, the energy source is configured such that the focused energy beam defines a delivery pathway within the ocular tissue having a depth of between about 600 µm and about 1400 µm.

The medicament delivery device 2000 can also be configured to remove a substance from a targeted tissue. In some embodiments, the medicament delivery device 2000 can form a pathway in a tissue as described above and then the outer surface 2602 of the hub 2600 of the medicament delivery device 2000 can be placed in contact with the surface of the tissue and the device can be configured such that a substance can be forced into the opening 2625 of the hub 2600 via a vacuum. The vacuum can be produced with the elastomeric member 2155 and the piston 2150 within the barrel 2130 of the medicament delivery device 2000.

Figure 11A:
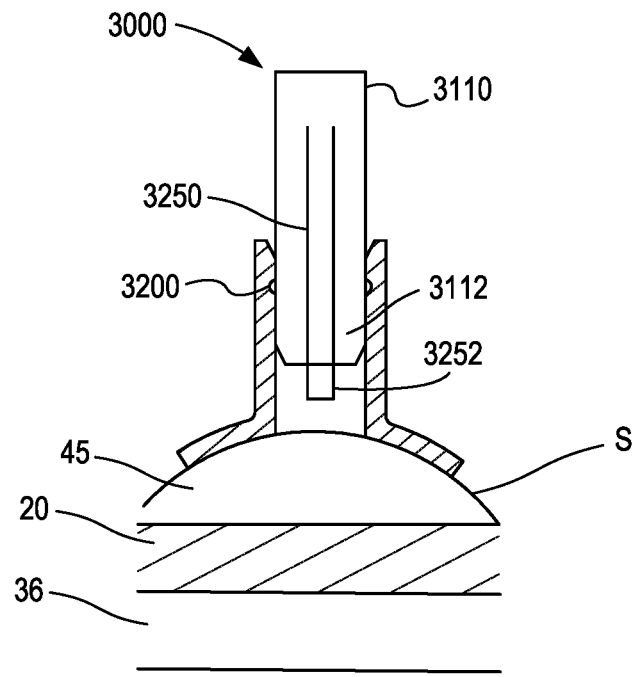
FIGS. 11A and 11B are cross-sectional schematic illustrations of a medicament delivery device according to an embodiment in a first configuration and a second configuration, respectively.
Figure 11B:
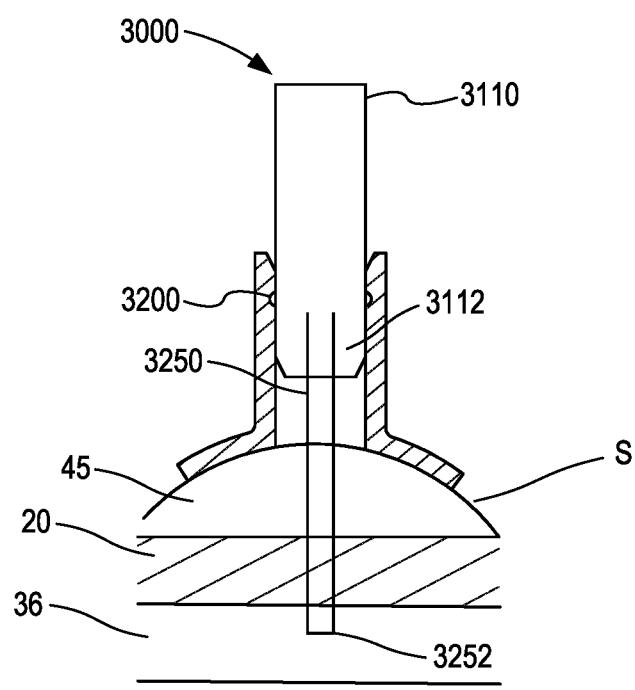

Although the jet injection device 1000 and the medicament delivery device 2000 are shown and described above as including mechanisms that define a delivery pathway to the desired region of tissue (e.g., the suprachoroidal space) without disposing a rigid member (e.g., a needle, a trocar or the like) within the tissue, in other embodiments, a medicament delivery device can define a delivery pathway and/or deliver a drug using a rigid member. For example, in some embodiments, a device can include a rigid member that is temporarily embedded or disposed within the tissue, and that defines at least a portion of a delivery pathway through which a drug can be delivered. Moreover, in some embodiments, a device can include a delivery member that also includes the drug compound to be delivered. For example, FIGS. 11A and 11B show various cross-sectional views of a medicament delivery device 3000 in a first configuration and a second configuration, respectively. The medicament delivery device includes a housing 3110 and a rigid member 3250 according to an embodiment. The rigid member 3250 has a distal end portion 3252 that is coated with a medicament.

Figure 12:
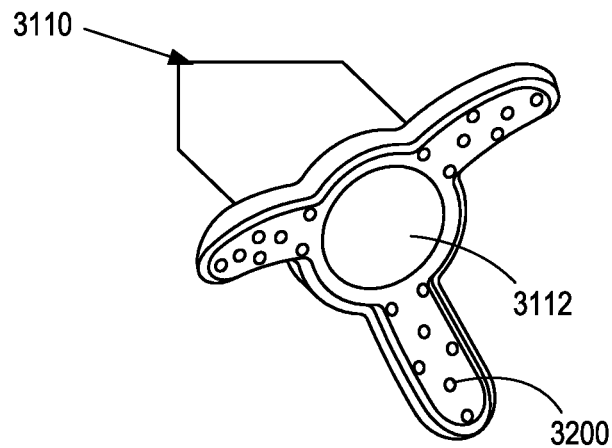
FIG. 12 is a perspective view of a portion of the medicament delivery device shown in FIGS. 11A and 11B.

As shown in FIGS. 11A and 11B, the housing 3110 has a distal end portion 3112 and contains a rigid member 3250. The housing 3110 defines an opening within which the rigid member 3250 can be disposed or moved. The housing 3110 can be a monolithic housing or can include two or more portions, which can be joined together to form the housing 3110. For example, in some embodiments, the housing 3110 can include one or more contact members 3200 at the distal end portion 3112 of the housing 3110. As shown in FIG. 12, each of the contact members 3200 has a surface that can includes an inverse-dimpled or "beaded" traction pattern. The contact members 3200 are configured to contact a surface of the target tissue (e.g., the conjunctiva of the eye) during use to facilitate insertion of a rigid member 3250. The contact members 3200 can be any suitable structure configured to engage the target tissue (as described herein). For example, in some embodiments, the contact members 3200 can be any suitable structure configured to grip, hold, and/or deform a portion of the target tissue (e.g., the conjunctiva of the eye). As shown, at least a portion of the contact members 3200 has a curved shape. The curved shape, for example, can be such that the contact members 3200 are configured to contact a portion of the eye (e.g., the conjunctiva) along a line tangent to a portion of the contact members 3200. Further to this example, the curved shape of the portion of the contact members 3200 can allow for a desired distribution of force(s) to be applied to a portion of the eye.

The rigid member 3250 has a distal end portion 3252 and is configured to move within the housing 3110 in response to a force. When a force is exerted on the rigid member 3250, a distal end portion 3252 of the rigid member 3250 extends beyond the distal end portion 3112 of the housing 3110 and into a targeted tissue. The distal end portion 3252 of the rigid member 3250 is coated with a medicament. The medicament can include any of the drugs herein. When the distal end portion 3252 of the rigid member 3250 extends into a targeted tissue, the medicament is delivered to that tissue. The medicament can be formulated to dissolve after being inserted into bodily tissue.

In some embodiments, the distal end portion 3252 can include an agent that facilitates dissolution of the medicament and/or transportation of the medicament within the tissue. For example, in some embodiments, the distal end portion 3252 includes an enzyme formulated to facilitate migration and/or transportation of the medicament within the eye. Specifically, the distal end portion 3252 can include collagenase, which is formulated to break the peptide bonds in the collagen of the sclera to promote transport of the medicament within the eye.

In some embodiments, a method includes delivery of a medicament by placing a rigid member into a targeted tissue. The method, which is shown schematically in FIGS. 11A and 11B, includes placing the distal end portion 3112 of a housing 3112 of a medicament delivery device 3000 is into contact with a surface of the eye S. A rigid member 3250 is moved within the housing 3110 in response to a force such that a distal end portion 3252 of the rigid member 3250 is placed in the targeted tissue of the eye (e.g., within the suprachoroidal space 36) for delivery of a medicament to the targeted tissue (see FIG. 11B). The rigid member 3250 is maintained in place for a sufficient amount of time to allow delivery of the medicament from the surface of the rigid member to the targeted tissue.

In some embodiments, a practitioner can remove the rigid member 3250 from the housing 3110 and leave the rigid member 3250 in the targeted tissue for a period of time to allow transfer of the medicament from the surface of the rigid member 3250 to the targeted tissue. In this manner, the rigid member 3250 can be a "leave behind" device for a short duration of time (e.g., about 30 minutes, about 1 hour, about 2 hours, and/or less than about 5 hours).

In other embodiments, the rigid member 3250 can be made from a material that dissolves in a bodily tissue over time. In such embodiments, after the rigid member 3250 is placed in the targeted tissue, the rigid member 3250 can be detached from the housing 3110 and left in the targeted tissue to dissolve over time. In such embodiments, the medicament can dissolve into the tissue along with the rigid member 3250. A modification of this embodiment is to leave just the distal end portion 3252 of the rigid member 3250 in the targeted tissue to dissolve and withdraw the remaining portion of the rigid member 3250. In such embodiments, the rigid member 3250 can include a perforated portion to facilitate separation of the distal end portion 3252 from the remainder of the rigid member 3250.

Although shown and described as being a rigid member 3250, in other embodiments, the rigid member 3250 can be partially flexible. In such embodiments, a distal end portion 3252 of the rigid member 3250 can be a flexible solid member, e.g., wire, "rope-like" piece, or the like that can bend and or move within the targeted tissue.

In some embodiments, the rigid member 3250 can have a mechanism to control the depth to which the distal end portion 3252 can be inserted in to the tissue. For example, in some embodiments, the rigid member 3250 and/or the housing 3110 can include protrusions, notches, openings or the like to limit the depth to which the distal end portion 3252 can be inserted in to the tissue. In some embodiments, the rigid member 3250 is configured such that the distal end portion 3252 can be disposed to a depth of between about 800 μm and about 1200 μm. In other embodiments, the rigid member 3250 is configured such that the distal end portion 3252 can be disposed to a depth of between about 600 μm and about 1400 μm.

Although the rigid member 3250 is shown as being movable within the housing 3110, in other embodiments, the rigid member 3250 can be fixedly coupled to and/or within the housing 3110.

Although the medicament delivery device 2000 is shown and described above as including an energy source configured to define a delivery pathway, in other embodiments a drug delivery device can include an energy source configured to facilitate transportation of a composition within the target tissue after the initial delivery. For example, in some embodiments, a device can include one or more energy sources that can produce a change (e.g., a localized change) in the target tissue to facilitate dispersion, movement, dissolution and/or transportation of the drug therein. For example, in some embodiments, any of the hubs and/or housings shown and described herein can include any suitable mechanism to facilitate drug dispersion. Moreover, any of the devices shown and described in International Patent Application No. WO2015/19584, entitled "METHOD AND DEVICES FOR TREATING POSTERIOR OCULAR DISORDERS," and U.S. Pat. No. 9,180,047, entitled "APPARATUS AND METHODS FOR OCULAR INFECTION," each of which is incorporated herein by reference in its entirety, can be used to perform the initial delivery of the drug to the target tissue. Thus, any such injectors can be used in conjunction with a device configured to disperse a medicament.

Figure 13:
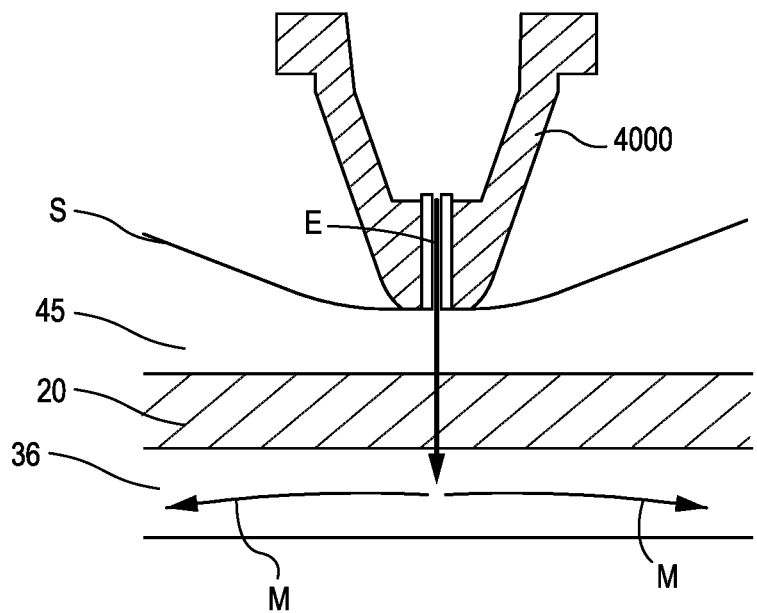
FIG. 13 is a cross-sectional schematic illustration of a medicament delivery device according to an embodiment.

For example, in some embodiments, any of the hubs and/or housings shown and described herein can include an electrode configured to apply a voltage to a surface of the tissue. For example, FIG. 13 shows a schematic illustration of a portion of a device 4000 that includes an electrode through which a voltage or current E is conveyed. Such embodiments can be used, for example, when a medicament is a therapeutic substance within a carrier. Specifically, after the medicament is administered into a suprachoroidal space (or other targeted region) of an eye, applying a voltage or current E to the surface of the tissue using electrodes can be used to release a therapeutic substance from a carrier such as a nanoparticle. In some embodiments, a method can include controlling the rate of delivery of the medicament M by modifying electrical parameters produced by the electrode and formulations of the medicament. Such embodiments can include a single electrode or multiple electrodes. The voltage can be applied in pulses or could be constant depending on the carrier that is being used.

In some embodiments, any of the hubs and/or housings shown and described herein can include an energy source configured to apply high-frequency sound waves (i.e., an ultrasound) to a surface of the tissue. Such embodiments can be used, for example, when a medicament is a therapeutic substance within a carrier. Specifically, after the medicament is administered into a suprachoroidal space (or other targeted region) of an eye, applying the high-frequency sound waves to the surface of the tissue can be used to release a therapeutic substance from a carrier such as a liposome or microbubble. The high-frequency sound waves are applied to a specific targeted area, which minimizes impact on other portions of the body and increases the targeted delivery of the therapeutic substance.

In some embodiments, any of the hubs and/or housings shown and described herein can include an electrode configured to apply an electric current to a surface of the tissue. Such embodiments can be used, for example, when a medicament contains an ionic medicinal compound. Specifically, after the medicament is administered into a suprachoroidal space (or other targeted region) of an eye, applying an electric current to the surface of the tissue using electrodes can be used to move the medicament within the targeted tissue.

In other embodiments, any of the hubs and/or housings shown and described herein can include an energy source that applies a magnetic field to a surface of the tissue. Such embodiments can be used, for example, when a medicament is a therapeutic substance within a carrier that includes magnetic particles (e.g., polymers can contain magnetic particles). Specifically, after the medicament is administered into a suprachoroidal space (or other targeted region) of an eye, applying a magnetic field to the surface of the tissue using electrodes can be used to move the medicament within the targeted tissue.

Figure 14:
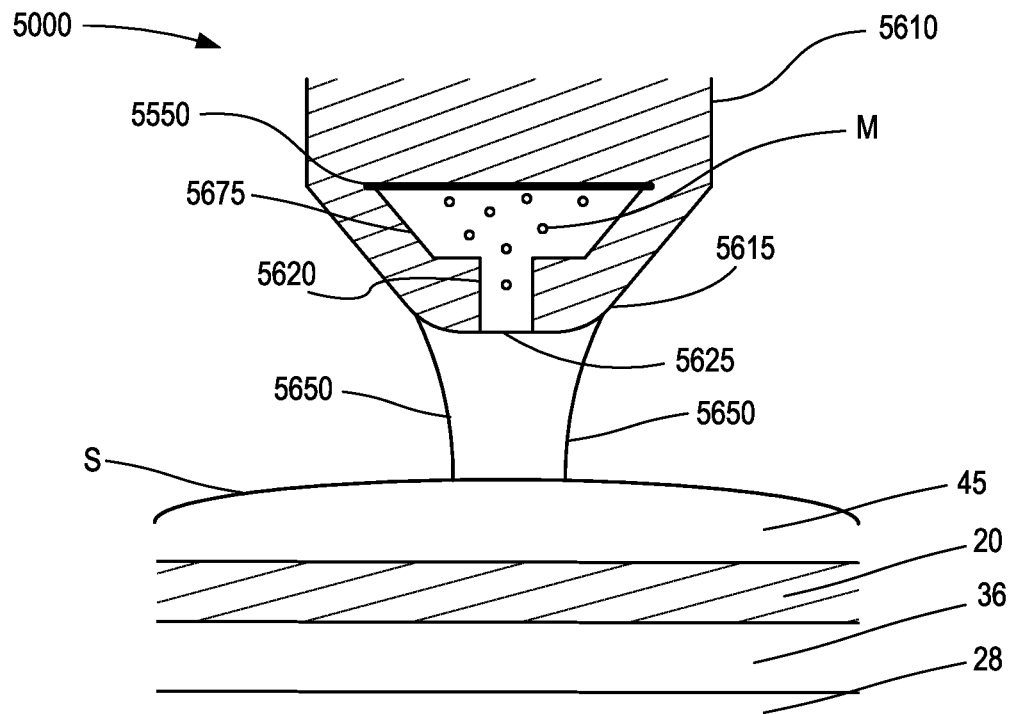
FIG. 14 is a schematic illustration of an iontophoretic apparatus according to an embodiment, in a first configuration.
Figure 15:
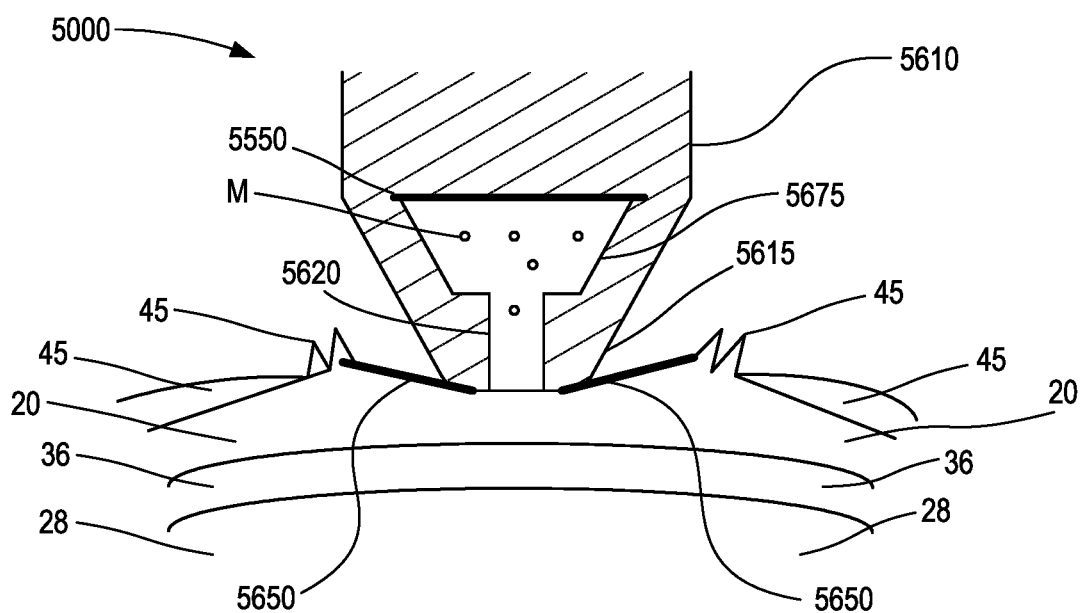
FIG. 15 is a schematic illustration of the iontophoretic apparatus shown in FIG. 14 in a second configuration, after a contact member has moved an outer portion of an eye and a portion of the apparatus is in contact with a sclera of the eye.
Figure 16:
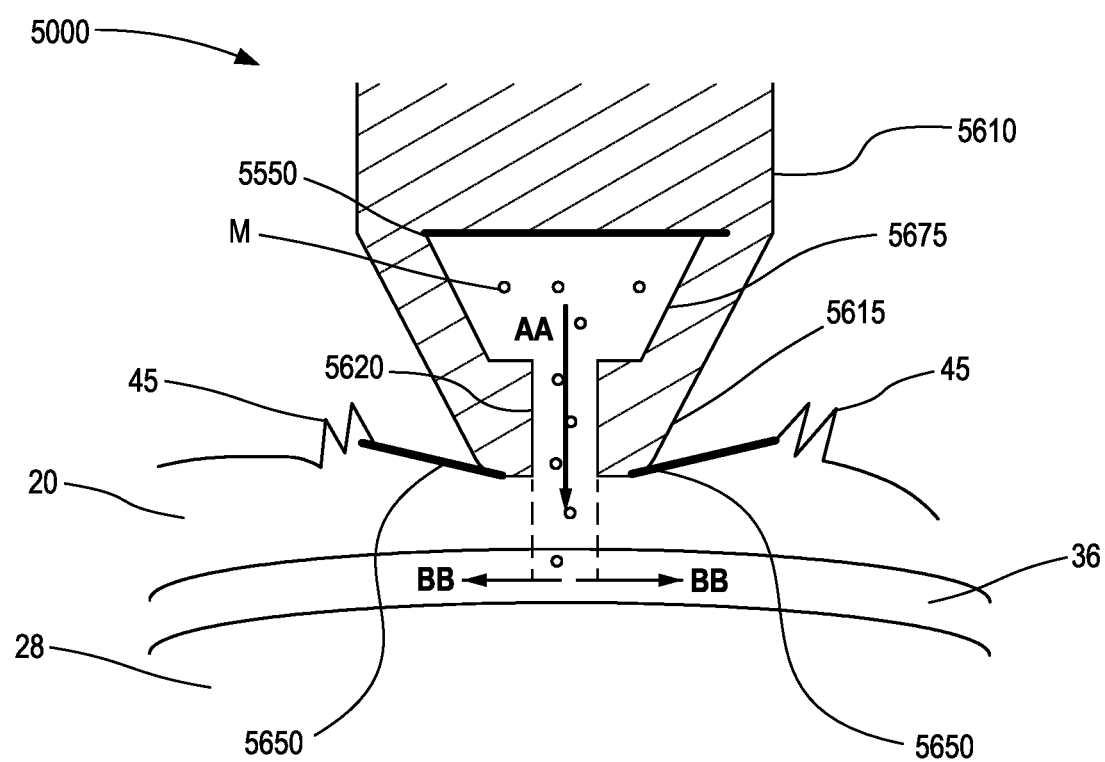
FIG. 16 is a schematic illustration of the iontophoretic apparatus shown in FIGS. 14 and 15 in a third configuration, during which a medicament is being administered through the sclera of the eye into a suprachoroidal space of the eye.

In some embodiments, an apparatus can facilitate targeted delivery of a medicament to a specific region within an eye via iontophoresis. For example, FIGS. 14-16 show various views of a delivery device 5000 (also referred to as an iontophoretic apparatus) according to an embodiment. FIG. 14 shows the delivery device 5000 above the surface S of an eye and spaced apart from the layers of the eye (specifically, the conjunctiva 45, the sclera 20, the suprachoroidal space 36, and the vitreous 28 are shown). The delivery device 5000 includes a housing 5610 and an electrode 5550.

As shown in FIG. 14, the housing 5610 has a distal end portion 5615, a series of contact members 5650, and defines a reservoir 5675. The housing 5610 can be a monolithically constructed housing or it can include two or more separately-formed portions, which can be joined together to form the housing 5610. As shown in FIG. 14, the reservoir 5675 has a proximal end portion and a distal end portion. The proximal end portion of the reservoir 5675 can be coupled to and/or can contain the electrode 5550. The reservoir 5675 can be coupled to the electrode 5550 by any suitable mechanism. For example, in some embodiments, the housing 5610 and/or the reservoir 5675 can include a flange (not shown) that is coupled to the electrode 5550 by a fastening feature (e.g., mounts, notches, grooves, indents, slots, shoulders, or the like). The distal end portion of the housing 5610 forms a closed channel 5620 in fluid communication with the reservoir 5675. The inner walls defining the channel 5620 define an opening 5625.

The reservoir 5675 is configured to contain a medicament M. The medicament M has an ionic charge and can be any suitable drug, medicament or therapeutic agent of the types mentioned herein. For example, in some embodiments, the medicament M can be formulated to include molecules that have a positive or negative charge. In other embodiments, the medicament M can be encapsulated in a carrier that has a positive or negative charge.

The reservoir 5675 can be defined by the housing 5610 or can be any suitable container disposed within the housing 5610 that can receive and/or contain the medicament M. In some embodiments, the reservoir 5675 is made of a material that can hold a positive or negative charge. For example, in some embodiments, the inner walls of the reservoir 5675 can be made of a material that has a charge that is opposite of the charge of the medicament M. In this manner, the charged inner walls retain or "hold" the medicament M within the reservoir 5675. Further, when a charge is produced by the electrode 5550, the charge of the reservoir 5675 can be changed, and the medicament M can be driven out of the reservoir 5675 through the channel 5620 and the opening 5625. For example, if the charge of the inner walls of the reservoir 5675 is changed from a negative charge to a positive charge, a medicament M having a positive charge will be repelled out of the reservoir 5675 through the opening 5625.

Alternatively, some embodiments the housing 5610 can include a membrane (not shown in figures) that covers the opening 5625 of the reservoir 5675. In such embodiments, the membrane is thin enough and/or has a porosity so that the medicament M can pass therethrough. The membrane is also made of a material that has a charge that repels the medicament M, thereby holding the medicament M in the reservoir 5675. When the electrode 5550 produces a charge, the charge of the membrane is altered and the medicament M is released from the reservoir 5675. For example, in some embodiments, the membrane is made of a material that is positively charged, and the medicament M is also positively charged. Thus, the membrane holds the medicament M that is positively charged within the reservoir 5675 because the medicament M is repelled from the membrane. In use, the charge from the electrode 5550 could change the charge of the membrane to a negative charge, which then allows a positively charged medicament M to pass through the membrane and through the opening 5625.

Moreover, the reservoir 5675 can have any suitable volume and/or size. In some embodiments, the volume of the reservoir 5675 can about 0.5 mL or less. In other embodiments, the volume of the reservoir 5675 can be about 0.1 mL or less.

As shown, the electrode 5550 is coupled to the housing 5610 within and/or in contact with the reservoir 5675. The electrode 5550 is configured to produce an electric charge sufficient to convey the medicament M from the reservoir 5675 to a targeted region within an eye. For example, a medicament M that is positively charged would be repelled from the reservoir 5675 when the electrode 5550 produces a positive charge. The charge can have any suitable characteristics. For example, the electrode can produce either a continuous charge or a pulsed charge. Moreover, although shown as being coupled within and/or in contact with the proximal end portion of the reservoir 5674 in other embodiments, the electrode 5550 can be in any suitable orientation and/or position relative to the reservoir 5675.

In some embodiments, the delivery device 5000 can include any number of electrodes configured to produce a charge. For example, in some embodiments, the delivery device 5000 can include a return electrode (not shown) that is coupled to a tissue of the patient and that completes the circuit with the electrode 5550. The return electrode can be coupled to any suitable tissue of the patient, such as the forehead, neck, ear or the like. Further, in some embodiments, the apparatus can include a series of electrodes within and/or coupled to the reservoir 5675 that produce a charge to convey the medicament M, as described herein.

As shown, the delivery device 5000 has one or more contact members 5650 coupled to the distal end portion 5615 of the housing 5610. Although FIG. 14 shows two contact members 5650, the delivery device 5000 can include any number of contact members. The contact member 5650 is configured to separate an outer portion of an eye to define a first pathway through which the distal end portion 5615 of the housing 5610 is disposed. FIG. 14 shows the contact member 5650 coupled to the distal end portion 5615 of the housing 5610. In some embodiments, the contact member 5650 can be movably coupled to the distal end portion 5615 of the housing 5610. FIGS. 14 and 15 show the contact member 5650 in a first position and a second position, respectively. As the contact member 5650 moves from a first position to a second position, the contact member 5650 either moves or cuts a conjunctiva 45 of the eye producing or defining the first pathway through which the distal end portion 5615 of the housing 5610 is disposed.

In this manner, the distal end portion 5615 is placed into contact with a sclera 20 of the eye. By directly contacting the sclera 20, the delivery pathway through which the medicament M travels does not include the conjunctiva 45, which has different characteristics than the sclera 20. For example, the conjunctiva 45 can have a greater permeability than the sclera 20, and thus may absorb substances traveling therethrough. Thus, eliminating the conjunctiva 45 from the delivery pathway can provide more accurate control of the depth to which the medicament M is delivered by the delivery device 5000.

Specifically, FIG. 16 shows the medicament M being expelled from the reservoir 5675 and conveyed through a sclera 20 of an eye as shown by the arrow AA. The charge produced by the electrode 5550 is enough to force the medicament M from the reservoir 5675, through the sclera 20, and into the suprachoroidal space 36 of the eye. Once the medicament M reaches the suprachoroidal space 36 of the eye, the medicament M is dispersed throughout the suprachoroidal space 36 as shown by the arrows BB in FIG. 16.

Figure 17:
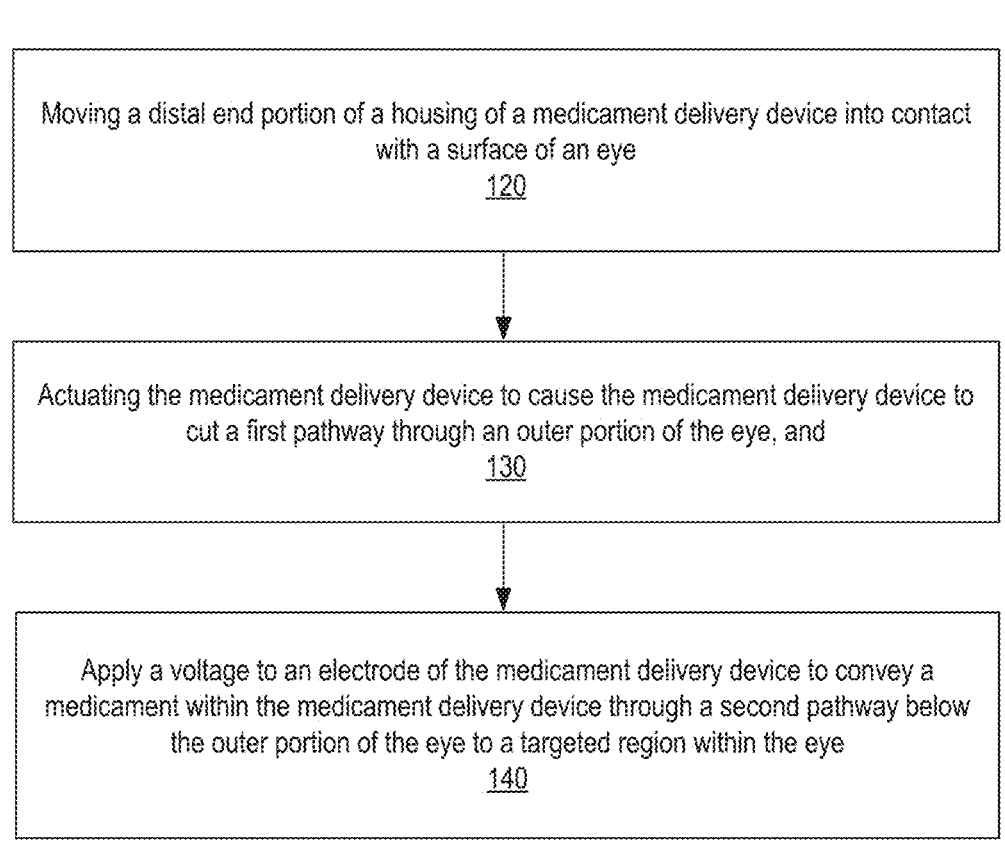
FIG. 17 is a flow chart of a method of conveying a medicament to a targeted region within an eye via an iontophoretic apparatus according to an embodiment.

FIG. 17 is a flow chart that illustrates a method 100 of using an iontophoretic apparatus to deliver a medicament to a targeted region within an eye. In some embodiments, the method includes moving a distal end portion of a housing of a medicament delivery device into contact with a surface of an eye, at 120. The medicament delivery device can be any suitable device of the types shown and described herein, such as, for example, the delivery device 5000. The method further includes actuating the medicament delivery device to cause the medicament delivery device to: A) cut a first pathway through an outer portion of the eye, at 130, and B) apply a voltage to an electrode of the medicament delivery device to convey a medicament within the medicament delivery device through a second pathway below the outer portion of the eye to a targeted region within the eye, at 140.

In some embodiments the delivery device 5000 includes a controller (not shown) that can control the amount, duration, and characteristics of the charge produced by the electrode 5550. In this manner, the delivery device 5000 can actively control the medicament delivery depth of the medicament M exiting the reservoir 5675. For example, in some embodiments, the controller can control the amount, duration, and characteristics of the charge produced by the electrode 5550 to deliver the medicament M to the suprachoroidal space. In some embodiments, the controller can control the amount, duration, and characteristics of the charge produced by the electrode 5550 to deliver the medicament M to a depth of between about 900 μm and about 1100 μm.

In such embodiments, the controller can include a memory, a processor, and an input/output module (or interface). In some embodiments, the controller can also include a feedback module (not shown) that receives a signal from a sensor (not shown). A feedback module includes circuitry, components, and/or code to produce a control signal that can facilitate controlling the amount of charge that is produced by the electrode 5550. The controller can be coupled to a computer (not shown) or other input/output device via the input/output module (or interface).

The processor (and any of the processors described herein) can be any processor configured to, for example, write data into and read data from the memory of the controller, and execute the instructions and/or methods stored within the memory. Furthermore, the processor can be configured to control operation of the other modules within the controller (e.g., the feedback module). Specifically, the processor can receive a signal including user input, distance measurements or the like and determine an amount of charge to be produced by the electrode 5550, the desired timing and sequence of the charge pulses and the like. In other embodiments, the processor (and any of the processors described herein) can be, for example, an application-specific integrated circuit (ASIC) or a combination of ASICs, which are designed to perform one or more specific functions. In yet other embodiments, the microprocessor can be an analog or digital circuit, or a combination of multiple circuits.

The memory device of the controller (and any of the memory devices described herein) can be any suitable device such as, for example, a read only memory (ROM) component, a random access memory (RAM) component, electronically programmable read only memory (EPROM), erasable electronically programmable read only memory (EEPROM), registers, cache memory, and/or flash memory. Any of the modules (the feedback module) can be implemented by the processor and/or stored within the memory.

Although the delivery device 5000 is shown as including one or more separate, movable contact members 5650, in other embodiments, the distal end portion 5615 can include a contact portion, cutting portion, or the like that is configured to cut, separate and/or move an outer portion of an eye. For example, in some embodiments, the distal end portion 5615 can include a sharp edge or blade that cuts and moves the conjunctiva 45 to allow contact between the sclera 20 and the distal end portion 5615.

Figure 18:
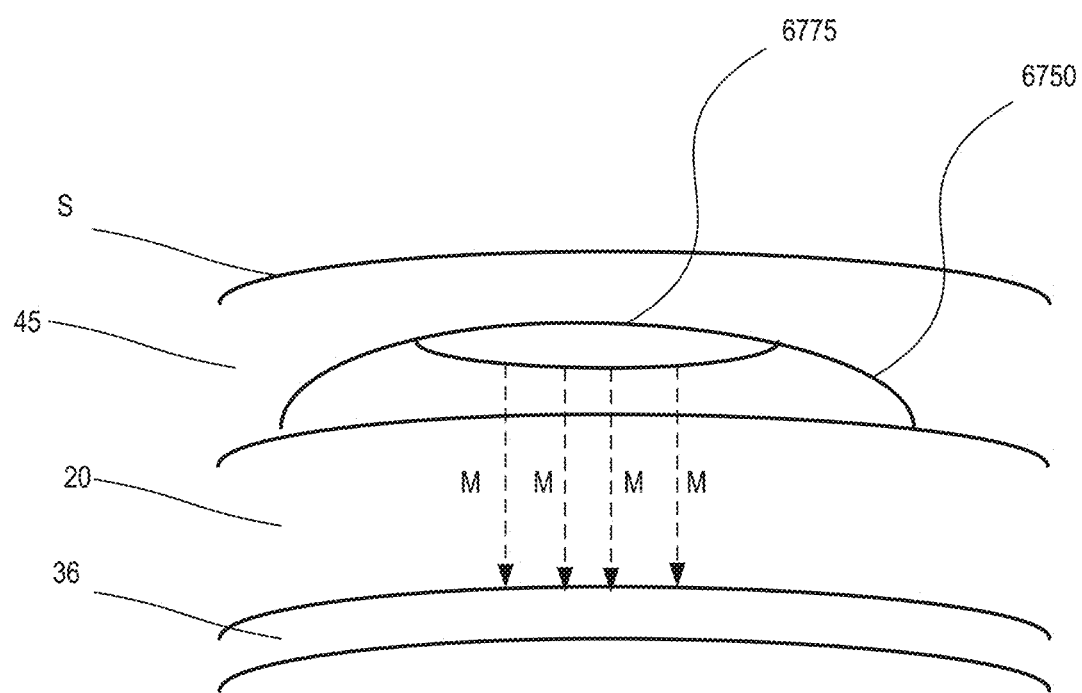
FIG. 18 is a schematic illustration of a medicament delivery membrane according to an embodiment.

Although the delivery device 5000 is shown as including one or more separate, movable contact members 5650 that cut, separate and/or move an outer portion of the eye, in other embodiments, an iontophoretic delivery device can define a delivery pathway that includes the outer surface (e.g., the conjunctiva). For example, in some embodiments, an apparatus includes a housing, an electrode and a controller. The housing has a distal end portion that is configured to contact a surface of an eye. The housing defines a reservoir that is configured to contain a medicament having an ionic charge. The electrode is coupled to the housing. The electrode is configured to produce a charge that is sufficient to convey the medicament from the reservoir to a targeted region within the eye. The controller is configured to adjust the charge to convey the medicament to a medicament delivery depth within a predetermined range. Although the delivery device 5000 is shown and described above as including a housing 5610 and an electrode 5550 disposed outside of the eye that convey a medicament M to a targeted region within an eye, in other embodiments, a medicament delivery membrane can be placed within the eye and used to convey the medicament M to a targeted region within the eye. For example, in some embodiments, a medicament delivery membrane can be configured to be disposed within an eye and can include a reservoir through which a drug can be delivered. FIG. 18 shows a medicament delivery membrane 6750, which includes a reservoir 6775 containing a medicament M. The medicament delivery membrane 6750 is placed below a surface S of an eye, between a conjunctiva 45 and a sclera 20 of the eye. In some embodiments, the reservoir 6775 is configured to allow a medicament to diffuse over time into a targeted region within the eye. FIG. 18 shows a medicament M diffusing from the reservoir 6775, through a sclera 20, and into a suprachoroidal space 36 (see arrows labeled M).

In some embodiments, the medicament delivery membrane 6750 is made of a material that is formulated to degrade over time. Thus, the membrane 6750 can be a "leave behind" device for which later removal is not necessary. In other embodiments, the medicament delivery membrane 6750 can be removed after a period of time. In some embodiments, the reservoir 6775 is configured to be refilled with a medicament M when the medicament delivery membrane 6750 is disposed between the conjunctiva 45 and the sclera 20. For example, in some embodiments, the membrane can include a port (not shown) that can be accessed through the conjunctiva to facilitate refilling the reservoir. In such an embodiment, the medicament delivery membrane can stay in place for an indefinite amount of time to direct a medicament to a targeted region within an eye.

Additionally, in some embodiments, the medicament delivery membrane can be coupled with a flexible thin film battery (not shown in figures). The thin film battery is configured to produce a charge sufficient to convey the medicament from the reservoir into a targeted region within an eye via iontophoresis. For example, in some embodiments an ocular deliver membrane can include a flexible, thin electrochemical cell that can produce the electric current and/or charge to convey the medicament into a targeted region within the eye. In some embodiments, a membrane can include a thin, printed power source such as the types produced by Power Paper Ltd.

Figure 19:
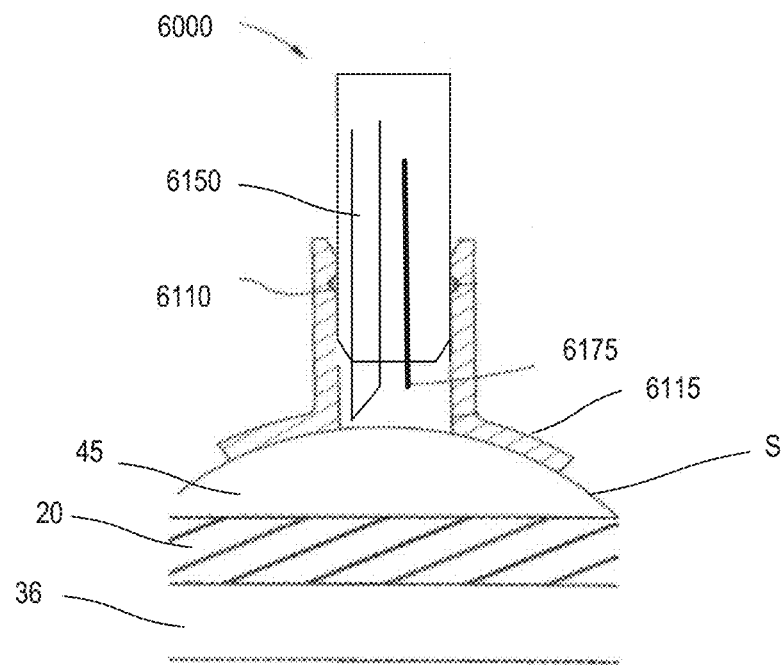
FIG. 19 is a schematic illustration of a medicament delivery device, according to an embodiment, configured to deliver a medicament delivery membrane into an eye.
Figure 20:
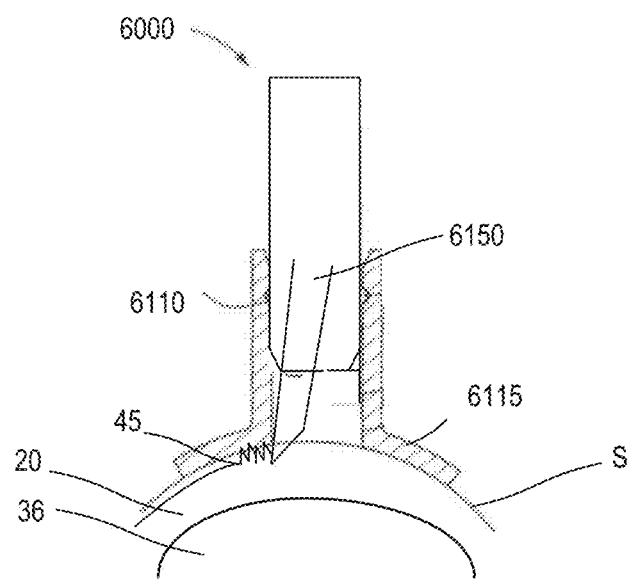
FIGS. 20 and 21 show the medicament delivery device depicted in FIG. 19 in various stages of operation.
Figure 21:
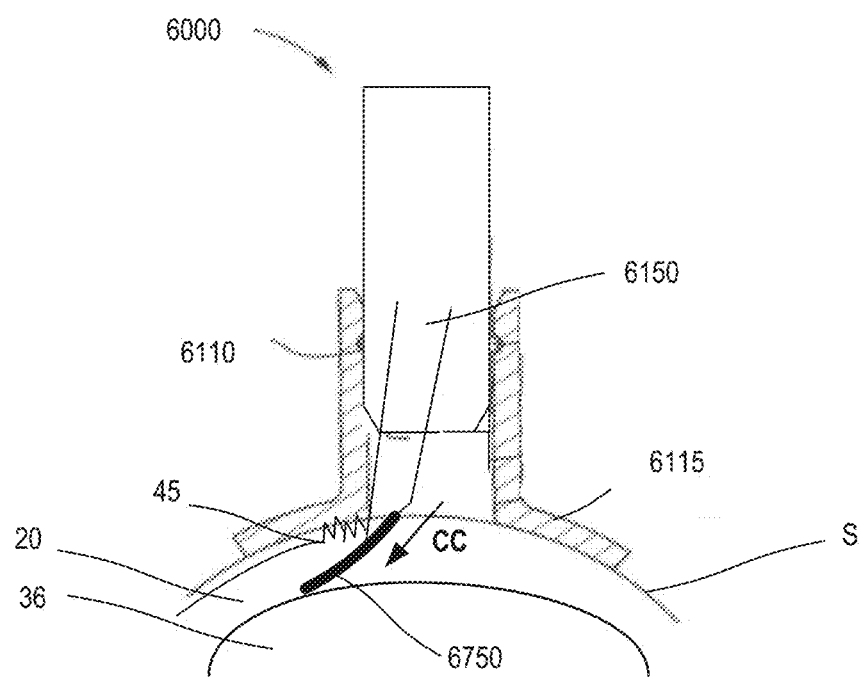

In some embodiments, a medicament delivery membrane can be delivered using a medicament delivery device that produces a pathway through a conjunctiva and disposes the medicament delivery membrane between the conjunctiva and a sclera of an eye. For example, FIGS. 19-21 show a medicament delivery device 6000 used to deliver a medicament delivery membrane 6750, or any other membranes described herein. FIGS. 19-21 show the medicament delivery device 6000 in various configurations or "stages" of operation. As shown, the medicament delivery device 6000 includes a housing 6110, a contact member 6150, and a delivery member 6175. FIG. 19 shows the housing 6110 having a distal end portion 6115, which is placed on a surface S of an eye. As shown, the layers of the eye (conjunctiva 45, sclera 20, and suprachoroidal space 36) are intact.

The contact member 6150 is movably disposed within the housing 6110. The contact member 6150 can extend beyond the distal end portion 6115 of the housing 6110 and is configured to separate an outer portion of the eye to define a pathway. FIGS. 19 and 20 show the contact member 6150 in a first position and a second position, respectively. As the contact member 6150 moves from a first position to a second position, the contact member 6150 either moves or cuts a conjunctiva 45 of the eye producing or defining a pathway. The contact member 6150 can be rigid (e.g., a blade) or flexible.

The delivery member 6175 is movably disposed within one of the housing 6110 or the contact member 6150. The delivery member 6175 is configured to convey a medicament delivery membrane through the pathway produced or defined by the contact member 6150. The delivery membrane 6175 is also configured to position the medicament delivery membrane on a surface of a sclera of an eye. In some embodiments, the delivery membrane 6175 is a plunger. In some embodiments, the delivery membrane 6175 is removably coupled to the medicament delivery membrane such that upon delivery the medicament delivery membrane releases from the delivery member 6175 and is placed within the eye.

In use, the delivery device 6000 can deliver the medicament delivery membrane 6750 using methods according to an embodiment, as shown in FIGS. 20 and 21. FIG. 19 shows the delivery device 6000 in a first (or ready) configuration, with the distal end portion 6115 in contact with an eye. FIG. 20 shows the medicament delivery device 6000 in a second configuration as the contact member 6150 produces a pathway through a conjunctiva 45 of the eye. The distal end portion 6115 of the housing 6110 provides positioning support for the medicament delivery device 6000 on the surface S of an eye. The contact member 6150 then produces a pathway through the conjunctiva 45 by either cutting the conjunctiva 45 or moving the conjunctiva 45 to the side. FIG. 20 shows the conjunctiva 45 bunched up as the contact member 6150 moves relative to the housing 6110 to produce the pathway to a sclera 20.

After the medicament delivery device 6000 defines a pathway through the conjunctiva 45, a medicament delivery membrane 6750 can be delivered to a surface of the sclera 20 as shown by the arrow labeled CC in FIG. 21. More particularly, the medicament delivery membrane 6750 can be delivered via a delivery member 6175 (the delivery member 6175 shown in FIG. 19 but not shown in FIGS. 20 and 21), which is movably disposed within one of the housing 6110 or the contact member 6150. FIG. 21 shows the medicament delivery membrane 6750 being delivered via the contact member 6150 as the delivery member 6175 moves within or relative to the contact member 6150.

Although the medicament delivery device 6000 is shown as including a contact member 6150 that defines a pathway and a delivery member 6175 that moves the membrane through the pathway, in other embodiments, a medicament delivery device can include a cannula. The cannula can contain a needle (or trocar) that moves therein and that can pierce, separate and/or cut the conjunctiva. In other embodiments, a medicament delivery device can include any suitable mechanisms for defining the pathway and/or conveying a membrane through the pathway to a region within the eye.

For example, in some embodiments, the medicament delivery device 6000 does not contain a contact member. In these embodiments, a distal end portion of the housing creates a pathway through a conjunctiva of an eye.

Although the medicament delivery device 6000 is shown and described as defining a pathway through the conjunctiva (through which the membrane 6750 is disposed), in other embodiments, the medicament delivery device 6000 can produce a pathway within any portion of the eye, including the conjunctiva, the sclera, the choroid, or any other region. For example, in some embodiments, the medicament delivery membrane 6750 can be disposed within the SCS. In other embodiments, the medicament delivery membrane 6750 can be disposed within the subretinal space. In yet other embodiments, the medicament delivery membrane 6750 can be disposed within the sclera or the vitreous. In yet other embodiments, the medicament delivery device 6000 can produce a pathway within any tissue of the body, including the skin.

Figure 22:
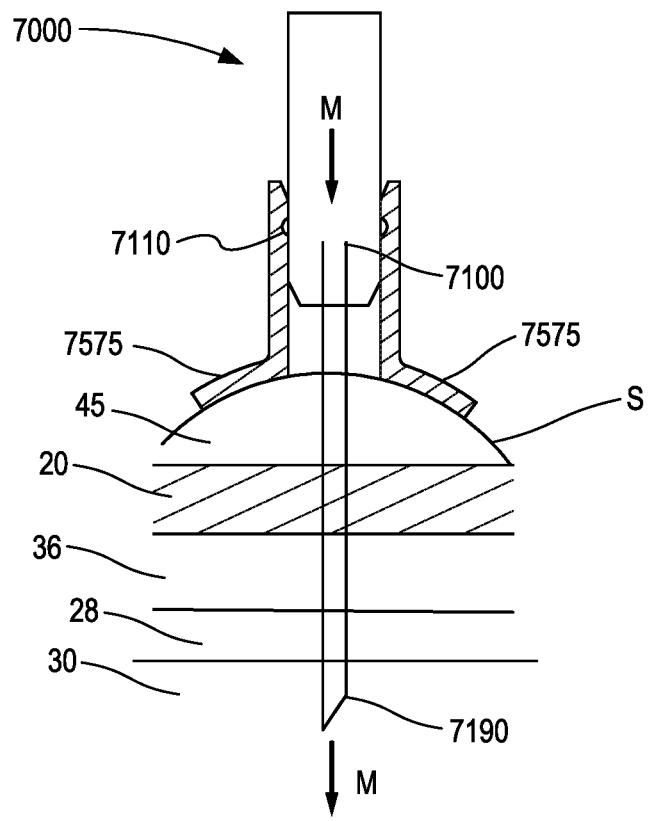
FIGS. 22 and 23 are schematic illustrations of a medicament delivery apparatus according to an embodiment, in a first configuration and a second configuration, respectively.
Figure 23:
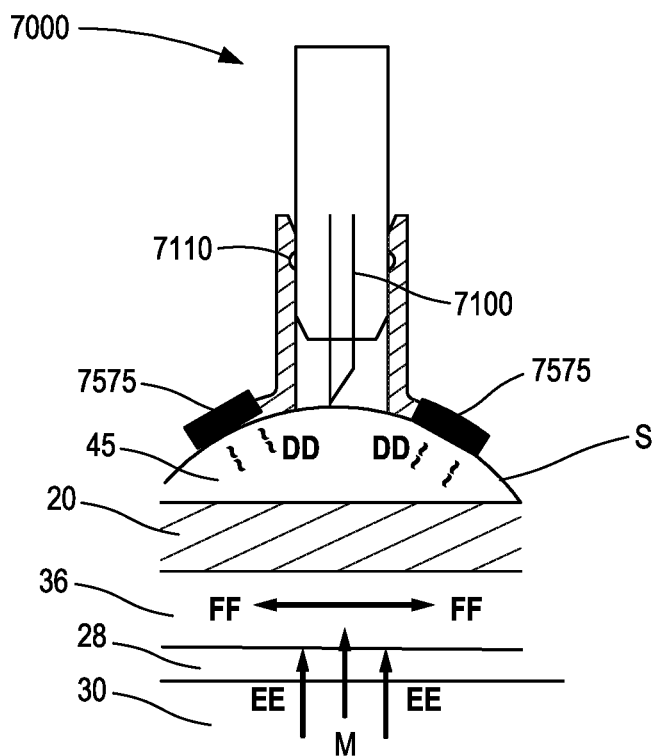

Although the embodiments of the medicament delivery device 6000 are configured to define a delivery pathway from the exterior of the eye to a targeted region therein, in other embodiments a medicament delivery device can include an energy source configured to facilitate transportation of a composition to a target tissue from the interior of the eye. For example, in some embodiments, a medicament can be initially delivered into a vitreous of an eye, and then conveyed to the suprachoroidal space, the subretinal space, or any other suitable region within the eye. FIGS. 22 and 23 show a device and method using this alternative approach for delivering a medicament to a targeted region in an eye. In some embodiments, the method can be performed using the medicament delivery device 7000. The medicament delivery device 7000 includes a housing 7110 and an injector 7100. The injector 7100 can be movably disposed within the housing 7110, and can use a needle 7190 to inject a medicament M into a vitreous 30 of an eye. The injector 7100 can be any of the devices shown and described in International Patent Application No. WO2015/19584, entitled "METHOD AND DEVICES FOR TREATING POSTERIOR OCULAR DISORDERS," and U.S. Pat. No. 9,180,047, entitled "APPARATUS AND METHODS FOR OCULAR INFECTION," each of which is incorporated herein by reference in its entirety. Thus, any such injectors can be used in conjunction with a device configured to disperse a medicament.

FIG. 22 shows the housing 7110, which defines a channel within which the injector 7100 and/or a medicament container containing a medicament M can be moved. The housing 7110 has a distal end portion coupled to an energy source 7575. The energy source 7575 is any suitable energy source that causes the medicament to move from the vitreous of the eye to a targeted region within the eye. For example, in some embodiments, the energy source 7575 can be a magnetic plate that can produce a magnetic field or an electrode that can produce a charge. In use, the energy source 7575 is placed on the surface S of the eye. The injector 7100 and the needle 7190 are moved to penetrate several layers of the eye (conjunctiva 45, sclera 20, suprachoroidal space 36, and choroid 28) to reach the vitreous 30. Once the needle 7190 reaches the vitreous 30, the medicament M is delivered to the vitreous (shown by the arrow labeled M in FIG. 22).

FIG. 23 shows the medicament delivery device 7000 after the medicament M is deposited in the vitreous 30. At this point, the energy source 7575 of the medicament delivery device 7000 is activated (shown by the lines DD in FIG. 23) causing the medicament to travel from the vitreous 30 toward the energy source 7575 (shown by the arrows EE). The medicament is then dispersed through the targeted region of the eye, such as the suprachoroidal space 36, as shown by the arrows FF in FIG. 23. In some embodiments, the medicament can be dispersed into any suitable region, such as the subretinal space.

In some embodiments, the medicament M is tethered to or encapsulated in magnetic particles or nanospheres. In such embodiments, the energy source 7575 is a magnetic plate that can produce a magnetic field to attract the medicament M to cause the medicament M to travel from the vitreous 30 toward the surface S of the eye. The magnetic field is produced long enough and/or with the desired intensity and/or direction to deliver the medicament M to a targeted region of the eye (e.g., the suprachoroidal space 36). The magnetic field can be applied in pulses or could be constant depending on the carrier that is being used.

In other embodiments, the medicament M can have an ionic charge. In such embodiments, the energy source 7575 is an electrode that can produce a charge to attract the medicament M to cause the medicament M to travel from the vitreous 30 toward the surface S of the eye and then within the suprachoroidal space 36, as shown by the arrows FF in FIG. 23. The charge is produced long enough and/or with the desired intensity to deliver the medicament M to a targeted region of the eye (e.g., the suprachoroidal space 36). Such embodiments can include a single electrode or multiple electrodes. The voltage can be applied in pulses or could be constant depending on the carrier that is being used.

In some embodiments, a medicament can be tethered or encapsulated in a carrier, such as a nanoparticle or nanosphere that contains a soluble polymer that can be charged, such as PLA or PGA. In such embodiments, a medicament delivery device injects the medicament into a targeted region of an eye (e.g., the retina or the choroid) and then applies an external energy, such as infrared energy. The wavelength of the external energy travels through the external layers of the eye to bind the medicament to the targeted region of the eye by crosslinking the soluble polymer.

Although the energy source 7575 is shown and described as being an electronic or magnetic energy source, in other embodiments, the energy source can be any suitable energy source. For example, in some embodiments, the energy source can be a pump that applies pressure or suction, a chemical energy source, an energy source that produces iontophoretic motion, an energy source that produces thermophoretic motion, or the like.

Figure 24:
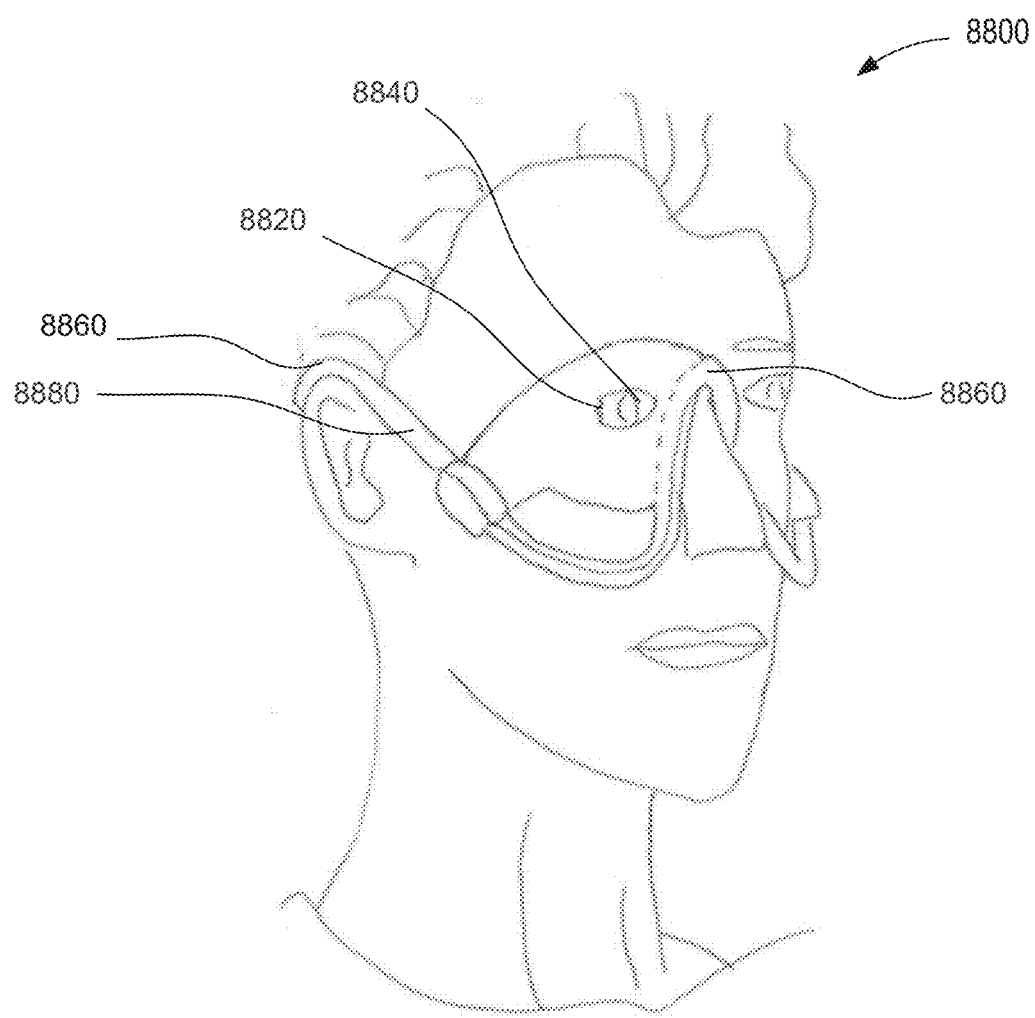
FIG. 24 is a perspective view of an anatomical positioning apparatus according to an embodiment.
Figure 25:
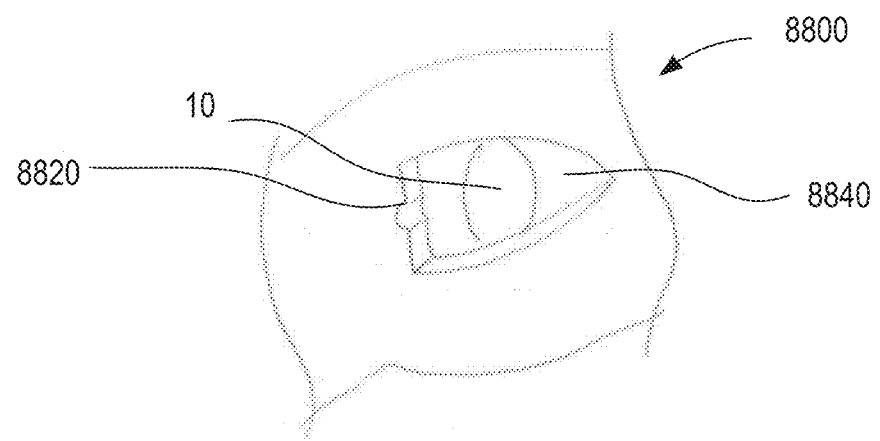
FIG. 25 is a close up view of a portion of the anatomical positioning apparatus shown in FIG. 24.

In some embodiments, an anatomical positioning apparatus is used for ocular drug delivery. The anatomical positioning apparatus provides a template or guide that affixes to or contacts certain anatomical features of a patient's face to ensure proper placement of a needle to facilitate targeted delivery of a medicament to a specific region within an eye. For example, FIGS. 24 and 25 show various views of an anatomical positioning apparatus including a guide member 8800 according to an embodiment. FIG. 24 shows the guide member 8800 affixed to a patient's face. The guide member 8800 is designed to ensure that a puncture member or delivery device (not shown) is inserted at the desired location and/or in the desired orientation relative to the eye. For example, in some embodiments, the guide member 8800 can facilitate insertion that is perpendicular to a tangent line to the surface of the eye. In some embodiments, the guide member 8800 can ensure that the puncture member projects a prescribed length into the eye, thus reaching the proper location within a targeted region within the eye. The puncture member or delivery device can be one of a needle, probe, trocar, cannula, etc. The guide member 8800 includes adjustable members 8880 that allow it to be adjusted to better fit a patient. The guide member 8800 includes at least one index portion 8860 that rests on a key anatomical landmark (e.g., ridge of nose, top of ear, temple, brow) to provide proper placement of the apparatus. When the guide member 8800 is placed on a patient, the side wall 8820 defines an opening 8840 which is above the patient's eye.

FIG. 25 shows a close up view of the side wall 8820 and the opening 8840. In some embodiments, the side wall 8820 receives the puncture member (not shown) to ensure the desired angle of insertion of the puncture member into the eye 10. For example, in some embodiments, the side wall 8820 can be substantially normal to a tangent line to the surface of the eye 10 (i.e., to facilitate perpendicular insertion of the puncture member). In other embodiments, the side wall 8820 can form any suitable angle with a tangent line. For example, in some embodiments, the side wall 8820 can form an angle of between about 60 degrees and 75 degrees. In other embodiments, the side wall 8820 can form an angle of about 45 degrees. In other embodiments, the side wall 8820 can form an angle of between about 30 degrees and 45 degrees. In other embodiments, the side wall 8820 can form an angle of less than about 15 degrees. In some embodiments, the side wall 8820 is configured to receive a portion of a hub of a syringe assembly (not shown). In such embodiments, the hub is configured to house the puncture member.

In some embodiments, the guide member 8800 includes a shoulder (not shown) that is configured to limit the movement of the puncture member relative to the eye. The shoulder provides an end stop for the puncture member, thus limiting the depth of the puncture member within the eye.

In some embodiments, a guide member, such as the guide member 8800, includes a microneedle and medicament container. The medicament container is configured to contain a medicament. When the apparatus is placed over an eye of a patient, the microneedle is inserted into the eye as the apparatus is eased into place on the patient. Once in place, a user causes the medicament to be expelled from the medicament container into a targeted region in the eye.

The guide member 8800 can be of various sizes in order to fit the facial dimensions of a wide range of patients (such as young children, teenagers, adults).

Although the anatomical positioning apparatus is described above as including a guide member to provide guidance of the puncture member to convey a medicament to a targeted region within an eye, in other embodiments, other methods can be used to properly position a delivery apparatus to deliver a medicament to a targeted region within the eye. For example, in some embodiments, a device and/or guide member can facilitate insertion of a needle or puncture member to a desired depth based on a change in density (or loss of resistance) between the layers of the eye. Within the eye, the sclera generally has a higher density than the conjunctiva or the suprachoroidal space. Differences in the density of the target region or layer can produce different backpressure against the puncture member and/or the fluid being delivered therefrom. Thus, in some embodiments, a delivery device can be configured to deliver a medicament to a desired target region based on such physical differences.

For example, in some embodiments, a medicament delivery device includes a puncture member with a closed distal end portion and at least one lateral port. Specifically, as shown in FIGS. 26A-26D, the device 9000 includes a hub 9120 and a needle 9150 (also referred to as a puncture member 9150). The hub 9120 can be any suitable component that fluidically couples a medicament container (not shown) to the needle 9150. For example, the hub 9120 can be coupled to the medicament container (or barrel, not shown) using any suitable coupling features, such as, for example, Luer connectors, threads, snap-fit, latch, lock, friction fit, or any other suitable coupling features. Although the hub 9120 is shown and described as being a separate component from the medicament container, in other embodiments, the container and the hub 9120 can be monolithically constructed. The hub can be any of the hubs shown and described herein and/or in U.S. Pat. No. 9,180,047 entitled "APPARATUS AND METHOD FOR OCULAR INJECTION," the disclosure of which is incorporated herein by reference in its entirety.

Figure 26A:
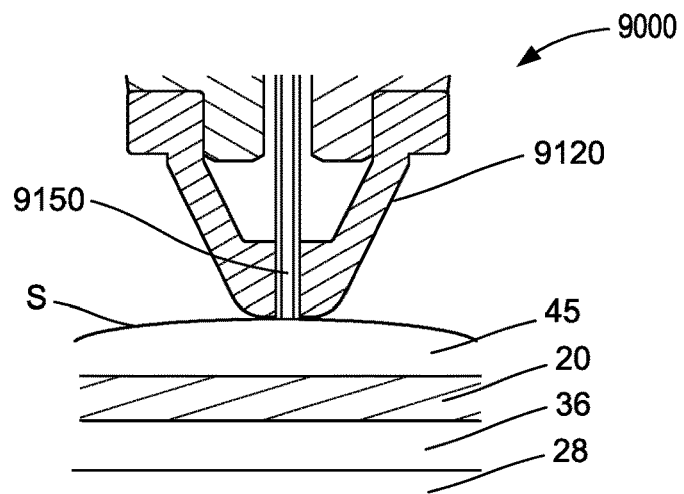
FIGS. 26A-26C are schematic illustrations of a medicament delivery apparatus including a needle with a lateral port in various configurations during which a medicament is being administered through the lateral port of the needle into a suprachoroidal space of the eye.
Figure 26B:
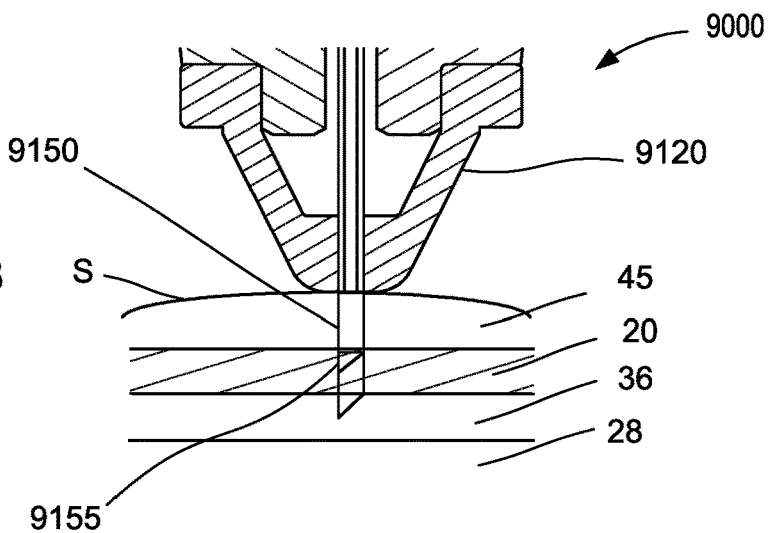
Figure 26C:
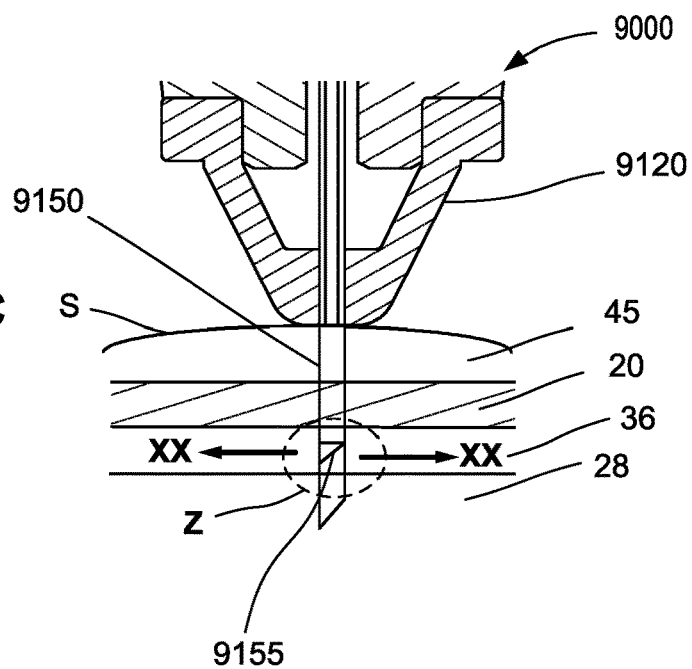

The needle 9150 is housed within the hub 9120 (see, e.g., FIG. 26A) and moves relative to the hub 9120 (see, e.g., FIGS. 26B-26C). The needle 9150 can be any suitable puncture member configured to puncture a target tissue and contains at least one lateral port 9155 (see, e.g., FIGS. 26B-26D). For example, the needle 9150 can be a microneedle configured to puncture ocular tissue. In some embodiments, the needle 9150 can be a 32-gauge microneedle or a 34-gauge microneedle. In some embodiments, the shape and/or size of the needle 9150 can correspond, at least partially, with at least a portion of a target tissue. For example, in some embodiments, the length of the needle 9150 can correspond with a thickness of a portion of ocular tissue such that when the needle 9150 is inserted into the ocular tissue, at least a portion of the needle 9150 is disposed within the sclera 20 or suprachoroidal space 36 of the eye, as described in further detail herein. The needle 9150 defines a lumen that extends through the needle 9150. The distal end portion of the needle 9150 can include a bevel or a sharpened tip configured to puncture a target tissue. Moreover, the distal end portion can be closed such that the medicament flows through the needle and exits the lateral port 9155, as described herein.

Figure 26D:
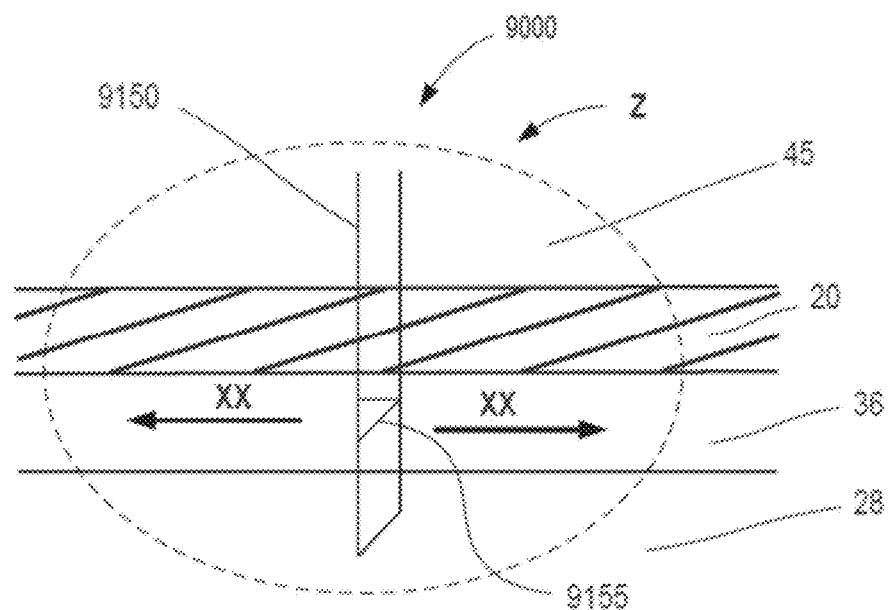
FIG. 26D is a close up schematic illustration of the medicament delivery apparatus shown in FIG. 26C, showing medicament being delivered to a suprachoroidal space of an eye via the lateral port of the needle.

In some embodiments, a method includes conveying a medicament into a desired region via the puncture member 9150 or any other suitable puncture member with one or more lateral ports 9155. FIG. 26A shows a medicament delivery apparatus 9000 in a first configuration having a puncture member 9150 housed within a hub 9120. When the medicament delivery apparatus 9000 moves from its first configuration (FIG. 26A) into a second configuration (FIG. 26B) the puncture member 9150 moves relative to the hub 9120 and is inserted into the eye. As shown in FIG. 26B, when the puncture member 9150 is inserted into the eye, a force having a magnitude less than a threshold value is exerted on an actuation rod (not shown) of the medicament delivery device. As the force is exerted on the actuation rod, if the force is insufficient to overcome the backpressure produced by the tissue, the actuation rod will not move within a medicament container (not shown) of the medicament delivery apparatus. If, however, the force is sufficient to overcome the backpressure produced by the tissue, the actuation rod moves within a medicament container of the medicament delivery apparatus and a medicament will be expelled through a lateral port of a puncture member. Specifically, as shown in FIG. 26B, movement of the actuation rod (not shown) within the medicament container (not shown) is limited if the lateral port of the puncture member is within a region of the tissue where the back pressure is greater than the force applied to the actuation rod (e.g., the sclera, which has a higher density than the suprachoroidal space). However, as depicted in FIGS. 26C and 26D, when the lateral port 9155 of the puncture member 9150 enters the suprachoroidal space, a region of lower density, the actuation rod expels the medicament from the medicament container (not shown) through the puncture member 9150 and out of the lateral port 9155 into the suprachoroidal space, as shown by the arrows XX.

Although the puncture member 9150 is shown in FIGS. 26A-26D moving relative to the hub 9120, in other embodiments the puncture member can be fixedly coupled to the hub. The puncture member can be coupled to the hub using any suitable coupling features, such as, for example, Luer connectors, threads, snap-fit, latch, lock, friction fit, an adhesive, or any other suitable coupling features.

In some embodiments, the puncture member is one of a microneedle, needle, trocar, cannula, or the like, wherein the puncture member defines a hollow interior and does not have an opening at a distal end portion.

In some embodiments, the puncture member is inserted such that the centerline of the delivery passageway and a surface line tangent to a surface of the target tissue defines an angle of entry of between about 75 degrees and about 105 degrees. In some embodiments, the angle of entry is between about 60 degrees and about 75 degrees. In some embodiments, the angle of entry is more than about 45 degrees.

In some embodiments, the force exerted on the actuation rod of the medicament delivery apparatus can be between about 2 N and about 6 N, for example, about 3 N, about 4 N, or about 5 N, inclusive of all ranges therebetween.

Figure 27A:
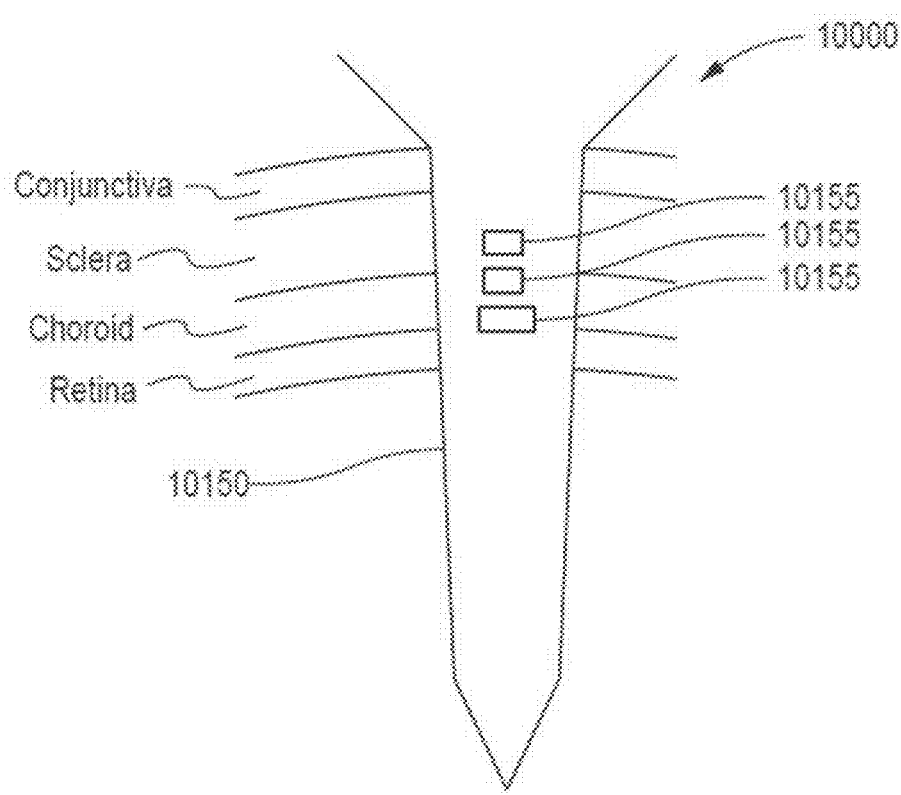
FIG. 27A is a schematic illustration of a medicament delivery apparatus including a needle with multiple lateral ports, according to an embodiment.

In some embodiments, the medicament delivery apparatus has a puncture member that includes multiple lateral ports. For example, FIG. 27A shows a medicament delivery apparatus 10000 that includes three lateral ports 10155 in a needle 10150.

Figure 27B:
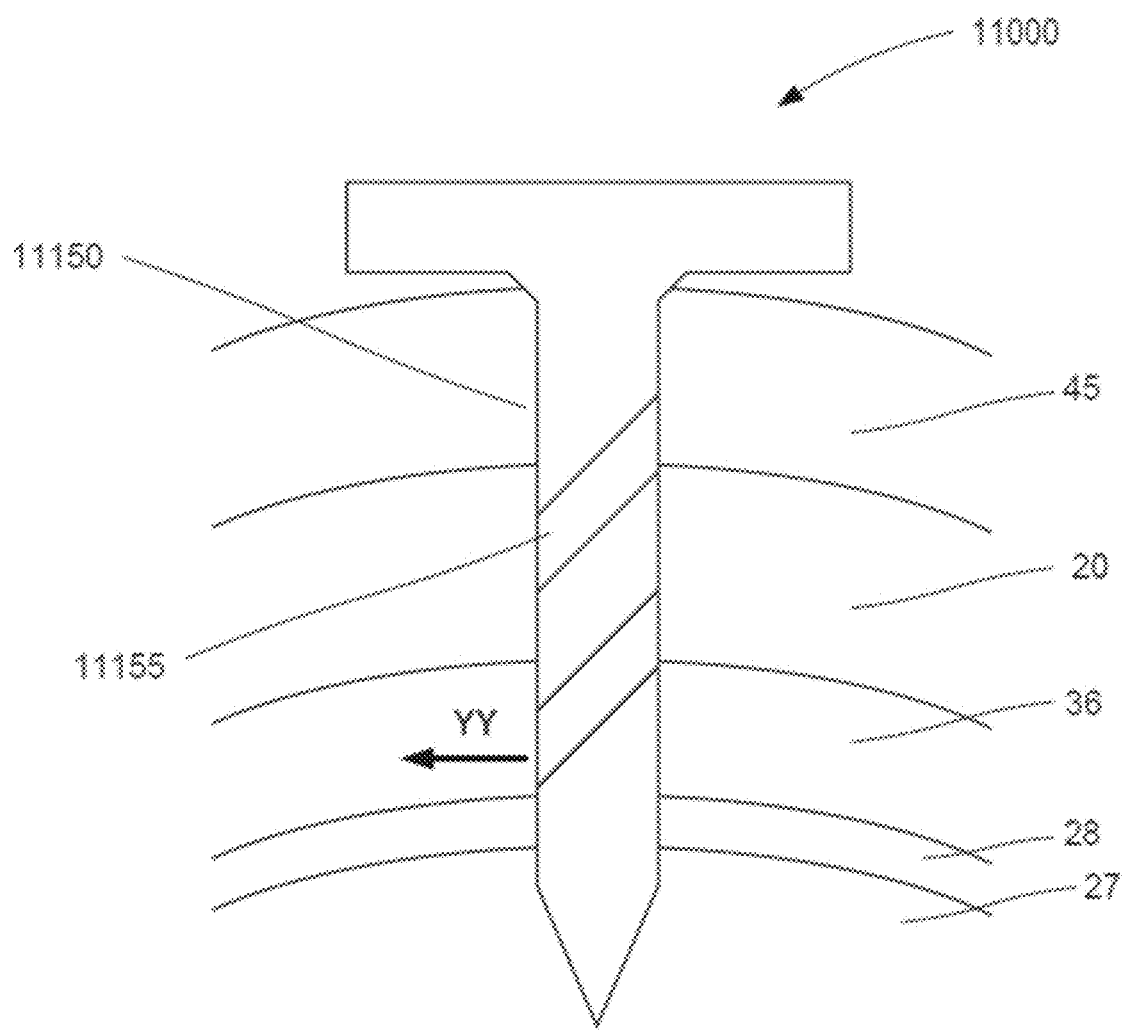
FIG. 27B is a schematic illustration of a medicament delivery apparatus including a needle with a continuous spiral port, according to an embodiment.

In some embodiments, the medicament delivery apparatus has a puncture member that includes lateral ports of various shapes, including, but not limited to, oblong, elongated, square, rectangular, spiral (either continuous or interrupted), or the like. For example, FIG. 27B shows a medicament delivery apparatus 11000 that includes a puncture member 11150 with a lateral port 11155 having a continuous spiral shape extending along the length of the puncture member 11150. When the puncture member 11150 is inserted into the eye, a force having a magnitude less than a threshold value is exerted on an actuation rod (not shown) of the medicament delivery device. As the force is exerted on the actuation rod, if the force is sufficient to overcome the back pressure produced by the tissue, the actuation rod moves within a medicament container of the medicament delivery apparatus and a medicament will be expelled through the portion of the lateral port that is within the tissue with least resistance, e.g., the suprachoroidal space. Specifically, as shown in FIG. 27B, when the lateral port 11155 of the puncture member 11150 enters the suprachoroidal space, a region of lower density, the actuation rod expels the medicament from the medicament container (not shown) through the puncture member 11150 and out of the section of the lateral port 11155 within the suprachoroidal space, as shown by the arrows YY.

In some embodiments, the loss of resistance on the puncture member can be determined through a tactile sensation, such as a person using the medicament delivery apparatus to insert the puncture member into the eye. When the person activates the actuation rod, they can feel any change in resistance as the puncture member is inserted into the eye.

In some embodiments, the loss of resistance can be determined through any other mechanism, such as via an electronic circuit system. The electronic circuit system includes at least a sensor and a controller. The sensor is located adjacent to the lateral port on the puncture member. The controller is located within the medicament delivery apparatus. The sensor relays information to the controller as the puncture member is inserted into the eye. The controller determines any change in density between the layers of the eye and alerts the user of any change in density correlating to the suprachoroidal space of the eye. The alerts can be produced by an audible output or a visual output or a tactile output, such as a vibration. Once alerted, the user can stop inserting the puncture member and disperse a medicament through the lateral port.

In such embodiments, the controller can include a memory, a processor, and an input/output module (or interface). In some embodiments, the controller can also include a feedback module that receives a signal from a sensor. A feedback module includes circuitry, components, and/or code to produce a signal indicating a change in density. Once the user is alerted to the change in density, the user can stop inserting the puncture member and disperse a medicament through the lateral port. In some embodiments, the dispersion of medicine can happen automatically as part of the feedback/control system. The controller can be coupled to a computer or other input/output device via the input/output module (or interface).

The processor (and any of the processors described herein) can be any processor configured to, for example, write data into and read data from the memory of the controller, and execute the instructions and/or methods stored within the memory. Furthermore, the processor can be configured to control operation of the other modules within the controller (e.g., the feedback module). Specifically, the processor can receive a signal including user input, distance measurements or the like. In other embodiments, the processor (and any of the processors described herein) can be, for example, an application-specific integrated circuit (ASIC) or a combination of ASICs, which are designed to perform one or more specific functions. In yet other embodiments, the microprocessor can be an analog or digital circuit, or a combination of multiple circuits.

The memory device of the controller (and any of the memory devices described herein) can be any suitable device such as, for example, a read only memory (ROM) component, a random access memory (RAM) component, electronically programmable read only memory (EPROM), erasable electronically programmable read only memory (EEPROM), registers, cache memory, and/or flash memory. Any of the modules (the feedback module) can be implemented by the processor and/or stored within the memory.

Figure 28:
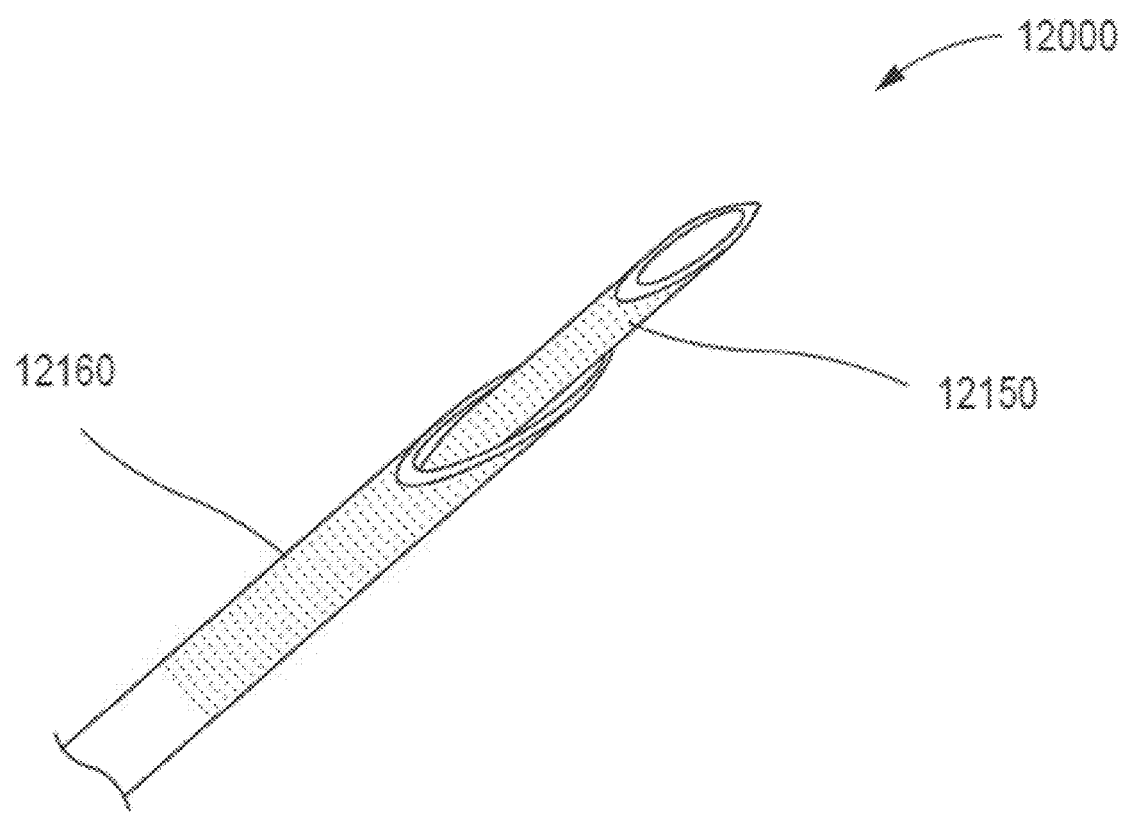
FIG. 28 is a perspective view of a dual puncture member medicament delivery apparatus according to an embodiment.

Although the loss of resistance method described above is performed using the medicament delivery apparatus 9000 having a puncture member 9150 with at least one lateral port 9155, in other embodiments, any suitable medicament delivery device can be effective using a loss of resistance method. For example, FIG. 28 illustrates a dual puncture member medicament delivery assembly ("delivery assembly") 12000 including a microneedle 12150 and a delivery cannula 12160 that can be used to deliver a medicament to a targeted region of an eye. The delivery cannula 12160 has a distal end portion that is sufficiently sharp to penetrate through a conjunctiva and a sclera of the eye. The microneedle 12150 can be, for example, a 33 gauge (or smaller) microneedle. In use, the microneedle 12150 moves in unison with the delivery cannula 12160 through the layers of the eye. As the delivery cannula 12160 penetrates layers of the eye, any loss of resistance can be detected. As mentioned above, the loss of resistance can be determined through a tactile sensation or any other mechanism, such as via an electronic circuit system. Since the conjunctiva and sclera have a higher density than the suprachoroidal space, the suprachoroidal space can serve as a landmark for an eye surgeon because a loss of resistance can be detected as the medicament delivery apparatus passes through the layers of the eye.

Specifically, as the distal end portion of the delivery assembly 12000 is inserted within the eye (not shown), a force is exerted on an actuation rod (not shown). If the force is insufficient to overcome the backpressure produced by the tissue, the actuation rod will not move within the delivery cannula 12160. If, however, the force is sufficient to overcome the backpressure produced by the tissue, the actuation rod moves within the delivery cannula 12160 and an inert compound will be expelled into the suprachoroidal space. Specifically, movement of the actuation rod within the delivery cannula 12160 is limited if it is within a region of the tissue where the backpressure is greater than the force applied to the actuation rod (e.g., the sclera, which has a higher density than the suprachoroidal space). However, when the delivery cannula 12160 enters the suprachoroidal space, a region of lower density, the actuation rod expels the inert compound from the delivery cannula 12160 into the suprachoroidal space. The inert compound can be a protein or similar compound and is used to confirm the placement of the delivery cannula 12160 within the suprachoroidal space. Upon confirmation of proper placement of the delivery cannula 12160, the microneedle 12150 is advanced from the delivery cannula 12160 a further distance, for example, about 300-400 μm, into a subretinal space. The microneedle 12150 moves relative to the delivery cannula 12160 and the microneedle 12150 contains a medicament. Once the microneedle 12150 is in the subretinal space the medicament is injected.

In some embodiments, the delivery assembly is inserted such that the centerline of the delivery passageway and a surface line tangent to a surface of the target tissue defines an angle of entry of between about 75 degrees and about 105 degrees. In some embodiments, the angle of entry is between about 60 degrees and about 75 degrees. In some embodiments, the angle of entry is more than about 45 degrees.

In some embodiments, the force exerted on the actuator of the delivery assembly can be between about 2 N and about 6 N, for example, about 3 N, about 4 N, or about 5 N, inclusive of all ranges therebetween.

In some embodiments, the medicament that is conveyed into the subretinal space is at least one of a VEGF, a VEGF inhibitor, a PDGFR inhibitor, or a combination thereof.

Figure 29:
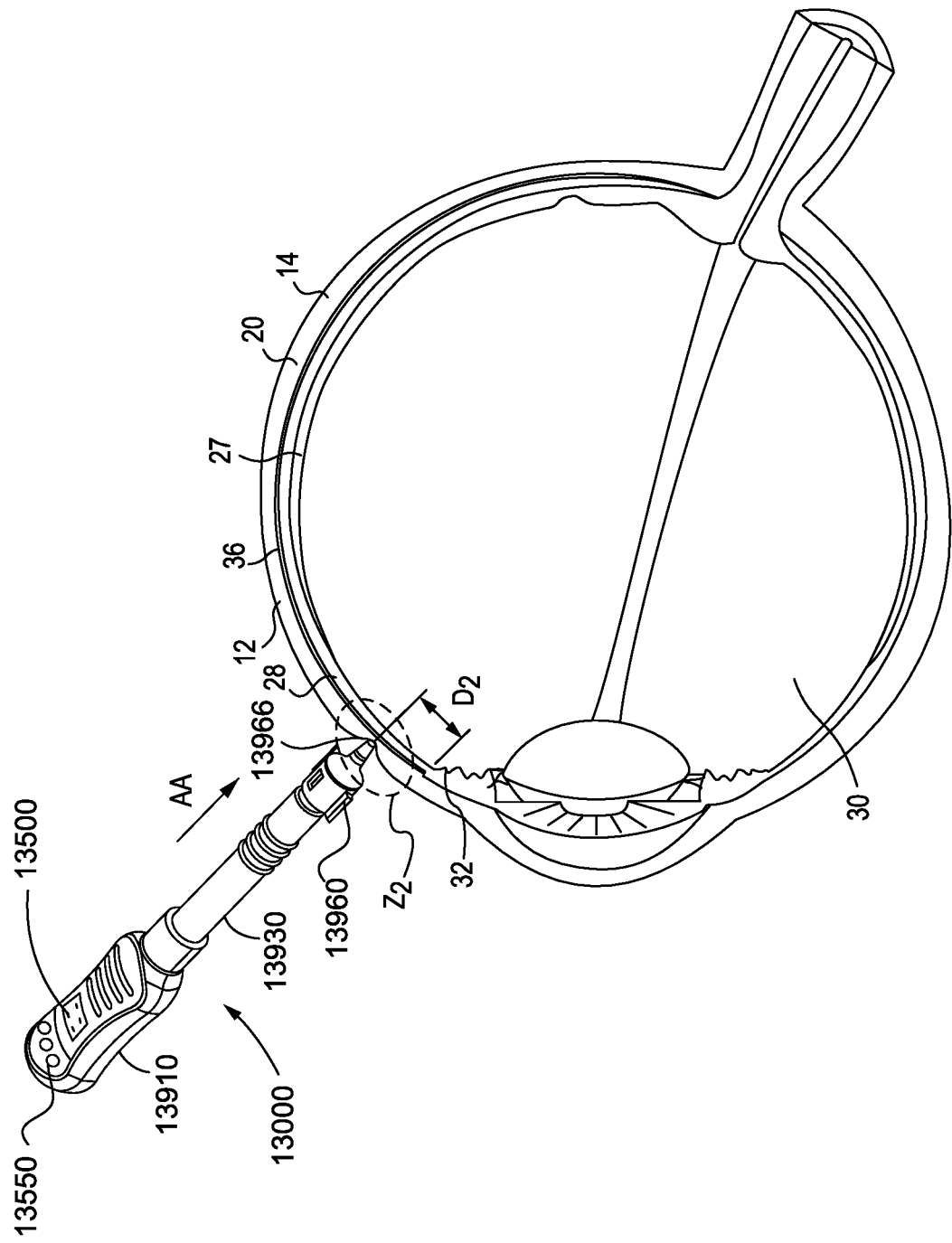
FIG. 29 is a perspective view of a medicament delivery apparatus according to an embodiment.
Figure 30:
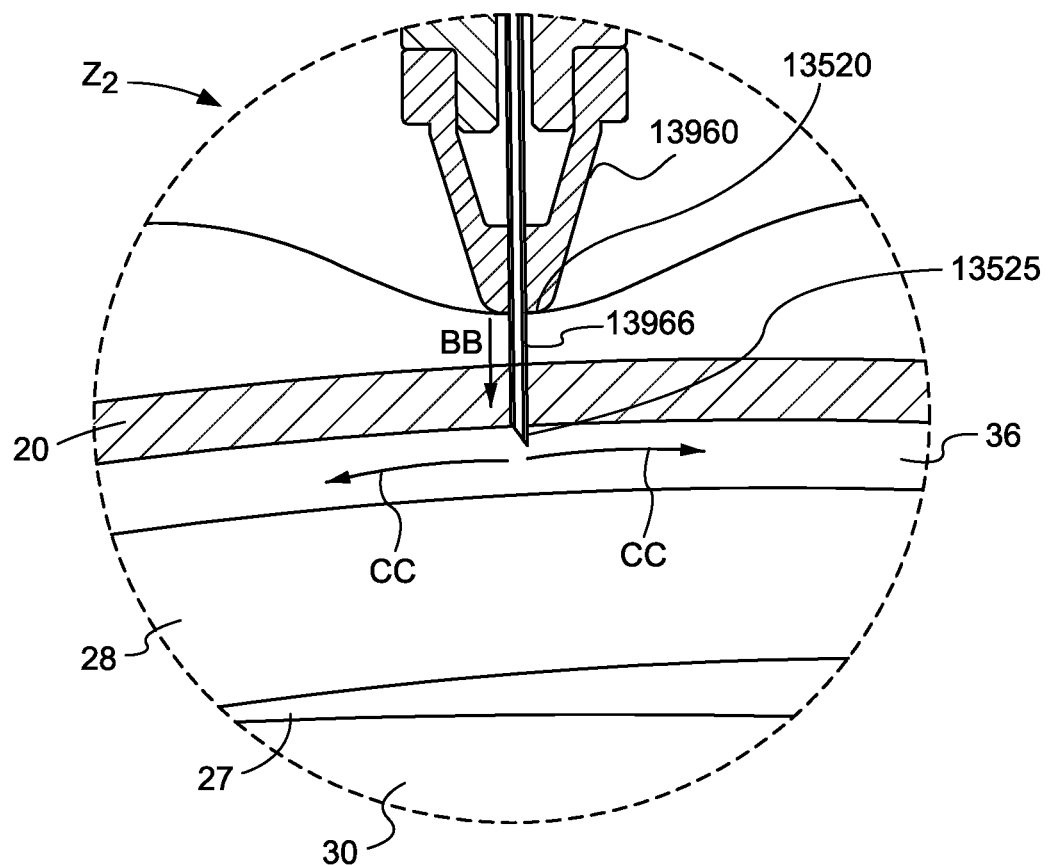
FIG. 30 is a close up view of the medicament delivery device shown in FIG. 29, illustrating the delivery of a medicament to a suprachoroidal space of the eye.

Although the delivery devices described above use a loss of resistance method, in other embodiments, a medicament delivery apparatus includes an electronic circuit system to relay a feedback signal for depth control. The electronic circuit system includes at least one sensor, a controller, and an output device. FIGS. 29 and 30 depict a medicament delivery apparatus 13000 according to such an embodiment. The medicament delivery apparatus 13000 includes a handle 13910, a housing 13930, a hub 13960, and a delivery member 13966. The handle 13910 contains the controller (not shown) and an electronic circuit system 13500 having an output device 13550. The electronic circuit system 13500 also includes sensors 13520, 13525 (not shown in FIG. 29; see FIG. 30) that are contained on at least one of the hub 13960 or the delivery apparatus 13966.

A distal end portion of the handle 13910 is coupled to a proximal end portion of the housing 13930. The housing 13930 contains a medicament container (not shown) and an actuation rod (not shown). The medicament container (not shown) is configured to contain a medicament.

A distal end portion of the housing 13930 is coupled to a proximal end portion of the hub 13960. The hub 13960 houses the delivery member 13966. The delivery member 13966 extends throughout the hub 13960 and a proximal end portion of the delivery member 13966 is connected to the medicament container (not shown) within the housing 13930. A distal end portion of the delivery member 13966 extends beyond a distal end portion of the hub 13960.

The components of the medicament delivery apparatus 13000 can be coupled together using any suitable coupling features, such as, for example, Luer connectors, threads, snap-fit, latch, lock, friction fit, or any suitable coupling features. Although the components of the medicament delivery apparatus 13000 are shown and described as being coupled together, in other embodiments, these components can be monolithically constructed.

As shown in FIG. 29, the delivery member 13966 is inserted into an eye as the medicament delivery apparatus 13000 is advanced toward the eye at a desired angle, as shown by the arrow AA. FIG. 30 is a close up of the area marked as $Z_2$ in FIG. 29. FIG. 30 depicts the electronic circuit system having two sensors 13520, 13525. The first sensor 13520 is coupled to the hub 13960 and the second sensor 13525 is coupled to the delivery member 13966. The sensors 13520 and 13525 relay information to the controller (not shown) as the delivery member 13966 of the medicament delivery apparatus 13000 is inserted into the eye. The controller determines any change in density between the layers of the eye and alerts the user of a change by sending a signal to the output device 13550. Once alerted, the user can stop advancing the medicament delivery apparatus 13000 and can exert force on the actuation rod (not shown) which will then expel a medicament from the medicament container (not shown) through the delivery member 13966, as shown by arrows BB in FIG. 30. The medicament then disperses through the suprachoroidal space as shown by arrow CC in FIG. 30.

In such embodiments, the controller can include a memory, a processor, an input/output module (or interface) and a feedback module that receives a signal from at least one sensor. A feedback module includes circuitry, components, and/or code to produce an output indicating a change in density. The output device produces a signal that is at least one of a tactile signal, an auditory signal, or a visual signal. Once the user is alerted to the change in density, the user can stop inserting the delivery member and disperse a medicament. The controller can be coupled to a computer or other input/output device via the input/output module (or interface).

The processor (and any of the processors described herein) can be any processor configured to, for example, write data into and read data from the memory of the controller, and execute the instructions and/or methods stored within the memory. Furthermore, the processor can be configured to control operation of the other modules within the controller (e.g., the feedback module). Specifically, the processor can receive a signal including user input, distance measurements or the like. In other embodiments, the processor (and any of the processors described herein) can be, for example, an application-specific integrated circuit (ASIC) or a combination of ASICs, which are designed to perform one or more specific functions. In yet other embodiments, the microprocessor can be an analog or digital circuit, or a combination of multiple circuits.

The memory device of the controller (and any of the memory devices described herein) can be any suitable device such as, for example, a read only memory (ROM) component, a random access memory (RAM) component, electronically programmable read only memory (EPROM), erasable electronically programmable read only memory (EEPROM), registers, cache memory, and/or flash memory. Any of the modules (the feedback module) can be implemented by the processor and/or stored within the memory.

The electronic circuity system can include any suitable power source (e.g., battery), processor, and other components to produce the outputs and/or perform the functions described herein. The electrical components can include resistors, capacitors, inductors, diodes, switches, microcontrollers, microprocessors and/or the like. Such components can be operatively coupled by any suitable mechanism, such as, for example, a printed circuit board (not shown in FIGS. 29 and 30) having conductive traces.

In some embodiments, the feedback signal is produced in response to at least one of a pressure gradient, a pH gradient, a conductivity gradient, a resistivity gradient, a color gradient, or reflectivity. Each region of the eye—sclera, choroid, suprachoroidal space—has different characteristics that provide locational feedback indicating the depth of a delivery member. For example, the pH of the tissue changes as a function of depth into the sclera thus signifying the depth of the delivery member.

In some embodiments, the sensor 13525 can be an optical fiber/sensor placed at a distal end portion of a delivery member of the medicament delivery apparatus. As the delivery member is inserted into the eye, the amount of light that is absorbed decreases with a change in depth. This information is sent to the controller of the electronic circuit system and an output device signals when the delivery member has entered the target region of the eye.

Although some of the delivery devices described above use a loss of resistance method to determine when a needle (or puncture member) is within a desired region of the eye, in other embodiments, a medicament delivery apparatus includes a guide that has markings that are normal (perpendicular) to the surface of an eye such that the markings can indicate the distance for the normal (perpendicular) penetration of a delivery member into the eye. Thus, in some embodiments, a delivery device can be configured to deliver a medicament to a desired target region based on the known depth of layers of the eye.

Figure 31:
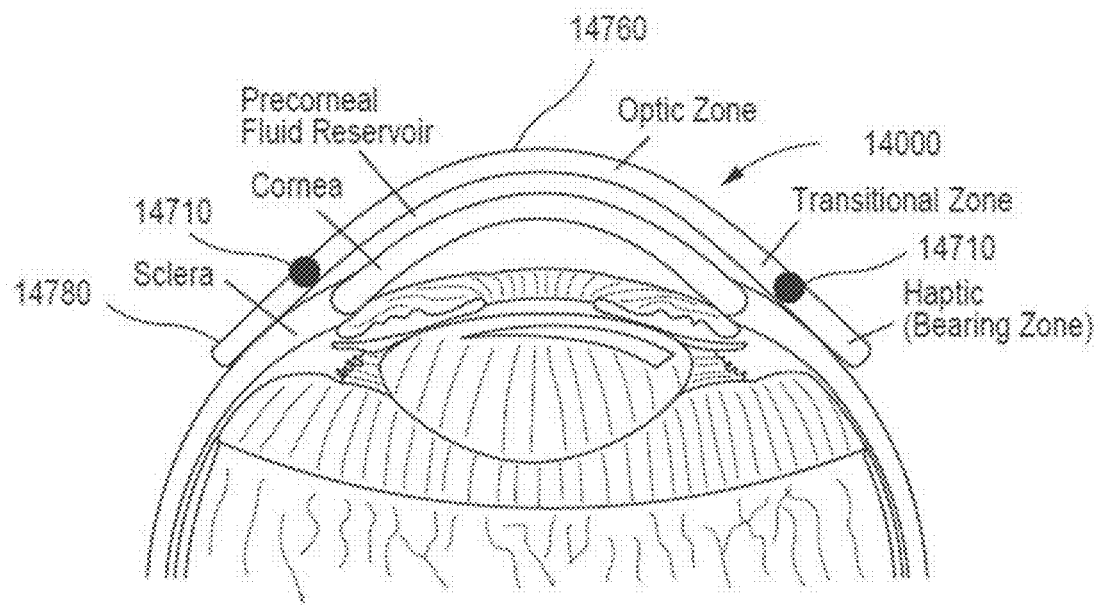
FIG. 31 is a perspective view of a wearable apparatus positioned on the eye according to an embodiment.

Although the medicament delivery devices above have described devices as including components that briefly engage an eye to convey a medicament to a targeted region within the eye, in other embodiments, a wearable apparatus can be coupled to or worn on a surface of the eye and used to convey the medicament to a targeted region within the eye. For example, FIG. 31 shows a wearable apparatus 14000 that is disposed about a surface of an eye. The wearable apparatus 14000 includes a central portion 14760 and a peripheral portion 14780. In use, the central portion 14760 is disposed about a cornea of the eye and has an optical property to facilitate vision therethrough and/or to correct for any visual and optical aberrations in the line of sight. The peripheral portion 14780 contains a series of microneedle assemblies 14710. The microneedle assemblies 14710 are configured to contain a medicament and convey the medicament to a targeted region of the eye.

Figure 32A:
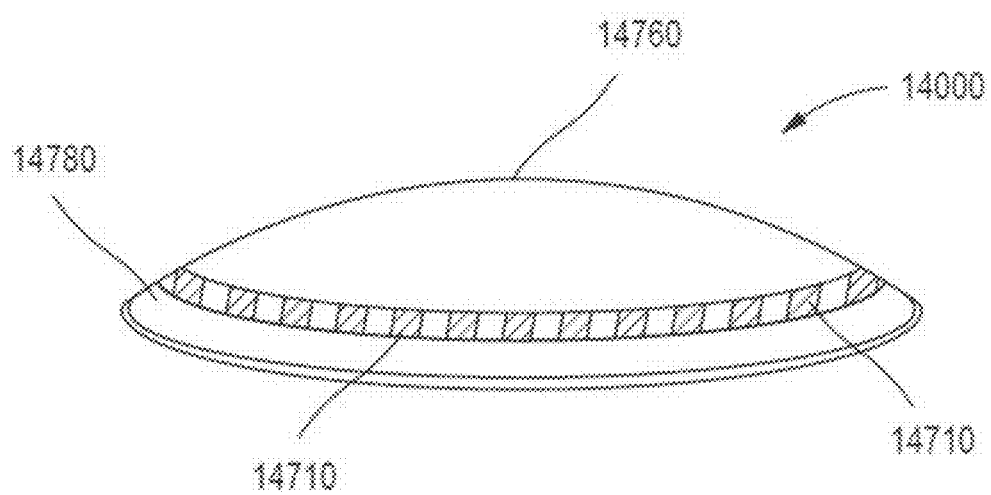
FIG. 32A is a perspective view of a wearable apparatus according to an embodiment.
Figure 32B:
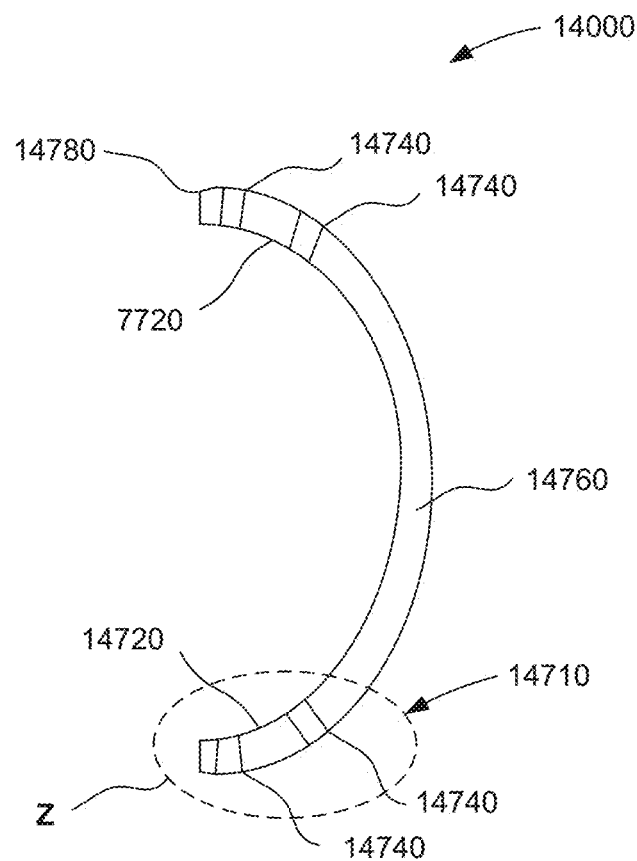
FIG. 32B is a cross-sectional view of the wearable apparatus shown in FIG. 32A.

FIGS. 32A and 32B further illustrate the wearable apparatus 14000. FIG. 32A is a perspective view of the wearable apparatus 14000 which includes the central portion 14760 and the peripheral portion 14780. The series of microneedle assemblies 14710 are coupled to the peripheral portion 14780. FIG. 32B is a cross-sectional view of the wearable apparatus 14000 shown in FIG. 32A and further illustrates the components of the microneedle assembly 14710. Each microneedle assembly 14710 includes an inner member 14720 and two outer members 14740 (or a single circumferential outer member 14740). The outer members 14740 provide a structure for the microneedle assembly 14710 and the inner member 14720 moves relative to the outer members 14740. The inner member 14720 contains a microneedle (not shown), which contains (or through which is conveyed) a medicament.

Figure 33A:
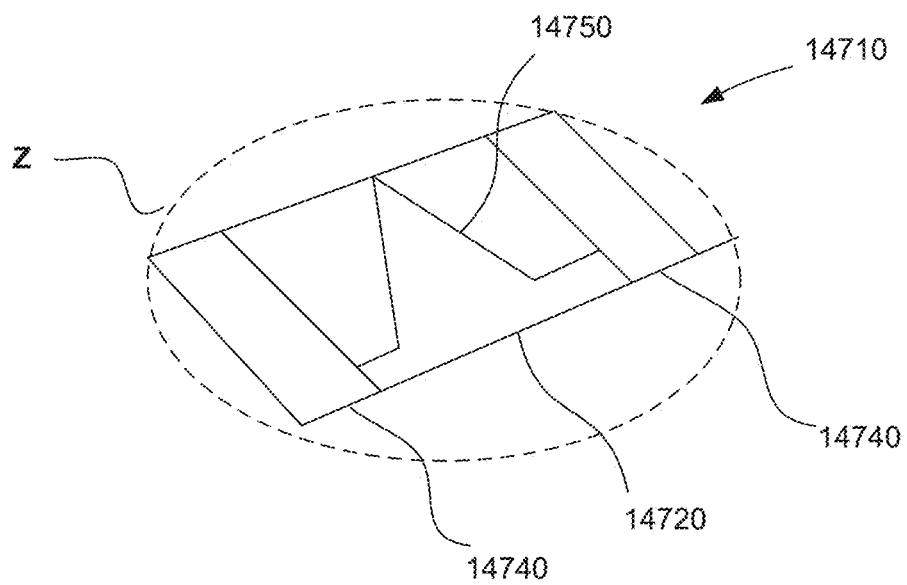
FIGS. 33A and 33B are close up views of a microneedle assembly of the wearable apparatus shown in FIGS. 31, 32A, and 32B, the inner member of the microneedle assembly in a first position and a second position, respectively.
Figure 33B:
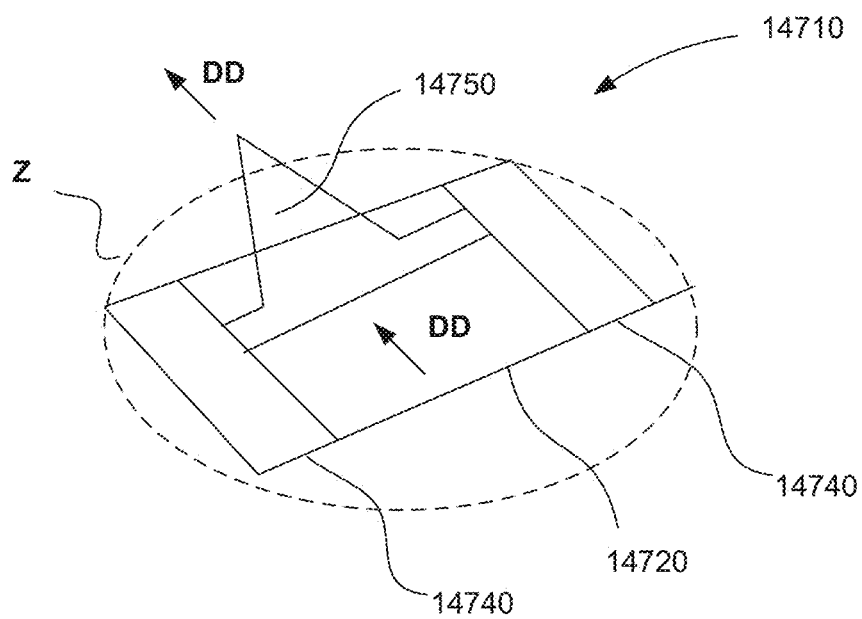

FIGS. 33A and 33B provide a close up view of the section labeled Z in FIG. 32B showing various configurations of the microneedle assembly 14710. FIG. 33A shows the microneedle assembly 14710 in a first configuration wherein the inner member 14720 and microneedle 14750 are between the outer members 14740. FIG. 33B shows the microneedle assembly in a second configuration. When the microneedle assembly 14710 is actuated, the inner member 14720 moves relative to the outer members 14740 into a second configuration where the microneedle 14750 extends outward into the eye, as shown by the arrows DD in FIG. 33B. The microneedle 14750 extends through the conjunctiva and sclera, until the bevel is exposed to a suprachoroidal space of the eye. The actuator (not shown) produces a force sufficient to drive the microneedle 14750 into place but not enough to dislodge the base curve of the wearable device 14000 from the surface of the eye. In some embodiments, the distal edge of the microneedle is sufficiently sharp to enter into the conjunctiva and sclera with minimal force. When the microneedle is driven into place by the actuator, a medicament is simultaneously expelled from the microneedle or microneedle array (not shown) which is organized around the periphery of the wearable device 14000 into the suprachoroidal space of the eye. Once the medicament is expelled into the suprachoroidal space the inner member 14720 can return to the first configuration.

In some embodiments, the microneedle assembly is actuated by a pump actuator that is coupled to the inner member. In such embodiments, a user squeezes an exterior bulb that is connected to the inner member to actuate the microneedle assembly. In some embodiments, the exterior bulb can be similar to that which is found on a perfume bottle. In other embodiments, the exterior bulb can be any suitable pneumatic bulb. When actuated, the pressure exerted from the bulb to the inner member causes the microneedle to extend into the suprachoroidal space and the medicament within the microneedle is forced out into the suprachoroidal space through the microneedle simultaneously.

In some embodiments, the microneedle assembly is actuated by a manual depression of a button on a surface of the wearable apparatus. When the button is depressed, the microneedle is driven into the eye and the medicament is expelled from the microneedle simultaneously.

Figure 34:
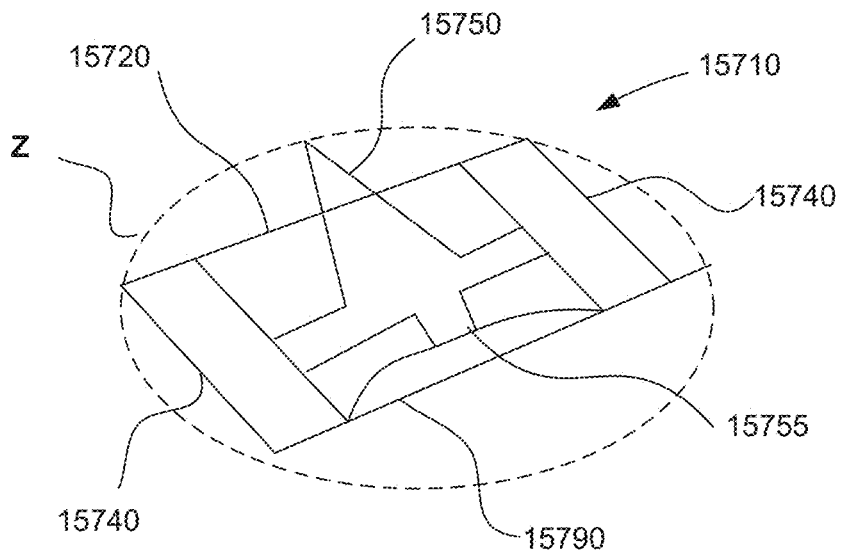
FIG. 34 is a close up view of a wearable apparatus according to an embodiment, this embodiment includes an inner member having a lumen configured to house a medicament and a connection between a microneedle and the lumen.

In some embodiments, the microneedle assembly can include and/or be coupled to a reservoir configured to contain the medicament. In such an embodiment, as shown in FIG. 34, the inner member 15720 of the microneedle assembly 15710 includes a microneedle 15750, a reservoir 15790, and a coupling member 15755. The reservoir 15790 is configured to contain a medicament and is coupled to the microneedle 15750 via a coupling member 15755. The coupling member 15755 can be a flexible connection between the microneedle 15750 and the reservoir 15790. The reservoir 15790 can be configured to be refilled with a medicament so that it can be reused. Although the inner member 15720 is described and depicted as having a coupling member 15755, in some embodiments, the reservoir 15790 is permanently attached to the microneedle 15750. In such embodiments, the reservoir 15790 cannot be refilled. Thus, the device can be designed as a single-use device or a multiple use device.

Figure 35:
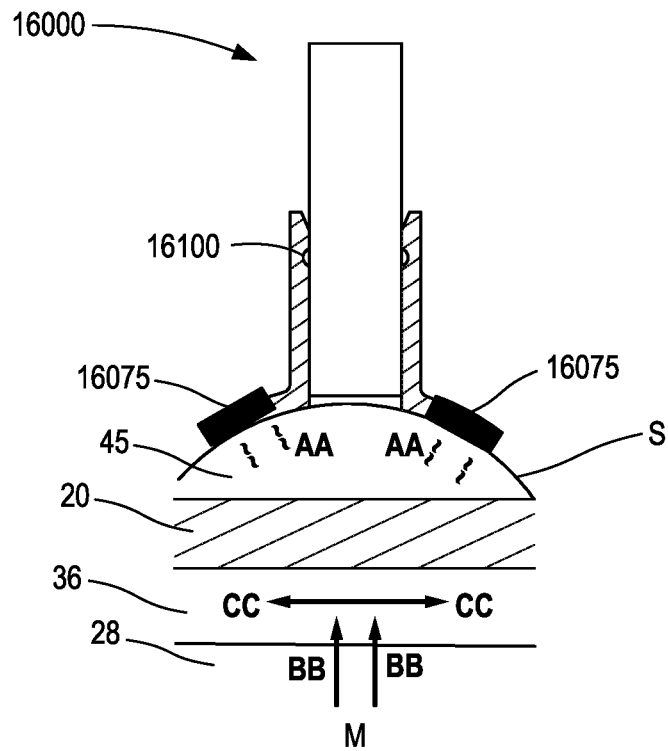
FIG. 35 is a cross-sectional schematic view of an eye and an apparatus according to an embodiment.

In some embodiments, a method for targeted delivery of a medicament to a specific region within the eye is facilitated by administering a carrier to a vascular system of a patient and actuating an energy source at a location outside of an outer surface of an eye. FIG. 35 shows a cross-sectional schematic view of an apparatus 16000, according to an embodiment, used for this method. FIG. 35 shows the apparatus 16000 contacting the surface S of an eye and spaced apart from the underlying layers of the eye (specifically, the conjunctiva 45, the sclera 20, the suprachoroidal space 36, and the vitreous 28 are shown). The apparatus 16000 includes a housing 16100 and an energy source 16575. The housing 16100 can be any suitable structure that positions the energy source 16575 in the desired location relative to the eye. In some embodiments, the housing 16100 is configured to engage or contact the eye in a similar manner as the engagement member 162280 (or any other engagement member) shown and described in U.S. Pat. No. 9,180,047, entitled "APPARATUS AND METHODS FOR OCULAR INJECTION," which is incorporated herein by reference in its entirety. In other embodiments, the housing 16100 can be contacting portions of the eye beneath the conjunctiva of the eye. In yet other embodiments, the housing 16100 can be configured to contact portions of the anatomy away from the eye (e.g., the face) to maintain the housing spaced apart from the surface S (i.e., such that the housing 16100 does not touch the eye).

The energy source 16575 can be any suitable energy source that produces and/or delivers the energy beam (shown by arrows AA). For example, in some embodiments, the energy source 16575 can include one or more electrodes configured to produce an electrical energy beam. In other embodiments, an electrode can produce a beam of magnetic energy. In other embodiments, the energy source 16575 can include one or more light-emitting devices (e.g., lasers, light-emitting diodes, or the like) configured to produce a beam of light energy. Such a light emitting devices can be configured to produce an energy beam at any suitable frequency for degrading the carrier and/or activating the medicament. For example, some embodiments, the energy source 16575 can produce a non-visible beam of electro-magnetic energy (e.g., ultraviolet radiation). In some embodiments, the energy source 16575 can produce a beam of heat (or infrared) energy. In yet other embodiments, the energy source 16575 can include one or more acoustic energy devices (e.g., piezo-electric crystals) configured to produce a beam of acoustic energy (sonic energy, ultrasonic energy, or the like). Thus, the energy source 16575 can be at least one of a magnetic plate, an electrode, a pump applying pressure, a pump applying suction, a chemical energy source, an energy source that produces iontophoretic motion, an energy source that produces thermophoretic motion, or the like.

Figure 36:
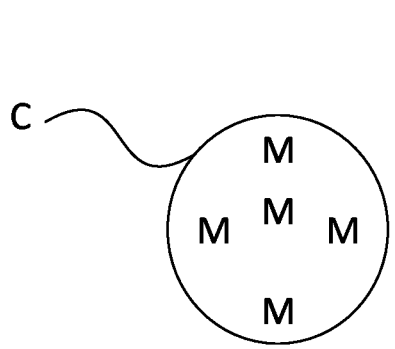
FIG. 36 is a schematic illustration of a carrier formulated to encapsulate a medicament according to an embodiment.

FIG. 36 is a schematic illustration of a carrier C according to an embodiment that is used in conjunction with the apparatus 16000 and/or the methods described herein. The carrier C is formulated to contain a medicament M. The medicament M can be any of the medicaments and/or active agents described herein. The carrier C can be any suitable compound that contains or otherwise binds to the medicament. For example, the carrier C can be a liposome, nanoparticle, microparticle, magnetic particle, nanosphere, microsphere, microcapsule, nanocapsule, electronically charged particle, biodegradable polymer, or the like. FIG. 36 shows one embodiment where the medicament M is contained within the carrier C. In this manner, the carrier C provides a mechanism that delivers the medicament M to a targeted area. The medicament is only active once it is released from the carrier.

Figure 37:
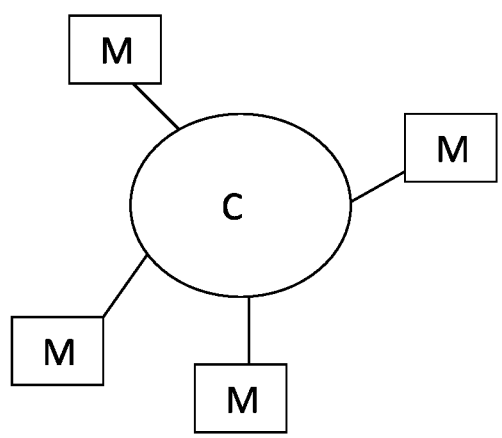
FIG. 37 is a schematic illustration of a carrier formulated to bind to a medicament according to an embodiment.

Although shown as being contained within the carrier C, an alternative embodiment, as shown in FIG. 37, is that a medicament M is tethered to a carrier C. In such embodiments, the carrier C blocks the active portion of the medicament M so the medicament M only becomes active once the medicament M is untethered from the carrier C.

In some embodiments, the carrier is administered to the vascular system of a patient. In some embodiments, the carrier is delivered to the vascular system of a patient via systemic delivery. Systemic delivery can include delivery via at least one of oral delivery, injection directly into the patient's vascular system, inhalation, topical drops, or the like. When the carrier enters the vascular system of a patient, the carrier travels throughout the patient's blood vessels including the blood vessels within a choroid of an eye. In some embodiments, the carrier is administered directly into the suprachoroidal space or the subretinal space via an intravitreal injection or any other route of administration that delivers the carrier into these ocular regions. The carrier can be administered to these ocular regions using any of the devices shown and described in U.S. Pat. No. 9,180,047, entitled "APPARATUS AND METHODS FOR OCULAR INJECTION," U.S. Patent Application 62/330,501, entitled "SYSTEMS AND METHODS FOR DEFINING DRUG DELIVERY PATHWAYS IN BODILY TISSUE," U.S. Patent Application No. 62/341,149, entitled "SYSTEMS AND METHODS FOR DELIVERING DRUGS USING ELECTRONIC FIELDS," and U.S. Patent Application No. 62/359,752, entitled "SYSTEMS AND METHODS FOR OCULAR DRUG DELIVERY," all of which are incorporated herein by reference in their entirety.

The method then includes actuating an energy source to produce an energy beam. The energy source can be, for example, the energy source 16575, and can be at least one of a magnetic plate, an electrode, a pump applying pressure, a pump applying suction, a chemical energy source, an energy source that produces iontophoretic motion, an energy source that produces thermophoretic motion, or the like. The energy beam can be at least one of an infrared beam, an ultrasound beam, a radar beam, a sonar beam, an ultraviolet light wave beam, a microwave beam, an electric charge, a magnetic field, a laser beam, or the like. As shown in FIG. 35, when the energy source 16575 is actuated, an energy beam (shown by arrows AA) is produced and penetrates into the layers of an eye. The energy beam degrades the carrier thereby releasing or untethering the medicament such that the medicament is able to move from a choroidal blood vessel to a targeted region within the eye. The targeted region can be, for example, the suprachoroidal space (SCS), the subretinal space (SRS), or any other suitable location within the eye.

The timing of the actuation of the energy source is dependent on the type of carrier being used and/or the desired timing of the application of the medicament. If a slow administration of a medicament is desired, the energy source could be actuated such that the energy beam is applied constantly over a certain period of time or the energy beam could be applied in bursts over a certain period of time. In these instances, the carrier is slowly degraded causing the medicament to be delivered over time. Such periods of time can be, for example, between about 20 minutes and about 30 minutes, between about 15 minutes and about 25 minutes, between about 10 minutes and 20 minutes, or between about 5 minutes and 15 minutes. However, in other embodiments, a quick administration of the medicament can be achieved by applying the energy beam at a high energy level for a short period of time, which can cause the carrier to rupture immediately thereby releasing the medicament quickly. In such embodiments, the time period can be, for example, between about 2 minutes and about 1 minute, between about 1 minute and about 30 seconds, between about 30 seconds and about 5 seconds, or between about 15 seconds and about 2 seconds.

In some embodiments, the energy beam can be a focused energy beam having a prescribed focal depth, which can degrade or rupture the carrier C that is present in a specific location of the eye. For example, in some embodiments, the energy source 16575 is configured such that the energy beam has a focal depth of between about 800 μm and about 1200 μm. In other embodiments, the energy source 16575 is configured such that the focused beam has a focal depth of between about 600 μm and about 1400 μm.

Figure 38:
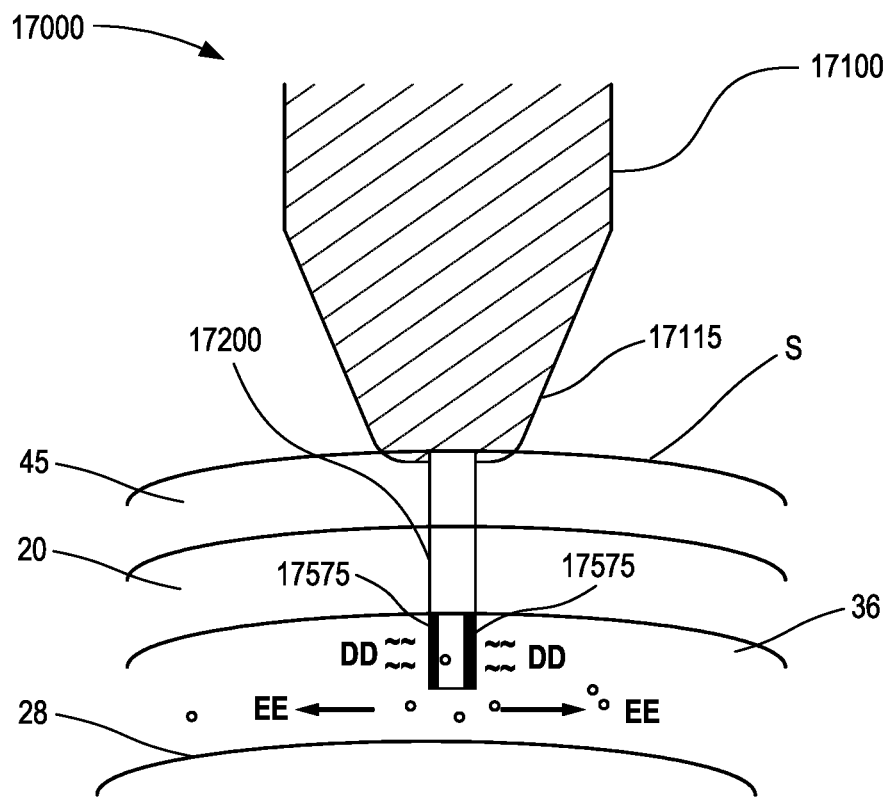
FIG. 38 is a cross-sectional schematic view of an eye and an apparatus according to an embodiment, wherein the apparatus includes an energy source on a delivery member of the apparatus configured to apply an energy to a targeted area in order to activate a medicament.

In some embodiments, application of an internal energy source (i.e., within the body and/or the eye) can be used to activate an inactivated medicament to treat a targeted region within an eye. In some embodiments, an apparatus has an energy source located on a distal end portion of a delivery member. FIG. 38 shows an apparatus 17000 that includes a housing 17100 and a delivery member 17200. The housing 17100 can be any of the housing or hubs shown and described herein and/or in U.S. Pat. No. 9,180,047 entitled "APPARATUS AND METHOD FOR OCULAR INJECTION," the disclosure of which is incorporated herein by reference in its entirety.

The delivery member 17200 can be any suitable device that can be delivered through layers of the eye. For example, the delivery member 17200 can be a needle, a microneedle, a solid puncture member, or the like. The delivery member 17200 is coupled to the distal end portion 17115 of the housing 17100 using any suitable coupling feature, such as, for example, Luer connectors, threads, snap-fit, latch, lock, friction fit, or any other suitable coupling feature. The delivery member 17200 has a distal end portion that includes an energy source 17575. The delivery member 17200 is configured to convey energy to a medicament M in order to activate the medicament M for treatment of the surrounding ocular tissue.

The energy source 17575 is configured to produce and apply an energy to a medicament M in order to activate the medicament M. The energy source 17575 can be at least one of an electrical resistance heater, a peltier heater, a peltier cooler, an ultrasonic heater, a microwave heater, or the like. The energy can be at least one of a thermal energy, radiant energy, electrical energy, or the like.

The apparatus 17000 also includes an electronic circuit system (not shown) that is configured to adjust the energy source to activate the medicament M within an ocular tissue. The electronic circuit system is similar to any of the electronic circuit systems that are shown and described herein.

As shown in FIG. 38, the housing 17100 is placed on the surface S of an eye and the delivery member 17200 extends into the layers of the eye. When the energy source 17575 is activated, energy is produced and delivered to the medicament M as shown by the waves DD. As previously stated, a small temperature increase within the eye can result in damage to the tissue. Thus, in some embodiments, the electronic circuit system maintains the temperature of the surrounding tissue within a range of about 37° C. to about 40° C. Once the temperature of the surrounding tissue has been increased by the energy, the medicament M is activated by being released from a carrier. The arrows EE show the dispersement of the activated medicament M. Although a method of ocular drug delivery is described above as including using an energy source to activate an inactivated medicament to treat a targeted region within an eye, in other embodiments, other methods using an energy source can be used to properly deliver a medicament to a targeted region within the eye. For example, in some embodiments, an energy source is provided to regulate temperature in order to increase the diffusion rate of a medicament to deliver the medicament to a targeted tissue of an eye. Within the eye, the sclera generally has a higher density than the conjunctiva or the suprachoroidal space. Differences in the density of the target region or layer can produce different diffusion rates of a medicament. Thus, in some embodiments, an apparatus to deliver a medicament to a desired target region can be based on such physical differences.

For example, in some embodiments, an apparatus can deliver a medicament to a targeted ocular tissue by increasing the diffusion rate of certain portions of the eye by regulating the temperature. The apparatus can regulate the temperature of the medicament itself or the temperature of the ocular tissue. It is known that an increase in temperature can increase the rate of diffusion. However, temperature increases in the eye can potentially be detrimental to the health of the eye (for example, temperature increases may induce cataract formation). Thus, any increase in temperature of or within ocular tissue must be carefully regulated to avoid damage to the tissue.

Figure 39:
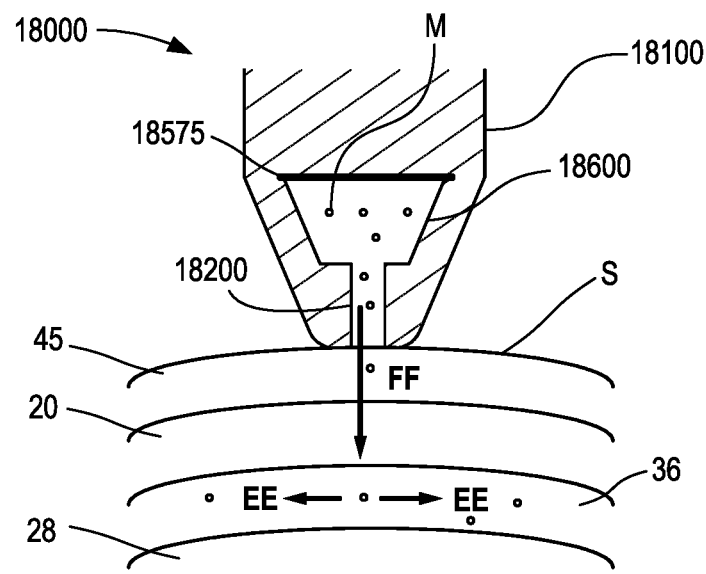
FIG. 39 is a cross-sectional schematic view of an eye and an apparatus according to an embodiment, wherein the apparatus heats the medicament to a desired temperature prior to delivery to a targeted tissue.

In some embodiments, an apparatus includes an energy source that regulates the temperature of a medicament causing an increase in the diffusion rate of the medicament when the medicament is administered to an eye. As shown in FIG. 39, an apparatus 18000 includes a housing 18100 and a delivery member 18200. The housing 18100 defines a reservoir 18600 and includes an energy source 18575. The reservoir 18600 is configured to contain a medicament M and the energy source 18575 is located adjacent to the reservoir 18600. Although the housing 18100 and reservoir 18600 are shown and described as being monolithically constructed, in other embodiments, the housing 18100 can be a separate component from the reservoir 18600. The housing 18100 can be any of the housing or hubs shown and described herein and/or in U.S. Pat. No. 9,180,047 entitled "APPARATUS AND METHOD FOR OCULAR INJECTION," the disclosure of which is incorporated herein by reference in its entirety.

The energy source 18575 is configured to apply an energy to the medicament M. The energy source 18575 can be located adjacent to the reservoir 18600. Alternatively, the energy source 18575 can be located within the reservoir 18600. The energy source 18575 can be at least one of an electrical resistance heater, a Peltier heater, a Peltier cooler, an ultrasonic heater, a microwave heater, or the like. The energy can be at least one of a thermal energy, radiant energy, electrical energy, or the like. As shown in FIG. 39, the energy source 18575 is located at the top of the reservoir 18600. When the energy source 18575 is actuated, the energy source 18575 produces energy that increases the temperature of the medicament M within the reservoir 18600.

The apparatus 18000 also includes an electronic circuit system (not shown) that is configured to adjust the energy produced by the energy source 18575 to regulate the temperature of the medicament. As previously stated, a small temperature increase within the eye can result in damage to the tissue. Thus, in some embodiments, the electronic control system maintains the temperature of the medicament within a range of about 37° C. to about 40° C.

The electronic circuit system includes at least a feedback module and an actuation module. The feedback module is implemented at least in part in hardware and, in some embodiments, can include a sensor. The sensor is configured to detect the temperature of the medicament within the reservoir. The actuation module is configured to send a signal to the energy source 18575 to adjust the energy produced such that the temperature of the medicament is changed.

In some embodiments the electronic circuit system can include a memory, a processor, and an input/output module (or interface). The electronic circuit system can be coupled to a computer or other input/output device via the input/output module (or interface). The processor (and any of the processors described herein) can be any processor configured to, for example, write data into and read data from the memory of the electronic circuit system, and execute the instructions and/or methods stored within the memory. Furthermore, the processor can be configured to control operation of the other modules within the electronic circuit system (e.g., the feedback module). In other embodiments, the processor (and any of the processors described herein) can be, for example, an application-specific integrated circuit (ASIC) or a combination of ASICs, which are designed to perform one or more specific functions. In yet other embodiments, the microprocessor can be an analog or digital circuit, or a combination of multiple circuits.

The memory device of the electronic circuit system (and any of the memory devices described herein) can be any suitable device such as, for example, a read only memory (ROM) component, a random access memory (RAM) component, electronically programmable read only memory (EPROM), erasable electronically programmable read only memory (EEPROM), registers, cache memory, and/or flash memory. Any of the modules (the feedback module) can be implemented by the processor and/or stored within the memory.

The delivery member 18200 can be any suitable device through which the medicament M is conveyed into the eye. For example, the delivery member 18200 can be a nozzle, a needle, a microneedle, a solid puncture member, or the like. The delivery member is coupled to the reservoir 18600 using any suitable coupling feature, such as, for example, Luer connectors, threads, snap-fit, latch, lock, friction fit, or any other suitable coupling feature.

As shown in FIG. 39, to deliver the medicament M, the housing 18100 is placed on the surface S of an eye. The medicament M is heated to the desired temperature, as described above. The medicament M can be heated and maintained at the desired temperature before the housing 18100 is placed on the surface S, or after the housing 18100 is placed on the surface S. The device 18000 is actuated to convey the medicament M. The arrow FF shows the direction that the medicament M moves through the delivery member 18200 when the medicament M is delivered to an eye. The arrows EE show the dispersement of the medicament M when delivered to the targeted ocular tissue when the temperature of the medicament M is maintained at the desired temperature.

Figure 40:
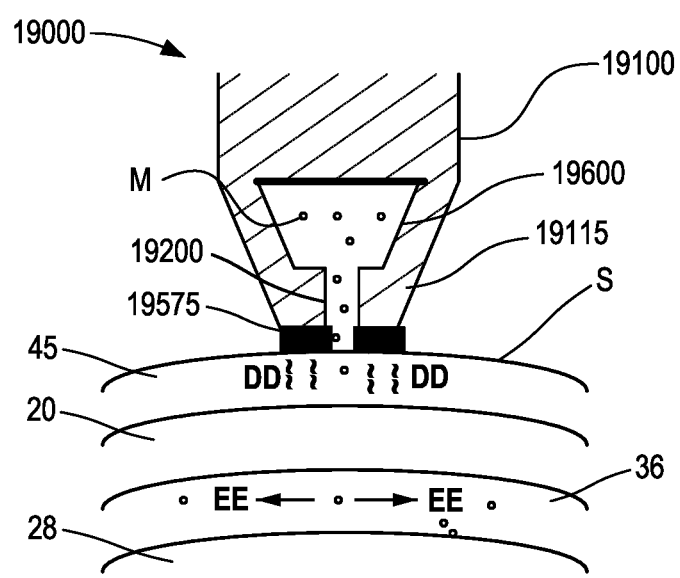
FIG. 40 is a cross-sectional schematic view of an eye and an apparatus according to an embodiment, wherein the apparatus includes an energy source on a distal end portion of the housing configured to apply an energy to a target tissue.

In some embodiments, an apparatus includes an energy source that increases the temperature of a tissue to increase the diffusion rate of a medicament when the medicament is administered to an eye. As shown in FIG. 40, an apparatus 19000 includes a housing 19100, an energy source 19575, and a delivery member 19200. The housing 19100 has a distal end portion 19115 that defines a reservoir 19600, which is configured to contain a medicament M. Although the housing 19100 and reservoir 19600 are shown and described as being monolithically constructed, in other embodiments, the housing 19100 can be a separate component from the reservoir 19600. The housing can be any of the housing or hubs shown and described herein and/or in U.S. Pat. No. 9,180,047 entitled "APPARATUS AND METHOD FOR OCULAR INJECTION," the disclosure of which is incorporated herein by reference in its entirety.

In some embodiments, the energy source 19575 is coupled to the distal end portion 19115 of the housing 19100 and is configured to apply an energy to a target tissue. The energy source 19575 can be at least one of an electrical resistance heater, a Peltier heater, a Peltier cooler, an ultrasonic heater, a microwave heater, or the like. The energy can be at least one of a thermal energy, radiant energy, electrical energy, or the like. As shown in FIG. 40, the energy source 19575 is located at the distal end portion of the housing 19100. When the energy source 19575 is actuated, the energy source 19575 produces energy (as shown by the waves designated DD) that increases the temperature of the target tissue.

The apparatus 19000 also includes an electronic circuit system (not shown) that is configured to adjust the energy to regulate the temperature of the target tissue. As previously stated, a small temperature increase within the eye can result in damage to the tissue. Thus, in some embodiments, the electronic circuit system maintains the temperature of the target tissue within a range of about 37° C. to about 40° C.

The electronic circuit system includes at least a feedback module and an actuation module. The feedback module is implemented at least in part in hardware and in some embodiments, includes a sensor. The sensor is configured to detect the temperature of the target tissue. The actuation module is configured to send a signal to the energy source 19575 to adjust the energy such that the temperature of the tissue is changed.

In some embodiments the electronic circuit system can include a memory, a processor, and an input/output module (or interface). The electronic circuit system can be coupled to a computer or other input/output device via the input/output module (or interface). The processor (and any of the processors described herein) can be any processor configured to, for example, write data into and read data from the memory of the electronic circuit system, and execute the instructions and/or methods stored within the memory. Furthermore, the processor can be configured to control operation of the other modules within the electronic circuit system (e.g., the feedback module). In other embodiments, the processor (and any of the processors described herein) can be, for example, an application-specific integrated circuit (ASIC) or a combination of ASICs, which are designed to perform one or more specific functions. In yet other embodiments, the microprocessor can be an analog or digital circuit, or a combination of multiple circuits.

The memory device of the electronic circuit system (and any of the memory devices described herein) can be any suitable device such as, for example, a read only memory (ROM) component, a random access memory (RAM) component, electronically programmable read only memory (EPROM), erasable electronically programmable read only memory (EEPROM), registers, cache memory, and/or flash memory. Any of the modules (the feedback module) can be implemented by the processor and/or stored within the memory.

The delivery member 19200 can be any suitable device through which the medicament M is conveyed into the eye. For example, the delivery member 19200 can be a nozzle, a needle, a microneedle, a solid puncture member, or the like. The delivery member 19200 is coupled to the reservoir 19600 using any suitable coupling feature, such as, for example, Luer connectors, threads, snap-fit, latch, lock, friction fit, or any other suitable coupling feature. As shown in FIG. 40, the housing 19100 is placed on the surface S of an eye. When the energy source 19575 is activated, an energy is produced and delivered to a target tissue as shown by the waves DD. Once the temperature of the target tissue has been increased by the energy, an actuator (not shown) is actuated and causes the medicament M to be expelled from the reservoir 19600. The arrows EE show the dispersement of the medicament M when delivered to the targeted ocular tissue.

Figure 41:
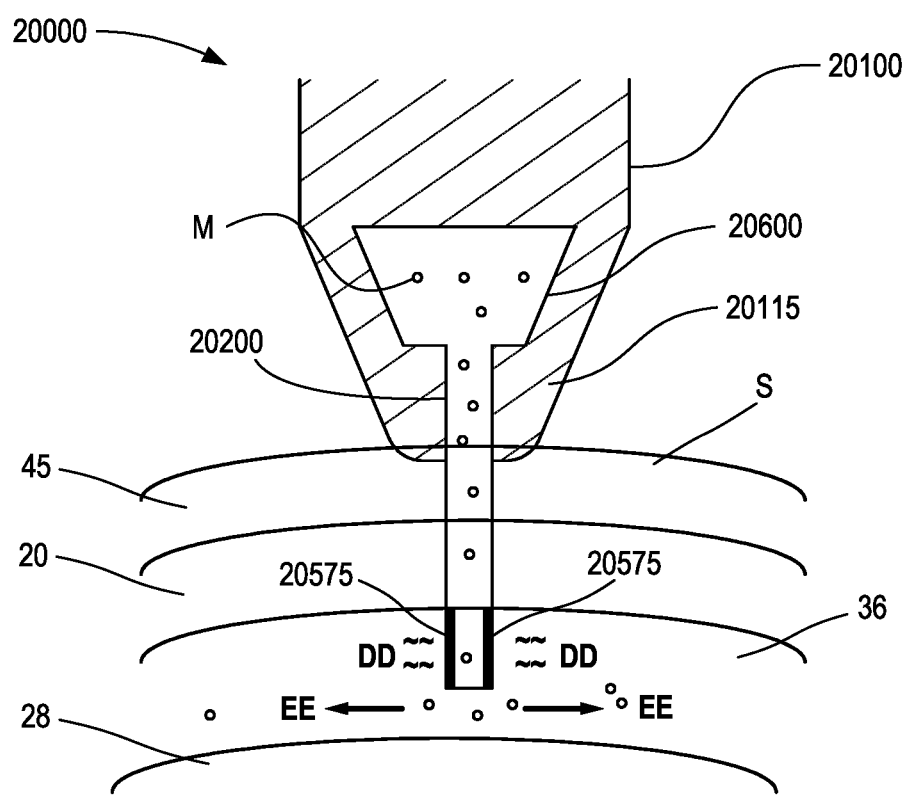
FIG. 41 is a cross-sectional schematic view of an eye and an apparatus according to an embodiment, wherein the apparatus includes an energy source on a delivery member of the apparatus configured to apply an energy to a target tissue.

In some embodiments, an apparatus has an energy source located on a distal end portion of a delivery member. FIG. 41 shows an apparatus 20000 that includes a housing 20100 and a delivery member 20200. The housing 20100 has a distal end portion 20115 and it defines a reservoir 20600, which is configured to contain a medicament M. Although the housing 20100 and reservoir 20600 are shown and described as being monolithically constructed, in other embodiments, the housing 20100 can be a separate component from the reservoir 20600. The housing can be any of the housing or hubs shown and described herein and/or in U.S. Pat. No. 9,180,047 entitled "APPARATUS AND METHOD FOR OCULAR INJECTION," the disclosure of which is incorporated herein by reference in its entirety.

The delivery member 20200 can be any suitable device that can be delivered through layers of the eye and through which the medicament M is conveyed into the eye. For example, the delivery member 20200 can be a needle, a microneedle, a solid puncture member, or the like. The delivery member 20200 is coupled to the distal end portion 20115 of the housing 20100 using any suitable coupling feature, such as, for example, Luer connectors, threads, snap-fit, latch, lock, friction fit, or any other suitable coupling feature. The delivery member 20200 is configured to convey the medicament M to a target tissue. The delivery member 20200 has a distal end portion that includes an energy source 20575.

The energy source 20575 is configured to apply an energy to a target tissue. The energy source 20575 can be at least one of an electrical resistance heater, a Peltier heater, a Peltier cooler, an ultrasonic heater, a microwave heater, or the like. The energy can be at least one of a thermal energy, radiant energy, electrical energy, or the like.

The apparatus 20000 also includes an electronic circuit system (not shown) that is configured to adjust the energy source to regulate the temperature of the target tissue. The electronic circuit system is similar to any of the electronic circuit systems that are shown and described herein.

As shown in FIG. 41, the housing 20100 is placed on the surface S of an eye and the delivery member 20200 extends into the layers of the eye. When the energy source 20575 is activated, energy is produced and delivered to a target tissue as shown by the waves DD. As previously stated, a small temperature increase within the eye can result in damage to the tissue. Thus, in some embodiments, the electronic circuit system maintains the temperature of the target tissue within a range of about 37° C. to about 40° C. Once the temperature of the target tissue has been increased by the energy, the delivery member 20200 expels the medicament M from the reservoir 20600. The arrows EE show the dispersement of the medicament M when delivered to the targeted ocular tissue.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

For example, although the devices are shown and described herein as delivering a therapeutic compound to the suprachoroidal space in other embodiments, any of the devices and methods described herein can be used to deliver a therapeutic compound to any suitable tissue. In some embodiments, any of the devices and methods described herein can be used to deliver a therapeutic compound to a skin, bone, organ or other tissue. Moreover, any of the devices and methods described herein can be used to deliver a therapeutic compound to any suitable region within the eye, such as, for example, the subretinal space, the choroid, or any other desired region.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices.

Examples of computer code include, but are not limited to, micro-code or microinstructions, machine instructions, such as produced by a compiler, code used to produce a web service, and files containing higher-level instructions that are executed by a computer using an interpreter. For example, embodiments may be implemented using imperative programming languages (e.g., C, FORTRAN, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

A wide range of ocular diseases and disorders may be treated by the methods and with the devices described herein. Non-limiting examples of such ocular diseases include uveitis, glaucoma, diabetic macular edema or retinopathy, macular degeneration, retinoblastoma, and genetic diseases. The methods described herein are particularly useful for the local delivery of drugs that need to be administered to the posterior region of the eye, for example the retinochoroidal tissue, macula, and optic nerve in the posterior segment of the eye. In one embodiment, the delivery methods and devices described herein may be used in gene-based therapy applications. For example, the methods may administer a fluid drug formulation into the suprachoroidal space to deliver select DNA, RNA, or oligonucleotides to targeted ocular tissues Any of the vials, containers, and/or kits shown and described herein can include and/or be used with any suitable drug, medicament or therapeutic agent of the types mentioned herein. As used herein, the term "drug" refers to any prophylactic, therapeutic, or diagnostic agent (e.g., a contrast agent). The drug may be selected from suitable proteins, peptides and fragments thereof, which can be naturally occurring, synthesized or recombinantly produced. Representative examples of types of drugs for delivery to ocular tissues include antibodies, anti-viral agents, chemotherapeutic agents (e.g., topoisomerase inhibitors), analgesics, anesthetics, aptamers, antihistamines, anti-inflammatory agents, and anti-neoplastic agents. In one embodiment, the drug is triamcinolone or triamcinolone acetonide.

The term "antibody" is intended to refer broadly to any immunologic binding agent such as IgG, IgM, IgA, IgD and IgE. An antibody can be monoclonal or polyclonal, and in one embodiment, is a humanized antibody. The term "antibody" is also used to refer to any antibody-like molecule that has an antigen binding region, and includes antibody fragments such as Fab', Fab, F(ab')2, single domain antibodies (DABs), Fv, scFv (single chain Fv), and engineering multivalent antibody fragments such as dibodies, tribodies and multibodies. The techniques for preparing and using various antibody-based constructs and fragments are well known in the art (see, e.g., Antibodies: A Laboratory Manual, Cold Spring Harbor Laboratory, 1988; incorporated herein by reference).

Non-limiting examples of specific drugs and classes of drugs include β-adrenoceptor antagonists (e.g., carteolol, cetamolol, betaxolol, levobunolol, metipranolol, timolol), miotics (e.g., pilocarpine, carbachol, physostigmine), sympathomimetics (e.g., adrenaline, dipivefrine), carbonic anhydrase inhibitors (e.g., acetazolamide, dorzolamide), topoisomerase inhibitors (e.g., topotecan, irinotecan, camptothecin, lamellarin D, etoposide, teniposide, doxorubicin, mitoxantrone, amsacrine), prostaglandins, anti-microbial compounds, including anti-bacterials and anti-fungals (e.g., chloramphenicol, chlortetracycline, ciprofloxacin, framycetin, fusidic acid, gentamicin, neomycin, norfloxacin, ofloxacin, polymyxin, propamidine, tetracycline, tobramycin, quinolines), anti-viral compounds (e.g., acyclovir, cidofovir, idoxuridine, interferons), aldose reductase inhibitors, anti-inflammatory and/or anti-allergy compounds (e.g., steroidal compounds such as betamethasone, clobetasone, dexamethasone, fluorometholone, hydrocortisone, prednisolone and non-steroidal compounds such as antazoline, bromfenac, diclofenac, indomethacin, lodoxamide, saprofen, sodium cromoglycate), artificial tear/dry eye therapies, local anesthetics (e.g., amethocaine, lignocaine, oxbuprocaine, proxymetacaine), cyclosporine, diclofenac, urogastrone and growth factors such as epidermal growth factor, mydriatics and cycloplegics, mitomycin C, collagenase inhibitors, treatments of age-related macular degeneration (e.g., pegagtanib sodium, ranibizumab, aflibercept and bevacizumab), and glutocorticoid receptor antagonists (e.g., fosdagrocorat, dagrocorat, mapracorat, mifepristone).

In some embodiments, a kit and/or vial includes an integrin antagonist, a selectin antagonist, an adhesion molecule antagonist (e.g., intercellular adhesion molecule (ICAM)-1, ICAM-2, ICAM-3, platelet endothelial adhesion molecule (PCAM), vascular cell adhesion molecule (VCAM)), a leukocyte adhesion-inducing cytokine or growth factor antagonist (e.g., tumor necrosis factor-α (TNF-α), interleukin-1β (IL-1β), monocyte chemotatic protein-1 (MCP-1), or a vascular endothelial growth factor (VEGF)). In some embodiments, a vascular endothelial growth factor (VEGF) inhibitor is included within a kit and/or administered with one of the devices or via any of the methods described herein. In some embodiments, two drugs are included within a kit and/or are delivered by the methods described herein. The compounds may be administered in one formulation, or administered serially, in two separate formulations. For example, both a VEGF inhibitor and VEGF are provided. In some embodiments, the VEGF inhibitor is an antibody, for example a humanized monoclonal antibody. In further embodiments, the VEGF antibody is bevacizumab. In another embodiment, the VEGF inhibitor is ranibizumab, aflibercept or pegaptanib. In still other embodiments, the devices and methods described herein can be used to deliver one or more of the following VEGF antagonists: AL8326, 2C3 antibody, AT001 antibody, HyBEV, bevacizumab (Avastin), ANG3070, APX003 antibody, APX004 antibody, ponatinib (AP24534), BDM-E, VGX100 antibody (VGX100 CIRCADIAN), VGX200 (c-fos induced growth factor monoclonal antibody), VGX300, COSMIX, DLX903/1008 antibody, ENMD2076, Sutent (sunitinib malate), INDUS815C, R84 antibody, KD019, NM3, allogenic mesenchymal precursor cells combined with an anti-VEGF agent or antibody, MGCD265, MG516, VEGF-Receptor kinase inhibitors, MP0260, NT503, anti-DLL4/VEGF bispecific antibody, PAN90806, Palomid 529, BD0801 antibody, XV615, lucitanib (AL3810, E3810), AMG706 (motesanib diphosphate), AAV2-sFLT01, soluble FM receptor, Cediranib (Recentin), AV-951 (Tivozanib, KRN-951), Stivarga (regorafenib), Volasertib (BI6727), CEP11981, KH903, Lenvatinib (E7080), terameprocol (EM1421), ranibizumab (Lucentis), Votrient (pazopanib hydrochloride), PF00337210, PRS050, SPO1 (curcumin), Carboxyamidotriazole orotate, hydroxychloroquine, linifanib (ABT869, RG3635), Iluvien (fluocinolone acetonide), ALG1001, AGN150998, DARPin MP0112, AMG386, ponatinib (AP24534), AVA101, Vargatef (nintedanib), BMS690514, KH902, golvatinib (E7050), Afinitor (everolimus), Dovitinib lactate (TKI258, CHIR258), ORA101, ORA102, Axitinib (Inlyta, AG013736), Plitidepsin (Aplidin), Lenvatinib mesylate, PTC299, aflibercept (Zaltrap, Eylea), pegaptanib sodium (Macugen, LI900015), Visudyne (verteporfin), bucillamine (Rimatil, Lamin, Brimani, Lamit, Boomiq), R3 antibody, AT001/r84 antibody, troponin (BLS0597), EG3306, vatalanib (PTK787), Bmab100, GSK2136773, Anti-VEGFR Alterase, Avila, CEP7055, CLT009, ESBA903, HuMax-VEGF antibody, GW654652, HMPL010, GEM220, HYB676, JNJ17029259, TAK593, XtendVEGF antibody, Nova21012, Nova21013, CP564959, Smart Anti-VEGF antibody, AG028262, AG13958, CVX241, SU14813, PRS055, PG501, PG545, PTI101, TG100948, ICS283, XL647, enzastaurin hydrochloride (LY317615), BC194, quinolines, COT601M06.1, COT604M06.2, MabionVEGF, SIR-Spheres coupled to anti-VEGF or VEGF-R antibody, Apatinib (YN968D1), and AL3818. In addition, delivery of a VEGF inhibitor or VEGF antagonist using the devices and methods disclosed herein may be combined with one or more agents listed herein or with other agents known in the art.

In one embodiment, delivery of a VEGF antagonist to the suprachoroidal space of the eye using the kits, devices, and methods disclosed herein is used to treat, prevent and/or ameliorate a disease or disorder selected from leukemia, relapsed/refractory leukemia, acute lymphoblastic leukemia, Acute myelogenous leukemia, relapsed or refractory acute myeloid leukemia, atopic dermatitis, recurrent or metastatic carcinoma of the urothelium, advanced urothelial carcinoma, blood disorders, myelofibrosis, brain tumor, glioblastoma, glioma, meningioma, cancer, carcinomatous meningitis (neoplastic meningitis), choroidal neovascularization (CNV), subfoveal choroidal neovascularization, chronic lymphocytic leukemia, chronic myelogenous leukemia, refractory chronic myelogenous leukemia, colon cancer, colorectal cancer, degenerative nerve diseases, Neurodegenerative diseases, diabetic macular edema, visual Impairment due to diabetic macular edema, diabetic retinopathy, dry eye syndrome (inflammation and corneal tissue damage of dry Eye), endometrial cancer, eye diseases, ocular diseases, ocular neovascularization, eye cancer, Neurofibromatosis Type II, head and neck cancer, hematological malignancies, Kaposi's Sarcoma, Hepatocellular Carcinoma, Lung cancer, macular degeneration, age related macular degeneration, exudative age-related macular degeneration, neovascular (wet) age-related macular degeneration (AMD)), subfoveal Neovascular Age-Related macular degeneration, macular edema, macular edema associated with Branch Retinal Vein Occlusion, macular edema following retinal vein occlusion, macular edema with Retinal Vein Occlusion (RVO), multiple myeloma, relapsed or refractory multiple myeloma, multiple sclerosis, myopia, pathological myopia, neuroendocrine tumor, carcinoid tumor, neuroendocrine tumor, non-Hodgkin's Lymphoma, Diffuse Large B-Cell Lymphoma, Non-Small-Cell Lung cancer, Non-Squamous Non-Small-Cell Lung cancer, Non-small-cell-lung Adenocarcinoma, Squamous Non-Small-Cell Lung cancer, corneal graft rejection, osteoarthritis, recurrent symptomatic malignant ascites, peripheral T-cell lymphoma, androgen Independent Psoriasis, pulmonary Fibrosis, Idiopathic Pulmonary Fibrosis, respiratory diseases, retinal detachment, retinal disorders, retinitis pigmentosa, retinal vein occlusion, branch retinal vein occlusion, central retinal vein occlusion, rheumatoid arthritis, sarcoma, alveolar soft part sarcoma, soft tissue sarcoma, scleroderma/systemic sclerosis, solid tumors, refractory germ cell tumors, thyroid cancer, differentiated or medullar thyroid cancer, and West Syndrome (Infantile Spasm).

In certain embodiments, the drug delivered to the suprachoroidal space using the kits, devices, and methods disclosed herein is rapamycin (Sirolimus, Rapamune). In one embodiment, the devices (e.g., microneedle devices, jet injector, rigid member, and the like) and methods disclosed herein are used in conjunction with rapamycin to treat, prevent and/or ameliorate a wide range of diseases or disorders including, but not limited to: abdominal neoplasms, acquired immunodeficiency syndrome, acute coronary syndrome, acute lymphoblastic leukemia, acute myelocytic leukemia, acute non-lymphoblastic leukemia, adenocarcinoma, adenoma, adenomyoepithelioma, adnexal diseases, anaplastic astrocytoma, anaplastic large cell lymphoma, anaplastic plasmacytoma, anemia, angina pectoris, angioimmunoblastic lymphadenopathy with dysproteinemia, angiomyolipoma, arterial occlusive diseases, arteriosclerosis, astrocytoma, atherosclerosis, autoimmune diseases, B-cell lymphomas, blood coagulation disorders, blood protein disorders, bone cancer, bone marrow diseases, brain diseases, brain neoplasms, breast beoplasms, bronchial neoplasms, carcinoid syndrome, carcinoid Tumor, carcinoma, squamous cell carcinoma, central nervous system diseases, central nervous system neoplasms, choroid diseases, choroid plexus neoplasms, choroidal neovascularization, choroiditis, chronic lymphocytic leukemia, chronic myeloid leukemia, chronic myelomonocytic leukemia, chronic myeloproliferative disorders, chronic neutrophilic leukemia, clear cell renal cell carcinoma, colonic diseases, colonic neoplasms, colorectal neoplasms, coronary artery disease, coronary disease, coronary Occlusion, coronary restenosis, coronary stenosis, coronary thrombosis, cutaneous T-cell lymphoma, diabetes mellitus, digestive system neoplasms, dry eye syndromes, ear diseases, edema, endocrine gland neoplasms, endocrine system diseases, endometrial neoplasms, Endometrial stromal tumors, Ewing's sarcoma, exanthema, eye neoplasms, fibrosis, follicular lymphoma, gastrointestinal diseases, gastrointestinal neoplasms, genital neoplasms, glioblastoma, glioma, gliosarcoma, graft vs host disease, hematologic diseases, hematologic neoplasms, hemorrhagic disorders, hemostatic disorders, Hodgkin disease, Hodgkin lymphoma, homologous wasting disease, immunoblastic lymphadenopathy, immunologic deficiency syndromes, immunoproliferative disorders, infarction, inflammation, intestinal diseases, intestinal neoplasms, ischemia, kidney cancer, kidney diseases, kidney neoplasms, leukemia, B-Cell, leukemia, lymphoid, liver cancer, liver diseases, lung diseases, lymphatic diseases, lymphoblastic lymphoma, lymphoma, macular degeneration, macular edema, melanoma, mouth neoplasms, multiple myeloma, myelodysplastic syndromes, myelofibrosis, myeloproliferative disorders, neuroectodermal tumors, neuroendocrine tumors, neuroepithelioma, neurofibroma, renal cancer, respiratory tract diseases, retinal degeneration, retinal diseases, retinal neoplasms, retinoblastoma, rhabdomyosarcoma, thoracic neoplasms, uveitis, vascular diseases, Waldenstrom Macroglobulinemia, and wet macular degeneration. In addition, delivery of rapamycin using the devices and methods disclosed herein may be combined with one or more agents listed herein or with other agents known in the art.

In one embodiment, the drug delivered to ocular tissue, for example the sclera or suprachoroidal space, using the kits, devices, and methods disclosed herein reduces, inhibits, prevents and/or ameliorates inflammation. Examples of drugs that reduce, inhibit, prevent and/or ameliorate inflammation include (but are not limited to): 19AV Agonists, 19GJ agonists, 2MD Analogs, 4SC101, 4SC102, 57-57, 5-HT2 Receptor Antagonist, 64G12, A804598, A967079, AAD2004, AB1010, AB224050, abatacept, Abegrin, Abevac, AbGn134, AbGn168, Abki, ABN912, ABR215062, ABR224050, Abrammune, Abreva, ABS15, ABS4, ABS6, ABT122, ABT325, ABT494, ABT874, ABT963, ABXIL8, ABXRB2, AC430, Accenetra, Acdeam, ACE772, Acebid, Acebloc, aceclofenac, acetaminophen, chlorzoxazone, serrapeptase, tizanidine hydrochloride, betadex, Aceclogesic Plus, Aceclon, Acecloren, Aceclorism, acecrona, Aceffein, acemetacin, Acenac, Acenterine, Acetal-SP, ibuprofen, Acetyl-G, acetylsalicylate dl-lysine, acetylsalicylic acid, Acicot, Acifine, Acik, Aclocen, Acloflam-P, Aclomore, Aclon, A-CQ, ACS15, actarit, Actemra, Acthelea liofilizado, Actifast, Actimab-B, Actiquim, Actirin, Actis PLUS, activated leukocyte cell adhesion molecule antibody, Acular X, AD452, adalimumab, ADAMTSS Inhibitor, ADC1001, Adco-Diclofenac, Adco-Indomethacin, Adco-Meloxicam, Adco-Naproxen, Adco-Piroxicam, Adcort, Adco-Sulindac, adenosine triphosphate disodium, AdenosineA2a Receptor Agonist, Adimod, Adinos, Adioct, Adiodol, Adipoplus, adipose derived stem and/or regenerative cells, Adizen, Adpep, Advacan, Advagraf, Advel, Adwiflam, AEB071, Aental, Afenac, Affen Plus, Afiancen, Afinitor, Aflamin, Aflazacort, Aflogen, Afloxan, AFM15, AFM16, AFM17, AFM23, Afpred-Dexa, AFX200, AG011, Agafen, aganirsen, AGI1096, Agidex, AGS010, Agudol, A-Hydrocort, AIK1, AIN457, Airtal, AIT110, AJM300, ajulemic acid, AK106, AL-24-2A1, AL4-1A1, Ala Cort, Alanz, Albumin immuneglobulin, alclometasone dipropionate, ALD518, aldesleukin, Aldoderma, alefacept, alemtuzumab, Alequel, Alergolon, Alergosone, Aletraxon, Alfenac, Algason, Algin vek coat, Algioflex, Algirex, Algivin Plus, alicaforsen sodium, Alin, Alinia, Aliviodol, Aliviosin, alkaline phosphatase, ALKS6931, allantoin, Allbupen, Allmol, Allochrysine, allogeneic endothelial cells, allogeneic mesenchymal precursor cells, allogeneic mesenchymal stem cells, alminoprofen, alpha 1 antitrypsin, Alpha 7 nicotinic agonists, alpha amylase, alpha chymotrypsin, alpha fetoprotein, alpha linolenic acid, Alpha-1-antitrypsin, Alpha2BetA1 Integrin Inhibitors, Alphacort, Alphafen, alpha-hexidine, alpha-trypsin, Alphintern, Alpinamed mobility omega 3, Alpoxen, AL-Rev 1, Alterase, ALX0061, ALX0761, ALXN1007, ALXN1102, AM3840, AM3876, AMAB, AMAP102, Amason, Ambene, AmbezimG, amcinonide, AME133v, Amecin, Ameloteks, A-Methapred, Amevive, AMG108, AMG139, AMG162, AMG181, AMG191, AMG220, AMG623, AMG674, AMG714, AMG719, AMG729, AMG827, Amidol, amifampridine phosphate, Amifenac, Amimethacin, amiprilose hydrochloride, Amiprofen, Ammophos, Amoflam, AMP110, Ampikyy, Ampion, ampiroxicam, amtolmetin guacil, AMX256, AN6415, ANA004, ANA506, Anabu, Anacen, Anaflam, Anaflex ACI, Anaida, anakinra, Analgen Artritis, Anapan, Anaprox, Anavan, Anax, Anco, andrographis, Aneol, Anergix, Anervax.RA, Anflene, ANG797, Anilixin, Anmerushin, Annexin 1 peptides, annexin A5, Anodyne, Ansaid, Anspirin, Antarene, Anti BST2 antibody, Anti C5a MAb, Anti ILT7 antibody, Anti VLA1 antibody, Anti-alpha 11 antibody, Anti-CD4 802-2, Anti-CD86 Monoclonal Antibody, Anti-chemokine, Anti-DC-SIGN, Anti-HMGB-1 MAb, Anti-IL-18 Mab, Anti-IL-1R MAb, Anti-IL-1R MAb, Anti-IL23 BRISTOL, Anti-inflammatory Peptides, Anti-interleukin 1Beta antibody, Anti-LIGHT antibody, Anti-LIGHT antibody, Anti-MIF Antibody, Anti-MIF Antibody, Anti-miR181a, antioxidant inflammation modulators, Antiphlamine, AntiRAGE MAb, antithrombin III, Anti-TIRC-7 MAb, Anusol-HC, Anyfen, AP105, AP1089, AP1189, AP401, AP501, apazone, APD334, Apentac, APG103, Apidone, apilimod mesylate, Apitac, Apitoxin, Apizel, APN Inhibitor, apo-Azathioprine, Apo-Dexamethasone, ApoE mimetics, ApoFasL, apo-Indomethacin, apo-mefenamic, apo-methotrexate, apo-nabumetone, Apo-Napro-NA, apo-Naproxen, aponidin, apo-Phenylbutazone, apo-Piroxicam, apo-Sulin, Apo-Tenoxicam, apo-Tiaprofenic, Apranax, apremilast, apricoxib, Aprofen, Aprose, Aproxen, APX001 antibody, APX007 antibody, APY0201, AqvoDex, AQX108, AQX1125, AQX131135, AQX140, AQX150, AQX200, AQX356, AQXMN100, AQXMN106, ARA290, Arava, Arcalyst, Arcoxia, Arechin, Arflur, ARG098, ARG301, arginine aescin, arginine deiminase (pegylated), ARGX109 antibody, ARGX110, Arheuma, Aristocort, Aristospan, Ark-AP, ARN4026, Arofen, Aroff EZ, Arolef, Arotal, Arpibru, Arpimune, Arpu Shuangxin, ARQ101, Arrestin SP, Arrox, ARRY162, ARRY371797, ARRY614, ARRY872, ART621, Artamin, Arthfree, Artho Tech, Arthrexin, Arthrispray, Arthrotec, Arthrovas, Artifit, Artigo, Artin, Artinor, Artisid, Artoflex, Artren Hipergel, Artridol, Artrilase, Artrocaptin, Artrodiet, Artrofen, Artropan, Artrosil, Artrosilene, Artrotin, Artrox, Artyflam, Arzerra, AS604850, AS605858, Asacol, ASA-Grindeks, Asazipam, Aseclo, ASF1096, ASF1096, ASK8007, ASKP1240, ASLAN003, Asmo ID, Asonep, ASP015K, ASP2408, ASP2409, Aspagin, Aspeol, Aspicam, Aspirimex, aspirin, AST120, astaxanthin, AstroCort, Aszes, AT002 antibody, AT007, AT008 antibody, AT008 antibody, AT010, AT1001, atacicept, Ataspin, Atepadene, Atgam, ATG-Fresenius, Athrofen, ATIO03, atiprimod, ATL1222, ATN103, ATN192, ATR107, Atri, Atrmin, Atrosab antibody, ATX3105, AU801, auranofin, Aurobin, Auropan, Aurothio, aurotioprol, autologous adipose derived regenerative cells, Autonec, Avandia, AVE9897, AVE9940, Avelox, Avent, AVI3378, Avloquin, AVP13546, AVP13748, AVP28225, AVX002, Axcel Diclofenac, Axcel Papain, Axen, AZ17, AZ175, Azacortid, AZA-DR, Azafrine, Azamun, Azanin, Azap, Azapin, Azapren, Azaprin, Azaram, Azasan, azathioprine, AZD0275, AZD0902, AZD2315, AZD5672, AZD6703, AZD7140, AZD8309, AZD8566, AZD9056, Azet, Azintrel, azithromycin, Az-od, Azofit, Azolid, Azoran, Azulene, Azulfidine, Azulfin, B1 antagonists, Baclonet, BAF312, BAFF Inhibitor, Bages, Baily S.P., Baleston, Balsolone, baminercept alfa, bardoxolone methyl, baricitinib, Barotase, Basecam, basiliximab, Baxmune, Baxo, BAY869766, BB2827, BCX34, BCX4208, Becfine, Beclate-C, Beclate-N, Beclolab Q, beclomethasone dipropionate, Beclorhin, Becmet-CG, Begita, Begti, belatacept, belimumab, Belosalic, Bemetson, Ben, Benevat, Benexam, Benflogin, Benisan, Benlysta, Benlysta, benorilate, Benoson, benoxaprofen, Bentol, benzydamine hydrochloride, Benzymin, Beofenac, Berafen, Berinert, Berlofen, Bertanel, Bestamine, Bestofen, Beta Nicip, Betacort, Betacorten G, Betafoam, beta-glucan, Betalar, Beta-M, Betamed, Betamesol, betamethasone, betamethasone dipropionate, betamethasone sodium, betamethasone sodium phosphate, betamethasone valerate, Betane, Betanex, Betapanthen, Betapar, Betapred, Betason, Betasonate, Betasone, Betatrinta, Betaval, Betazon, Betazone, Betesil, Betnecort, Betnesol, Betnovate, Bextra, BFPC13, BFPC18, BFPC21, BFPT6864, BG12, BG9924, BI695500, BI695501, BIA12, Big-Joint-D, BIIB023 antibody, Bi-ksikam, Bingo, BioBee, Bio-Cartilage, Bio-C-Sinkki, Biodexone, Biofenac, Bioreucam, Biosone, Biosporin, BIRB796, Bitnoval, Bitvio, Bivigam, BKT140, BKTP46, BL2030, BL3030, BL4020, BL6040, BL7060, BLI1300, blisibimod, Blokium B12, Blokium Gesic, Blokium, BMS066, BMS345541, BMS470539, BMS561392, BMS566419, BMS582949, BMS587101, BMS817399, BMS936557, BMS945429, BMS-A, BN006, BN007, BNP166, Bonacort, Bonas, bone marrow stromal cell antigen 2 antibody, Bonflex, Bonifen, Boomiq, Borbit, Bosong, BRO2001, BR3-FC, Bradykinin B1 Receptor Antagonist, Bredinin, Brexecam, Brexin, Brexodin, briakinumab, Brimani, briobacept, Bristaflam, Britten, Broben, brodalumab, Broen-C, bromelains, Bromelin, Bronax, Bropain, Brosiral, Bruace, Brufadol, Brufen, Brugel, Brukil, Brusil, BT061, BTI9, BTK kinase inhibitors, BTT1023 antibody, BTT1507, bucillamine, Bucillate, Buco Reigis, bucolome, Budenofalk, budesonide, Budex, Bufect, Bufencon, Bukwang Ketoprofen, Bunide, Bunofen, Busilvex, busulfan, Busulfex, Busulipo, Butartrol, Butarut B12, Butasona, Butazolidin, Butesone, Butidiona, BVX10, BXL628, BYM338, B-Zone, C1 esterase inhibitor, C243, c4462, c5997, C5aQb, c7198, c9101, C9709, c9787, CAB101, cadherin 11 antibody, caerulomycin A, CAL263, Calcort, Calmatel, CAM3001, Camelid Antibodies, Camlox, Camola, Campath, Camrox, Camtenam, canakinumab, *Candida albicans* antigen, Candin, cannabidiol, CAP1.1, CAP1.2, CAP2.1, CAP2.2, CAP3.1, CAP3.2, Careram, Carimune, Cariodent, Cartifix, CartiJoint, Cartilago, Cartisafe-DN, Cartishine, Cartivit, Cartril-S, Carudol, CaspaCIDe, CaspaCIDe, Casyn, CAT1004, CAT1902, CAT2200, Cataflam, Cathepsin S inhibitor, Catlep, CB0114, CB2 agonist, CC0478765, CC10004, CC10015, CC1088, CC11050, CC13097, CC15965, CC16057, CC220, CC292, CC401, CC5048, CC509, CC7085, CC930, CCR1 Antagonist, CCR6 Inhibitor, CCR7 Antagonist, CCRL2 antagonist, CCX025, CCX354, CCX634, CD Diclofenac, CD102, CD103 Antibody, CD103 Antibody, CD137 antibody, CD16 antibody, CD18 antibody, CD19 antibody, CD1d Antibody, CD20 antibody, CD200Fc, CD209 antibody, CD24, CD3 antibody, CD30 antibody, CD32A antibody, CD32B antibody, CD4 antibody, CD40 ligand, CD44 antibody, CD64 antibody, CDC839, CDC998, CDIM4, CDIM9, CDK9-Inhibitor, CDP146, CDP323, CDP484, CDP6038, CDP870, CDX1135, CDX301, CE224535, Ceanel, Cebedex, Cebutid, Ceclonac, Ceex, CEL2000, Celact, Celbexx, Celcox, Celebiox, Celebrex, Celebrin, Celecox, celecoxib, Celedol, Celestone, Celevex, Celex, CELG4, Cell adhesion molecule antagonists, CellCept, Cellmune, Celosti, Celoxib, Celprot, Celudex, cenicriviroc mesylate, cenplacel-1, CEP11004, CEP37247, CEP37248, Cephyr, Ceprofen, Certican, certolizumab pegol, Cetofenid, Cetoprofeno, cetylpyridinium chloride, CF101, CF402, CF502, CG57008, CGEN15001, CGEN15021, CGEN15051, CGEN15091, CGEN25017, CGEN25068, CGEN40, CGEN54, CGEN768, CGEN855, CGI1746, CGI560, CGI676, Cgtx-Peptides, CH1504, CH4051, CH4446, chaperonin 10, chemokine C-C motif ligand 2, chemokine C-C motif ligand 2 antibody, chemokine C-C motif ligand 5 antibody, chemokine C-C motif receptor 2 antibody, chemokine C-C motif receptor 4 antibody, chemokine C-X-C motif ligand 10 antibody, chemokine C-X-C motif ligand 12 aptamer, Chemotaxis Inhibitor, Chillmetacin, chitinase 3-like 1, Chlocodemin, Chloquin, chlorhexidine gluconate, chloroquine phosphate, choline magnesium trisalicylate, chondroitin sulfate, Chondroscart, CHR3620, CHR4432, CHR5154, Chrysalin, Chuanxinlian, Chymapra, Chymotase, chymotrypsin, Chytmutrip, CI202, CI302, Cicloderm-C, Ciclopren, Cicporal, Cilamin, Cimzia, cinchophen, cinmetacin, cinnoxicam, Cinoderm, Cinolone-S, Cinryze, Cipcorlin, cipemastat, Cipol-N, Cipridanol, Cipzen, Citax F, Citogan, Citoken T, Civamide, CJ042794, CJ14877, c-Kit monoclonal antibody, cladribine, Clafen, Clanza, Claversal, clazakizumab, Clearoid, Clease, Clevegen, Clevian, Clidol, Clindac, Clinoril, Cliptol, Clobenate, Clobequad, clobetasol butyrate, clobetasol propionate, Clodol, clofarabine, Clofen, Clofenal LP, Clolar, Clonac, Clongamma, clonixin lysine, Clotasoce, Clovacort, Clovana, Cloxin, CLT001, CLT008, C-MAF Inhibitor, CMPX1023, Cnac, CNDO201, CNI1493, CNTO136, CNTO148, CNT01959, Cobefen, CoBenCoDerm, Cobix, Cofenac, Cofenac, COG241, COL179, colchicine, *Colchicum* Dispert, Colchimax, Colcibra, Coledes A, Colesol, Colifoam, Colirest, collagen, type V, Comcort, complement component (3b/4b) receptor 1, Complement Component C1s Inhibitors, complement component C3, complement factor 5a receptor antibody, complement factor 5a receptor antibody, complement factor D antibody, Condrosulf, Condrotec, Condrothin, conestat alfa, connective tissue growth factor antibody, Coolpan, Copaxone, Copiron, Cordefla, Corhydron, Cort S, Cortan, Cortate, Cort-Dome, Cortecetine, Cortef, Corteroid, Corticap, Corticas, Cortic-DS, corticotropin, Cortiderm, Cortidex, Cortiflam, Cortinet M, Cortinil, Cortipyren B, Cortiran, Cortis, Cortisolu, cortisone acetate, Cortival, Cortone acetate, Cortopin, Cortoral, Cortril, Cortypiren, Cosamine, Cosone, cosyntropin, COT Kinase Inhibitor, Cotilam, Cotrisone, Cotson, Covox, Cox B, COX-2/5-LO Inhibitors, Coxeton, Coxflam, Coxicam, Coxitor, Coxtral, Coxypar, CP195543, CP412245, CP424174, CP461, CP629933, CP690550, CP751871, CPSI2364, C-quin, CR039, CR074, CR106, CRA102, CRAC channel inhibitor, CRACM Ion Channel Inhibitor, Cratisone, CRB15, CRC4273, CRC4342, C-reactive protein 2-methoxy ethyl phosphorothioate oligonucleotide, CreaVax-RA, CRH modulators, critic-aid, Crocam, Crohnsvax, Cromoglycic acid, cromolyn sodium, Cronocorteroid, Cronodicasone, CRTX803, CRx119, CRx139, CRx150, CS502, CS670, CS706, CSF1R Kinase Inhibitors, CSL324, CSL718, CSL742, CT112, CT1501R, CT200, CT2008, CT2009, CT3, CT335, CT340, CT5357, CT637, CTP05, CTP10, CT-P13, CTP17, Cuprenil, Cuprimine, Cuprindo, Cupripen, Curaquin, Cutfen, CWF0808, CWP271, CX1020, CX1030, CX1040, CX5011, Cx611, Cx621, Cx911, CXC chemokine receptor 4 antibody, CXCL13 antibodies, CXCR3 antagonists, CXCR4 antagonist, Cyathus 1104 B, Cyclo-2, Cyclocort, cyclooxygenase-2 inhibitor, cyclophosphamide, Cyclorine, Cyclosporin A Prodrug, Cyclosporin analogue A, cyclosporine, Cyrevia, Cyrin CLARIS, CYT007TNFQb, CYT013IL1bQb, CYT015IL17Qb, CYT020TNFQb, CYT107, CYT387, CYT99007, cytokine inhibitors, Cytopan, Cytoreg, CZC24832, D1927, D9421C, daclizumab, danazol, Danilase, Dantes, Danzen, dapsone, Dase-D, Daypro, Daypro Alta, Dayrun, Dazen, DB295, DBTP2, D-Cort, DD1, DD3, DE096, DE098, Debio0406, Debio0512, Debio0615, Debio0618, Debio1036, Decaderm, Decadrale, Decadron, Decadronal, Decalon, Decan, Decason, Decdan, Decilone, Declophen, Decopen, Decorex, Decorten, Dedema, Dedron, Deexa, Defcort, De-flam, Deflamat, Deflan, Deflanil, Deflaren, Deflaz, deflazacort, Defnac, Defnalone, Defnil, Defosalic, Defsure, Defza, Dehydrocortison, Dekort, Delagil, delcasertib, delmitide, Delphicort, Deltacorsolone, Deltacortril, Deltafluorene, Deltasolone, Deltasone, Deltastab, Deltonin, Demarin, Demisone, Denebola, denileukin diftitox, denosumab, Denzo, Depocortin, Depo-medrol, Depomethotrexate, Depopred, Deposet, Depyrin, Derinase, Dermot, Dermolar, Dermonate, Dermosone, Dersone, Desketo, desonide, desoxycorticosterone acetate, Deswon, Dexa, Dexabene, Dexacip, Dexacort, Dexacortisone, Dexacotisil, Dexadic, Dexadrin, Dexadron, Dexafar, Dexahil, Dexalab, Dexalaf, Dexalet, Dexalgen, Dexallion, Dexalocal, Dexalone, Dexa-M, Dexamecortin, Dexamed, Dexamedis, Dexameral, Dexameta, Dexamethasone, dexamethasone acetate, dexamethasone palmitate, dexamethasone phosphate, dexamethasone sodium metasulfobenzoate, dexamethasone sodium phosphate, Dexamine, Dexapanthen, Dexa-S, Dexason, Dexatab, Dexatopic, Dexaval, Dexaven, Dexazolidin, Dexazona, Dexazone, Dexcor, Dexibu, dexibuprofen, Dexico, Dexifen, Deximune, dexketoprofen, dexketoprofen trometamol, Dexmark, Dexomet, Dexon I, Dexonalin, Dexonex, Dexony, Dexoptifen, Dexpin, Dextan-Plus, dextran sulfate, Dezacor, Dfz, diacerein, Diannexin, Diastone, Dicarol, Dicasone, Dicknol, Diclo, Diclobon, Diclobonse, Diclobonzox, Diclofast, Diclofen, diclofenac, diclofenac beta-dimethylaminoethanol, diclofenac deanol, diclofenac diethylamine, diclofenac epolamine, diclofenac potassium, diclofenac resinate, diclofenac sodium, Diclogen AGIO, Diclogen Plus, Diclokim, Diclomed, Diclo-NA, Diclonac, Dicloramin, Dicloran, Dicloreum, Diclorism, Diclotec, Diclovit, Diclowal, Diclozem, Dico P, Dicofen, Dicoliv, Dicorsone, Dicron, Dicser, Difena, Diffutab, diflunisal, dilmapimod, Dilora, dimethyl sulfone, Dinac, D-Indomethacin, Dioxaflex Protect, Dipagesic, Dipenopen, Dipexin, Dipro AS, Diprobeta, Diprobetasone, Diproklenat, Dipromet, Dipronova, Diprosone, Diprovate, Diproxen, Disarmin, Diser, Disopain, Dispain, Dispercam, Distamine, Dizox, DLT303, DLT404, DM199, DM99, DMI9523, dnaJP1, DNX02070, DNX04042, DNX2000, DNX4000, docosanol, Docz-6, Dolamide, Dolaren, Dolchis, Dolex, Dolflam, Dolfre, Dolgit, Dolmax, Dolmina, Dolo Ketazon, Dolobest, Dolobid, Doloc, Dolocam, Dolocartigen, Doloflt, Dolokind, Dolomed, Dolonac, Dolonex, Dolotren, Dolozen, Dolquine, Dom0100, Dom0400, Dom0800, Domet, Dometon, Dominadol, Dongipap, Donica, Dontisanin, doramapimod, Dorixina Relax, Dormelox, Dorzine Plus, Doxatar, Doxtran, DP NEC, DP4577, DP50, DP6221, D-Penamine, DPIV/APN Inhibitors, DR1 Inhibitors, DR4 Inhibitors, DRA161, DRA162, Drenex, DRF4848, DRL15725, Drossadin, DSP, Duexis, Duo-Decadron, Duoflex, Duonase, DV1079, DV1179, DWJ425, DWP422, Dymol, DYN15, Dynapar, Dysmen, E5090, E6070, Easy Dayz, Ebetrexat, EBI007, ECO286, EC0565, EC0746, Ecax, *Echinacea purpurea* extract, EC-Naprosyn, Econac, Ecosprin 300, Ecosprin 300, Ecridoxan, eculizumab, Edecam, efalizumab, Efcortesol, Effigel, Eflagen, Efridol, EGFR Antibody, EGS21, eIF5A1 siRNA, Ekarzin, elafin, Eldoflam, Elidel, Eliflam, Elisone, Elmes, Elmetacin, ELND001, ELND004, elocalcitol, Elocom, elsibucol, Emanzen, Emcort, Emifen, Emifenac, emorfazone, Empynase, emricasan, Emtor, Enable, Enbrel, Enceid, EncorStat, Encortolon, Encorton, Endase, Endogesic, Endoxan, Enkorten, Ensera, Entocort, Enzylan, Epanova, Eparang, Epatec, Epicotil, epidermal growth factor receptor 2 antibody, epidermal growth factor receptor antibody, Epidixone, Epidron, Epiklin, EPPA1, epratuzumab, EquiO, Erac, Erazon, ERB041, ERB196, Erdon, EryDex, *Escherichia coli* enterotoxin B subunit, Escin, E-Selectin Antagonists, Esfenac, ESN603, esonarimod, Esprofen, estetrol, Estopein, Estrogen Receptor beta agonist, etanercept, etaracizumab, ETC001, ethanol propolis extract, ETI511, etiprednol dicloacetate, Etodin, Etodine, Etodol, etodolac, Etody, etofenamate, Etol Fort, Etolac, Etopin, etoricoxib, Etorix, Etosafe, Etova, Etozox, Etura, Eucob, Eufans, eukaryotic translation initiation factor 5A oligonucleotide, Eunac, Eurocox, Eurogesic, everolimus, Evinopon, EVT401, Exaflam, EXEL9953, Exicort, Expen, Extra Feverlet, Extrapan, Extrauma, Exudase, F16, F991, Falcam, Falcol, Falzy, Farbovil, Farcomethacin, Farnerate, Farnezone, Farnezone, Farotrin, fas antibody, Fastflam, FasTRACK, Fastum, Fauldmetro, FcgammaRlA antibody, FE301, Febrofen, Febrofld, felbinac, Feldene, Feldex, Feloran, Felxicam, Fenac, Fenacop, Fenadol, Fenaflan, Fenamic, Fenaren, Fenaton, Fenbid, fenbufen, Fengshi Gutong, Fenicort, Fenopine, fenoprofen calcium, Fenopron, Fenris, Fensupp, Fenxicam, fepradinol, Ferovisc, Feverlet, fezakinumab, FG3019, FHT401, FHTCT4, FID114657, figitumumab, Filexi, filgrastim, Fillase, Final, Findoxin, fingolimod hydrochloride, firategrast, Firdapse, Fisiodar, Fivasa, FK778, Flacoxto, Fladalgin, Flagon, Flamar, Flamcid, Flamfort, Flamide, Flaminase, Flamirex Gesic, Flanid, Flanzen, Flaren, Flaren, Flash Act, Flavonoid Anti-inflammatory Molecule, Flebogamma DIF, Flenac, Flex, Flexafen 400, Flexi, Flexidol, Flexium, Flexon, Flexono, Flogene, Flogiatrin B12, Flogomin, Flogoral, Flogosan, Flogoter, Flo-Pred, Flosteron, Flotrip Forte, Flt3 inhibitors, fluasterone, Flucam, Flucinar, fludrocortisone acetate, flufenamate aluminum, flumethasone, Flumidon, flunixin, fluocinolone, fluocinolone acetonide, fluocinonide, fluocortolone, Fluonid, fluorometholone, Flur, flurbiprofen, Fluribec, Flurometholone, Flutal, fluticasone, fluticasone propionate, Flutizone, Fluzone, FM101 antibody, fms-related tyrosine kinase 1 antibody, Folitrax, fontolizumab, formic acid, Fortecortin, Fospeg, fostamatinib disodium, FP1069, FP13XX, FPA008, FPA031, FPT025, FR104, FR167653, Framebin, Frime, Froben, Frolix, FROUNT Inhibitors, Fubifen PAP, Fucole ibuprofen, Fulamotol, Fulpen, Fungifin, Furotalgin, fusidate sodium, FX002, FX141L, FX201, FX300, FX87L, Galectin modulators, gallium maltolate, Gamimune N, Gammagard, Gamma-I.V., GammaQuin, Gamma-Venin, Gamunex, Garzen, Gaspirin, Gattex, GBR500, GBR500 antibody, GBT009, G-CSF, GED0301, GED0414, Gefenec, Gelofen, Genepril, Gengraf, Genimune, Geniquin, Genotropin, Genz29155, Gerbin, Gerbin, gevokizumab, GF01564600, Gilenia, Gilenya, givinostat, GL0050, GL2045, glatiramer acetate, Globulin, Glortho Forte, Glovalox, Glovenin-I, GLPG0259, GLPG0555, GLPG0634, GLPG0778, GLPG0974, Gluco, Glucocerin, glucosamine, glucosamine hydrochloride, glucosamine sulfate, Glucotin, Gludex, Glutilage, GLY079, GLY145, Glycanic, Glycefort up, Glygesic, Glysopep, GMCSF Antibody, GMI1010, GMI1011, GMI1043, GMR321, GN4001, Goanna Salve, Goflex, gold sodium thiomalate, golimumab, GP2013, GPCR modulator, GPR15 Antagonist, GPR183 antagonist, GPR32 antagonist, GPR83 antagonist, G-protein Coupled Receptor Antagonists, Graceptor, Graftac, granulocyte colony-stimulating factor antibody, granulocyte-macrophage colony-stimulating factor antibody, Gravx, GRC4039, Grelyse, GS101, GS9973, GSC100, GSK1605786, GSK1827771, GSK2136525, GSK2941266, GSK315234, GSK681323, GT146, GT442, Gucixiaotong, Gufisera, Gupisone, gusperimus hydrochloride, GW274150, GW3333, GW406381, GW856553, GWB78, GXP04, Gynestrel, Haloart, halopredone acetate, Haloxin, HANALL, Harlan Soludacortin, Havisco, Hawon Bucillamin, HB802, HC31496, HCQ 200, HD104, HD203, HD205, HDAC inhibitor, HE2500, HE3177, HE3413, Hecoria, Hectomitacin, Hefasolon, Helen, Helenil, HemaMax, Hematom, hematopoietic stem cells, Hematrol, Hemner, Hemril, heparinoid, Heptax, HER2 Antibody, Herponil, hESC Derived Dendritic Cells, hESC Derived Hematopoietic stem cells, Hespercorbin, Hexacorton, Hexadrol, hexetidine, Hexoderm, Hexoderm Salic, HF0220, HF1020, HFT-401, hG-CSFR ED Fc, Hiberna, high mobility group box 1 antibody, Hiloneed, Hinocam, hirudin, Hirudoid, Hison, Histamine H4 Receptor Antagonist, Hitenercept, Hizentra, HL036, HL161, HMPL001, HMPL004, HMPL004, HMPL011, HMPL342, HMPL692, honey bee venom, Hongqiang, Hotemin, HPH116, HTI101, HuCAL Antibody, Human adipose mesenchymal stem cells, anti-MHC class II monoclonal antibody, Human Immunoglobulin, Human Placenta Tissue Hydrolysate, HuMaxCD4, HuMax-TAC, Humetone, Humicade, Humira, Huons Betamethasone sodium phosphate, Huons dexamethasone sodium phosphate, Huons Piroxicam, Huons Talniflumate, Hurofen, Huruma, Huvap, HuZAF, HX02, Hyalogel, hyaluronate sodium, hyaluronic acid, hyaluronidase, Hyaron, Hycocin, Hycort, Hy-Cortisone, hydrocortisone, hydrocortisone acetate, hydrocortisone butyrate, hydrocortisone hemisuccinate, hydrocortisone sodium phosphate, hydrocortisone sodium succinate, Hydrocortistab, Hydrocortone, Hydrolin, Hydroquine, Hydro-Rx, Hydrosone HIKMA, hydroxychloroquine, hydroxychloroquine sulfate, Hylase Dessau, HyMEX, Hypen, HyQ, Hysonate, HZN602, I.M.75, IAP Inhibitors, Ibalgin, Ibalgin, Ibex, ibrutinib, IBsolvMIR, Ibu, Ibucon, Ibudolor, Ibufen, Ibuflam, Ibuflex, Ibugesic, Ibu-Hepa, Ibukim, Ibumal, Ibunal, Ibupental, Ibupril, Ibuprof, ibuprofen, Ibuscent, Ibusoft, Ibusuki Penjeong, Ibususpen, Ibutard, Ibutop, Ibutop, Ibutrex, IC487892, ichthammol, ICRAC Blocker, IDEC131, IDECCE9.1, Ides, Idicin, Idizone, IDN6556, Idomethine, IDR1, Idyl SR, Ifen, iguratimod, IK6002, IKK-beta inhibitor, IL17 Antagonist, IL-17 Inhibitor, IL-17RC, IL18, IL1Hy1, IL1R1, IL-23 Adnectin, IL23 Inhibitor, IL23 Receptor Antagonist, IL-31 mAb, IL-6 Inhibitor, IL6Qb, Ilacox, Ilaris, ilodecakin, ILV094, ILV095, Imaxetil, IMD0560, IMD2560, Imesel Plus, Iminoral, Immodin, IMMU103, IMMU106, Immucept, Immufine, Immunex Syrup, immunoglobulin, immunoglobulin G, Immunoprin, ImmunoRel, Immurin, IMO8400, IMP731 antibody, Implanta, Imunocell, Imuran, Imurek, Imusafe, Imusporin, Imutrex, IN0701, Inal, INCB039110, INCB18424, INCB28050, INCB3284, INCB3344, Indexon, Indic, Indo, Indo-A, Indobid, Indo-Bros, Indocaf, Indocarsil, Indocid, Indocin, Indomehotpas, Indomen, Indomet, Indometacin, indomethacin, Indomethasone, Indometin, Indomin, Indopal, Indoron, Indotroxin, INDUS830, INDUS83030, Infladase, Inflamac, Inflammasome inhibitor, Inflavis, Inflaxen, Inflectra, infliximab, Ingalipt, Inicox dp, Inmecin, Inmunoartro, Innamit, InnoD06006, INO7997, Inocin, Inoten, Inovan, Inpra, Inside Pap, Insider-P, Instacyl, Instracool, Intafenac, Intaflam, Inteban, Inteban Spansule, integrin, alpha 1 antibody, integrin, alpha 2 antibody, Intenurse, interferon alfa, interferon beta-1a, interferon gamma, interferon gamma antibody, Interking, interleukin 1 Hy1, interleukin 1 antibody, interleukin 1 receptor antibody, interleukin 1, beta antibody, interleukin 10, interleukin 10 antibody, interleukin 12, interleukin 12 antibody, interleukin 13 antibody, interleukin 15 antibody, interleukin 17 antibody, interleukin 17 receptor C, interleukin 18, interleukin 18 binding protein, interleukin 18 antibody, interleukin 2 receptor, alpha antibody, interleukin 20 antibody, Interleukin 21 mAb, interleukin 23 aptamer, interleukin 31 antibody, interleukin 34, Interleukin 6 Inhibitor, interleukin 6 antibody, interleukin 6 receptor antibody, interleukin 7, interleukin 7 receptor antibody, interleukin 8, interleukin 8 antibody, interleukin-18 antibody, Intidrol, Intradex, Intragam P, Intragesic, Intraglobin F, Intratect, Inzel, Iomab B, IOR-T3, IP751, IPH2201, IPH2301, IPH24, IPH33, IPI145, Ipocort, IPP201007, I-Profen, Iprox, Ipson, Iputon, IRAK4 Inhibitor, Iremod, Irtonpyson, IRX3, IRX5183, ISA247, ISIS104838, ISIS2302, ISISCRPRx, Ismafron, IsoQC inhibitor, Isox, ITF2357, Iveegam EN, Ivepred, IVIG-SN, IWOOL Izilox, J607Y, J775Y, JAK Inhibitor, JAK3 inhibitor, JAK3 kinase inhibitor, JI3292, JI4135, Jinan Lida, JNJ10329670, JNJ18003414, JNJ26528398, JNJ27390467, JNJ28838017, JNJ31001958, JNJ38518168, JNJ39758979, JNJ40346527, JNJ7777120, JNT-Plus, Joflam, Joint Glucosamin, Jointec, Jointstem, Joinup, JPE1375, JSM10292, JSM7717, JSM8757, JTE051, JTE052, JTE522, JTE607, Jusgo, K412, K832, Kaflam, KAHR101, KAHR102, KAI9803, Kalymin, Kam Predsol, Kameton, KANAb071, Kappaproct, KAR2581, KAR3000, KAR3166, KAR4000, KAR4139, KAR4141, KB002, KB003, KD7332, KE298, keliximab, Kemanat, Kemrox, Kenacort, Kenalog, Kenaxir, Kenketsu Venoglobulin-IH, Keplat, Ketalgipan, Keto Pine, Keto, Ketobos, Ketofan, Ketofen, Ketolgan, Ketonal, Ketoplus Kata Plasma, ketoprofen, Ketores, Ketorin, ketorolac, ketorolac tromethamine, Ketoselect, Ketotop, Ketovail, Ketricin, Ketroc, Ketum, Keyi, Keyven, KF24345, K-Fenac, K-Fenak, K-Gesic, Kifadene, Kilcort, Kildrol, KIM127, Kimotab, Kinase Inhibitor 4SC, Kinase N, Kincort, Kindorase, Kineret, Kineto, Kitadol, Kitex, Kitolac, KLK1 Inhibitor, Klofen-L, Klotaren, KLS-40or, KLS-40ra, KM277, Knavon, Kodolo orabase, Kohakusanin, Koide, Koidexa, Kolbet, Konac, Kondro, Kondromin, Konshien, Kontab, Kordexa, Kosa, Kotase, KPE06001, KRP107, KRP203, KRX211, KRX252, KSB302, K-Sep, Kv 1.3 Blocker, Kv1.3 4SC, Kv1.3 inhibitor, KVK702, Kynol, L156602, Labizone, Labohydro, Labopen, Lacoxa, Lamin, Lamit, Lanfetil, laquinimod, larazotide acetate, LAS186323, LAS187247, LAS41002, Laticort, LBEC0101, LCP3301, LCP-Siro, LCP-Tacro, LCsA, LDP392, Leap-S, Ledercort, Lederfen, Lederlon, Lederspan, Lefenine, leflunomide, Leflux, Lefno, Lefra, Leftose, Lefumide, Lefunodin, Lefva, lenalidomide, lenercept, LentiRA, LEO15520, Leodase, Leukine, Leukocyte function-associated antigen-1 antagonist, leukocyte immunoglobulin-like receptor, subfamily A, member 4 antibody, Leukothera, leuprolide acetate, levalbuterol, levomenthol, LFA-1 Antagonist, LFA451, LFA703, LFA878, LG106, LG267 Inhibitors, LG688 Inhibitors, LGD5552, Li Life, LidaMantle, Lidex, lidocaine, lidocaine hydrochloride, Lignocaine hydrochloride, LIM0723, LIM5310, Limethason, Limus, Limustin, Lindac, Linfonex, Linola acute, Lipcy, lisofylline, Listran, Liver X Receptor modulator, Lizak, LJP1207, LJP920, Lobafen, Lobu, Locafluo, Localyn, Locaseptil-Neo, Locpren, Lodine, Lodotra, Lofedic, Loflam, Lofnac, Lolcam, Lonac, lonazolac calcium, Loprofen, Loracort, Lorcam, Lorfenamin, Lorinden Lotio, Lorncrat, lornoxicam, Lorox, losmapimod, loteprednol etabonate, Loteprednol, Lotirac, Low Molecular *Ganoderma Lucidum* Polysaccharide, Loxafen, Loxfenine, Loxicam, Loxofen, Loxonal, Loxonin, loxoprofen sodium, Loxoron, LP183A1, LP183A2, LP204A1, LPCN1019, LT1942, LT1964, LTNS101, LTNS103, LTNS106, LTNS108, LTS1115, LTZMP001, Lubor, lumiracoxib, Lumitect, LX2311, LX2931, LX2932, LY2127399, LY2189102, LY2439821, LY294002, LY3009104, LY309887, LY333013, lymphocyte activation gene 3 antibody, Lymphoglobuline, Lyser, lysine aspirin, Lysobact, Lysoflam, Lysozyme hydrochloride, M3000, M834, M923, mAb hG-CSF, MABP1, macrophage migration inhibitory factor antibody, Maitongna, Majamil prolongatum, major histocompatibility complex class II DR antibody, major histocompatibility complex class II antibody, Malidens, Malival, mannan-binding lectin, mannan-binding lectin-associated serine protease-2 antibody, MapKap Kinase 2 Inhibitor, maraviroc, Marlex, masitinib, Maso, MASP2 antibody, MAT304, Matrix Metalloprotease Inhibitor, mavrilimumab, Maxiflam, Maxilase, Maximus, Maxisona, Maxius, Maxpro, Maxrel, Maxsulid, Maxyl2, Maxy30, MAXY4, Maxy735, Maxy740, Mayfenamic, MB 11040, MBPY003b, MCAF5352A, McCam, McRofy, MCS18, MD707, MDAM, MDcort, MDR06155, MDT012, Mebicam, Mebuton, meclofenamate sodium, Meclophen, Mecox, Medacomb, Medafen, Medamol, Medesone, MEDI2070, MEDI5117, MEDI541, MEDI552, MEDI571, Medicox, Medifen, Medisolu, Medixon, Mednisol, Medrol, Medrolon, medroxyprogesterone acetate, Mefalgin, mefenamic acid, Mefenix, Mefentan, Meflen, Mefnetra forte, Meftagesic-DT, Meftal, Megakaryocyte Growth and Development Factor, Megaspas, Megaster, megestrol acetate, Meite, Meksun, Melbrex, Melcam, Melcam, Melflam, Melic, Melica, Melix, Melocam, Melocox, Mel-One, Meloprol, Melosteral, Melox, Meloxan, Meloxcam, Meloxic, Meloxicam, Meloxifen, Meloxin, Meloxiv, Melpred, Melpros, Melurjin, Menamin, Menisone, Menthomketo, Menthoneurin, Mentocin, Mepa, Mepharen, meprednisone, Mepresso, Mepsolone, mercaptopurine, Mervan, Mesadoron, mesalamine, Mesasal, Mesatec, Mesenchymal Precursor Cells, mesenchymal stem cell, Mesipol, Mesren, Mesulan, Mesulid, Metacin, Metadaxan, Metaflex, Metalcaptase, metalloenzyme inhibitors, Metapred, Metax, Metaz, Meted, Metedic, Methacin, tors, Metapred, Methasone, Methotrax, methotrexate, methotrexate sodium, Methpred, Methyl prednisolone acetate, methyl salicylate, methyl sulphonyl methane, Methylon, Methylpred, methylprednisolone, methylprednisolone acetate, methylprednisolone sodium succinate, methylprednisolone succinate, Methylprednisolone, Methysol, Metindol, Metoart, Metoject, Metolate, Metoral, Metosyn, Metotab, Metracin, Metrex, metronidazole, Metypred, Mevamox, Mevedal, Mevilox, Mevin SR, Mexilal, Mexpharm, Mext, Mextran, MF280, M-FasL, MHC class II beta chain peptide, Micar, Miclofen, Miclofenac, Micofenolato Mofetil, Micosone, Microdase, microRNA 181 a-2 oligonucleotide, MIF Inhibitors, MIFQb, MIKA-Ketoprofen, Mikametan, milodistim, Miltax, Minafen, Minalfen, Minalfene, Minesulin, Minocort, Mioflex, Miolox, Miprofen, Miridacin, Mirloks, Misoclo, Misofenac, MISTB03, MISTB04, Mitilor, mizoribine, MK0359, MK0812, MK0873, MK2 Inhibitors, MK50, MK8457, MK8808, MKC204, MLN0002, MLN0415, MLN1202, MLN273, MLN3126, MLN3701, MLN3897, MLNM002, MM093, MM7XX, MN8001, Mobic, Mobicam, Mobicox, Mobifen Plus, Mobilat, Mobitil, Mocox, Modigraf, Modrasone, Modulin, Mofecept, Mofetyl, mofezolac sodium, Mofilet, Molace, molgramostim, Molslide, Momekin, Momen Gele, Moment 100, Momesone, Momesun, Mometamed, mometasone, mometasone furoate, Monimate, monosodium alpha-luminol, Mopik, MOR103, MOR104, MOR105, MOR208 antibody, MORAb022, Moricam, morniflumate, Mosuolit, Motoral, Movaxin, Mover, Movex, Movix, Movoxicam, Mox Forte, Moxen, moxifloxacin hydrochloride, Mozobil, MP, MP0210, MP0270, MP1000, MP1031, MP196, MP435, MPA, mPGES-1 inhibitor, MPSS, MRX7EAT, MSL, MT203, MT204, mTOR Inhibitor, MTRX1011A, Mucolase, Multicort, MultiStem, muramidase, muramidase, muramidase hydrochloride, muromonab-CD3, Muslax, Muspinil, Mutaze, Muvera, MX68, Mycept, Mycocell, Mycocept, Mycofenolatmofetil Actavis, Mycofet, Mycofit, Mycolate, Mycoldosa, Mycomun, Myconol, mycophenolate mofetil, mycophenolate sodium, mycophenolic acid, Mycotil, myeloid progenitor cells, Myfenax, Myfetil, Myfortic, Mygraft, Myochrysine, Myocrisin, Myprodol, Mysone, nab-Cyclosporine, Nabentac, nabiximols, Nabton, Nabuco, Nabucox, Nabuflam, Nabumet, nabumetone, Nabuton, Nac Plus, Nacta, Nacton, Nadium, Naklofen SR, NAL1207, NAL1216, NAL1219, NAL1268, NAL8202, Nalfon, Nalgesin S, namilumab, Namsafe, nandrolone, Nanocort, Nanogam, Nanosomal Tacrolimus, Napageln, Napilac, Naprelan, Napro, Naprodil, Napronax, Napropal, Naproson, Naprosyn, Naproval, Naprox, naproxen, naproxen sodium, Naproxin, Naprozen, Narbon, Narexsin, Naril, Nasida, natalizumab, Naxdom, Naxen, Naxin, Nazovel, NC2300, ND07, NDC01352, Nebumetone, NecLipGCSF, Necsulide, Necsunim, Nelsid-S, Neo Clobenate, Neo Swiflox FC, Neocoflan, Neo-Drol, Neo-Eblimon, Neo-Hydro, Neoplanta, Neoporine, Neopreol, Neoprox, Neoral, Neotrexate, Neozen, Nepra, Nestacort, Neumega, Neupogen, Neuprex, Neurofenac, Neurogesic, Neurolab, Neuroteradol, Neuroxicam, Neutalin, neutrazumab, Neuzym, New Panazox, Newfenstop, NewGam, Newmafen, Newmatal, Newsicam, NEX1285, sFcRIIB, Nextomab, NF-kappaB Inhibitor, NF-kB inhibitor, NGD20001, NHP554B, NHP554P, NI0101 antibody, NI0401, NI0501 antibody, NI0701, NI071, NI1201 antibody, NI1401, Nicip, Niconas, Nicool, NiCord, Nicox, Niflumate, Nigaz, Nikam, Nilitis, Nimace, Nimaid, Nimark-P, Nimaz, Nimcet Juicy, Nime, Nimed, Nimepast, nimesulide, Nimesulix, Nimesulon, Nimica Plus, Nimkul, Nimlin, Nimnat, Nimodol, Nimpidase, Nimsaid-S, Nimser, Nimsy-SP, Nimupep, Nimusol, Nimutal, Nimuwin, Nimvon-S, Nincort, Niofen, Nipan, Nipent, Nise, Nisolone, Nisopred, Nisoprex, Nisulid, nitazoxanide, Nitcon, nitric oxide, Nizhvisal B, Nizon, NL, NMR1947, NN8209, NN8210, NN8226, NN8555, NN8765, NN8828, NNC014100000100, NNC051869, Noak, Nodevex, Nodia, Nofenac, Noflagma, Noflam, Noflamen, Noflux, Non-antibacterial Tetracyclines, Nonpiron, Nopain, Normferon, Notpel, Notritis, Novacort, Novagent, Novarin, Novigesic, NOXA12, NOXD19, Noxen, Noxon, NPI1302a-3, NPI1342, NPI1387, NPI1390, NPRCS1, NPRCS2, NPRCS3, NPRCS4, NPRCS5, NPRCS6, NPS3, NPS4, nPT-ery, NU3450, nuclear factor NF-kappa-B p65 subunit oligonucleotide, Nucort, Nulojix, Numed-Plus, Nurokind Ortho, Nusone-H, Nutrikemia, Nuvion, NV07alpha, NX001, Nyclobate, Nyox, Nysa, Obarcort, OC002417, OC2286, ocaratuzumab, OCTSG815, Oedemase, Oedemase-D, ofatumumab, Ofgyl-O, Ofvista, OHR118, OKi, Okifen, Oksamen, Olai, olokizumab, Omeprose E, Omnacortil, Omneed, Omniclor, Omnigel, Omniwel, onercept, ONO4057, ONS1210, ONS1220, Ontac Plus, Ontak, ONX0914, OPC6535, opebacan, OPN101, OPN201, OPN302, OPN305, OPN401, oprelvekin, OPT66, Optifer, Optiflur, OptiMIRA, Orabase Hca, Oradexon, Oraflex, OralFenac, Oralog, Oralpred, Ora-sed, Orasone, orBec, Orbone forte, Orcl, ORE10002, ORE10002, Orencia, Org214007, Org217993, Org219517, Org223119, Org37663, Org39141, Org48762, Org48775, Orgadrone, Ormoxen, Orofen Plus, Oromylase Biogaran, Orthal Forte, Ortho Flex, Orthoclone OKT3, Orthofen, Orthoflam, Orthogesic, Orthoglu, Ortho-II, Orthomac, Ortho-Plus, Ortinims, Ortofen, Orudis, Oruvail, OS2, Oscart, Osmetone, Ospain, Ossilife, Ostelox, Osteluc, Osteocerin, osteopontin, Osteral, otelixizumab, Otipax, Ou Ning, OvaSave, OX40 Ligand Antibody, Oxa, Oxagesic CB, Oxalgin DP, oxaprozin, OXCQ, Oxeno, Oxib MD, Oxibut, Oxicam, Oxiklorin, Oximal, Oxynal, oxyphenbutazone, Oxyphenbutazone, ozoralizumab, P13 peptide, P1639, P21, P2X7 Antagonists, p38 Alpha Inhibitor, p38 Antagonist, p38 MAP kinase inhibitor, p38alpha MAP Kinase Inhibitor, P7 peptide, P7170, P979, PA401, PA517, Pabi-dexamethasone, PAC, PAC10649, paclitaxel, Painoxam, Paldon, Palima, pamapimod, Pamatase, Panafcort, Panafcortelone, Panewin, PanGraf, Panimun Bioral, Panmesone, Panodin SR, Panslay, Panzem, Panzem NCD, PAP1, papain, Papirzin, Pappen K Pap, Paptinim-D, paquinimod, PAR2 Antagonist, Paracetamol, Paradic, Parafen TAJ, Paramidin, Paranac, Parapar, Parci, parecoxib, Parixam, Parry-S, Partaject Busulfan, pateclizumab, Paxceed, PBI0032, PBI1101, PBI1308, PBI1393, PBI1607, PBI1737, PBI2856, PBI4419, PBI4419, P-Cam, PCI31523, PCI32765, PCI34051, PCI45261, PCI45292, PCI45308, PD360324, PD360324, PDA001, PDE4 inhibitor, PDE-IV Inhibitor, PDL241 antibody, PDL252, Pediapred, Pefree, pegacaristim, Peganix, Peg-Interleukin 12, pegsunercept, Pegsunercept, PEGylated arginine deiminase, peldesine, pelubiprofen, Penacle, penicillamine, Penostop, Pentalgin, Pentasa, Pentaud, pentostatin, Peon, Pepdase, Pepser, Peptirase, Pepzen, Pepzol, Percutalgine, Periochip, Peroxisome Proliferator Activated Receptor gamma modulators, Petizene, PF00344600, PF04171327, PF04236921, PF04308515, PF05230905, PF05280586, PF251802, PF3475952, PF3491390, PF3644022, PF4629991, PF4856880, PF5212367, PF5230896, PF547659, PF755616, PF9184, PG27, PG562, PG760564, PG8395, PGE3935199, PGE527667, PHS, PH797804, PHA408, Pharmaniaga Mefenamic acid, Pharmaniaga Meloxicam, Pheldin, Phenocept, phenylbutazone, PHY702, PI3K delta inhibitor, PI3K Gamma/Delta Inhibitor, PI3K Inhibitor, Picalm, pidotimod, piketoprofen, Pilelife, Pilopil, Pilovate, pimecrolimus, Pipethanen, Piractam, Pirexyl, Pirobet, Piroc, Pirocam, Pirofel, Pirogel, Piromed, Pirosol, Pirox, Piroxen, Piroxicam, piroxicam betadex, Piroxifar, Piroxil, Piroxim, Pixim, Pixykine, PKC Theta Inhibitor, PL3100, PL5100 Diclofenac, Placenta Polypeptide, Plaquenil, plerixafor, Plocfen, PLR14, PLR18, Plutin, PLX3397, PLX5622, PLX647, PLX-BMT, pms-Diclofenac, pms-Ibuprofen, pms-Leflunomide, pms-Meloxicam, pms-Piroxicam, pms-Prednisolone, pms-Sulfasalazine, pms-Tiaprofenic, PMX53, PN0615, PN100, PN951, podofilox, POL6326, Polcortolon, Polyderm, Polygam S/D, Polyphlogin, Poncif, Ponstan, Ponstil Forte, Porine-A Neoral, Potaba, potassium aminobenzoate, Potencort, Povidone, povidone iodine, pralnacasan, Prandin, Prebel, Precodil, Precortisyl Forte, Precortyl, Predfoam, Predicort, Predicorten, Predilab, Predilone, Predmetil, Predmix, Predna, Prednesol, Predni, prednicarbate, Prednicort, Prednidib, Prednifarma, Prednilasca, prednisolone, prednisolone acetate, prednisolone sodium phosphate, prednisolone sodium succinate, prednisolone sodium succinate, prednisone, prednisone acetate, Prednitop, Prednol-L, Prednox, Predone, Predonema, Predsol, Predsolone, Predsone, Predval, Preflam, Prelon, Prenaxol, Prenolone, Preservex, Preservin, Presol, Preson, Prexige, Priliximab, Primacort, Primmuno, Primofenac, prinaberel, Privigen, Prixam, Probuxil, Procarne, Prochymal, Procider-EF, Proctocir, Prodase, Prodel B, Prodent, Prodent Verde, Proepa, Profecom, Profenac L, Profenid, Profenol, Proflam, Proflex, Progesic Z, proglumetacin, proglumetacin maleate, Prograf, Prolase, Prolixan, promethazine hydrochloride, Promostem, Promune, PronaB, pronase, Pronat, Prongs, Pronison, Prontoflam, Propaderm-L, Propodezas, Propolisol, Proponol, propyl nicotinate, Prostaloc, Prostapol, Protacin, Protase, Protease Inhibitors, Protectan, Proteinase Activated Receptor 2 Inhibitor, Protofen, Protrin, Proxalyoc, Proxidol, Proxigel, Proxil, Proxym, Prozym, PRT062070, PRT2607, PRTX100, PRTX200, PRX106, PRX167700, Prysolone, PS031291, PS375179, PS386113, PS540446, PS608504, PS826957, PS873266, Psorid, PT, PT17, PTL101, P-Transfer Factor peptides, PTX3, Pulminiq, Pulsonid, Purazen, Pursin, PVS40200, PX101, PX106491, PX114, PXS2000, PXS2076, PYM60001, Pyralvex, Pyranim, pyrazinobutazone, Pyrenol, Pyricam, Pyrodex, Pyroxi-Kid, QAX576, Qianbobiyan, QPI1002, QR440, qT3, Quiacort, Quidofil, R107s, R125224, R1295, R132811, R1487, R1503, R1524, R1628, R333, R348, R548, R7277, R788, rabeximod, Radix Isatidis, Radofen, Raipeck, Rambazole, Randazima, Rapacan, Rapamune, Raptiva, Ravax, Rayos, RDEA119, RDEA436, RDP58, Reactine, Rebif, REC200, Recartix-DN, receptor for advanced glycation end products antibody, Reclast, Reclofen, recombinant HSA-TIMP-2, recombinant human alkaline Phosphatase, recombinant Interferon Gamma, Recominant human alkaline phosphatase, Reconil, Rectagel HC, Recticin, Recto Menaderm, Rectos, Redipred, Redolet, Refastin, Regenica, REGN88, Relafen, Relaxib, Relev, Relex, Relifen, Relifex, Relitch, Rematof, remestemcel-1, Remesulidum, Remicade, Remsima, Remsima, Remsima, ReN1869, Renacept, Renfor, Renodapt, Renodapt-S, Renta, Reosan, Repare-AR, Reparilexin, reparixin, Repertaxin, Repisprin, Resochin, Resol, resolvin E1, Resurgil, Re-tin-colloid, Retoz, Reumacap, Reumacon, Reumadolor, Reumador, Reumanisal, Reumazin, Reumel, Reumotec, Reuquinol, revamilast, Revascor, Reviroc, Revlimid, Revmoksikam, Rewalk, Rexalgan, RG2077, RG3421, RG4934 antibody, RG7416, RG7624, Rheila, Rheoma, Rheprox, Rheudenolone, Rheufen, Rheugesic, Rheumacid, Rheumacort, Rheumatrex, Rheumesser, Rheumid, Rheumon, Rheumox, Rheuoxib, Rhewlin, Rhucin, RhuDex, Rhulef, Ribox, Ribunal, Ridaura, rifaximin, rilonacept, rimacalib, Rimase, Rimate, Rimatil, Rimesid, risedronate sodium, Ritamine, Rito, Rituxan, rituximab, RNS60, RO1138452, Ro313948, RO3244794, RO5310074, Rob803, Rocamix, Rocas, Rofeb, rofecoxib, Rofee, Rofewal, Roficip Plus, Rojepen, Rokam, Rolodiquim, Romacox Fort, Romatim, romazarit, Ronaben, ronacaleret, Ronoxcin, ROR Gamma T Antagonist, ROR gamma t inverse agonists, Rosecin, rosiglitazone, Rosmarinic acid, Rotan, Rotec, Rothacin, Roxam, Roxib, Roxicam, Roxopro, Roxygin DT, RP54745, RPI78, RPI78M, RPI78MN, RPIMN, RQ00000007, RQ00000008, RTA402, R-Tyflam, Rubicalm, Rubifen, Ruma pap, Rumalef, Rumidol, Rumifen, Runomex, rusalatide acetate, ruxolitinib, RWJ445380, RX10001, Rycloser MR, Rydol, S1P Receptor Agonists, S1P Receptor Modulators, S1P1 Agonist, S1P1 receptor agonist, 52474, 53013, SA237, SA6541, Saaz, S-adenosyl-L-methionine-sulfate-p-toluene sulfonate, Sala, Salazidin, Salazine, Salazopyrin, Salcon, Salicam, salsalate, Sameron, SAN300, Sanaven, Sandimmun, Sandoglobulin, Sanexon, SangCya, SAR153191, SAR302503, SAR479746, Sarapep, sargramostim, Sativex, Savantac, Save, Saxizon, Sazo, SB1578, SB210396, SB217969, SB242235, SB273005, SB281832, SB683698, SB751689, SBI087, SC080036, SC12267, SC409, Scaflam, SCD ketoprofen, SCI0323, SCIO469, SD-15, SD281, SDP051 antibody, Sd-rxRNA, secukinumab, Sedase, Sedilax, Sefdene, Seizyme, SEL113, Seladin, Selecox, selectin P ligand antibody, Glucocorticoid Receptor Agonist, Selectofen, Selektine, SelK1 antibody, Seloxx, Selspot, Selzen, Selzenta, Selzentry, semapimod, semapimod hydrochloride, semparatide, Semparatide, Senafen, Sendipen, Senterlic, SEP119249, Sepdase, Septirose, Seractil, Serafen-P, Serase, Seratid D, Seratiopeptidase, Serato-M, Seratoma Forte, Serazyme, Serezon, Sero, Serodase, Serpicam, Serra, serrapeptase, Serratin, Serratiopeptidase, Serrazyme, Servisone, Seven E P, SGI1252, SGN30, SGN70, SGX203, shark cartilage extract, Sheril, Shield, Shifazen, Shifazen-Fort, Shincort, Shincort, Shiosol, ShK186, Shuanghuangxiaoyan, SI615, SI636, Sigmasporin, Sigmasporin, SIM916, Simpone, Simulect, Sinacort, Sinalgia, Sinapol, Sinatrol, Sinsia, siponimod, Sirolim, sirolimus, Siropan, Sirota, Sirova, sirukumab, Sistal Forte, SKF105685, SKF105809, SKF106615, SKF86002, Skinalar, Skynim, Skytrip, SLAM family member 7 antibody, Slo-indo, SM101, SM201 antibody, SM401, SMAD family member 7 oligonucleotide, SMART Anti-IL-12 Antibody, SMP114, SNO030908, SNO070131, sodium aurothiomalate, sodium chondroitin sulfate, sodium deoxyribonucleotide, sodium gualenate, sodium naproxen, sodium salicylate, Sodixen, Sofeo, Soleton, Solhidrol, Solicam, Soliky, Soliris, Sol-Melcort, Solomet, Solondo, Solone, Solu-Cort, Solu-Cortef, Solu-Decortin H, Solufen, Solu-Ket, Solumark, Solu-Medrol, Solupred, Somalgen, somatropin, Sonap, Sone, sonepcizumab, Sonexa, Sonim, Sonim P, Soonil, Soral, Sorenil, sotrastaurin acetate, SP-10, SP600125, Spanidin, SP-Cortil, SPD550, Spedace, sperm adhesion molecule 1, Spictol, spleen tyrosine kinase oligonucleotide, Sporin, S-prin, SPWF1501, SQ641, SQ922, SR318B, SR9025, SRT2104, SSR150106, SSR180575, SSSO7 antibody, ST1959, STA5326, stabilin 1 antibody, Stacort, Stalogesic, stanozolol, Staren, Starmelox, Stedex IND-SWIFT, Stelara, Stemin, Stenirol, Sterapred, Steriderm S, Steno, Sterisone, Steron, stichodactyla helianthus peptide, Stickzenol A, Stiefcortil, Stimulan, STNM01, Store Operated Calcium Channel (SOCC) Modulator, STP432, STP900, Stratasin, Stridimmune, Strigraf, SU Medrol, Subreum, Subuton, Succicort, Succimed, Sulan, Sulcolon, Sulfasalazin Heyl, Sulfasalazin, sulfasalazine, Sulfovit, Sulidac, Sulide, sulindac, Sulindex, Sulinton, Sulphafine, Sumilu, SUN597, Suprafen, Supretic, Supsidine, Surgam, Surgamine, Surugamu, Suspen, Suton, Suvenyl, Suwei, SW Dexasone, Syk Family Kinase Inhibitor, Syn1002, Synacran, Synacthen, Synalar C, Synalar, Synavive, Synercort, Sypresta, T cell cytokine-inducing surface molecule antibody, T cell receptor antibody, T5224, T5226, TA101, TA112, TA383, TA5493, tabalumab, Tacedin, Tacgraf, TACIFc5, Tacrobell, Tacrograf, Tacrol, tacrolimus, Tadekinig alpha, Tadolak, TAFA93, Tafirol Artro, Taizen, TAK603, TAK715, TAK783, Takfa, Taksta, talarozole, Talfin, Talmain, talmapimod, Talmea, Talnif, talniflumate, Talos, Talpain, Talumat, Tamalgen, Tamceton, Tamezon, Tandrilax, tannins, Tannosynt, Tantum, tanzisertib, Tapainbeta, Tapoein, Tarenac, tarenflurbil, Tarimus, Tarproxen, Tauxib, Tazomust, TBR652, TC5619, T-cell, immune regulator 1, ATPase, H+ transporting, lysosomal V0 subunit A3 antibody, TCK1, T-cort, T-Dexa, Tecelac, Tecon, teduglutide, Teecort, Tegeline, Tementil, temoporfin, Tencam, Tendrone, Tenefuse, Tenfly, tenidap sodium, Tenocam, Tenoflex, Tenoksan, Tenotil, tenoxicam, Tenoxim, Tepadina, Teracort, Teradol, tetomilast, TG0054, TG1060, TG20, TG20, tgAAC94, Th1/Th2 Cytokine Synthase Inhibitor, Th-17 cell inhibitors, Thalido, thalidomide, Thalomid, Themisera, Thenil, Therafectin, Therapyace, thiarabine, Thiazolopyrimidines, thioctic acid, thiotepa, THR090717, THR0921, Threenofen, Thrombate III, Thymic peptide, Thymodepressin, Thymogam, Thymoglobulin, Thymoglobuline, Thymoject thymic peptides, thymomodulin, thymopentin, thymopolypetides, tiaprofenic acid, tibezonium iodide, Ticoflex, tilmacoxib, Tilur, T-immune, Timocon, Tiorase, Tissop, TKB662, TL011, TLR4 antagonists, TLR8 inhibitor, TM120, TM400, TMX302, TNF Alpha inhibitor, TNF alpha-TNF receptor antagonist, TNF antibody, TNF receptor superfamily antagonists, TNF TWEAK Bi-Specific, TNF-Kinoid, TNFQb, TNFR1 antagonist, TNR001, TNX100, TNX224, TNX336, TNX558, tocilizumab, tofacitinib, Tokuhon happ, TOL101, TOL102, Tolectin, ToleriMab, Tolerostem, Tolindol, toll-like receptor 4 antibody, toll-like receptor antibody, tolmetin sodium, Tongkeeper, Tonmex, Topflame, Topicort, Topleucon, Topnac, Toppin Ichthammol, toralizumab, Toraren, Torcoxia, Toroxx, Tory, Toselac, Totaryl, Touch-med, Touchron, Tovok, Toxic apis, Toyolyzom, TP4179, TPCA1, TPI526, TR14035, Tradil Fort, Traficet-EN, Tramace, tramadol hydrochloride, tranilast, Transimune, Transporina, Tratul, Trexall, Triacort, Triakort, Trialon, Triam, triamcinolone, triamcinolone acetate, triamcinolone acetonide, triamcinolone acetonide acetate, triamcinolone hexacetonide, Triamcort, Triamsicort, Trianex, Tricin, Tricort, Tricortone, TricOs T, Triderm, Trilac, Trilisate, Trinocort, Trinolone, Triolex, triptolide, Trisfen, Trivaris, TRK170, TRK530, Trocade, trolamine salicylate, Trolovol, Trosera, Trosera D, Troycort, TRX1 antibody, TRX4, Trymoto, Trymoto-A, TT301, TT302, TT32, TT32, TT33, TTI314, tumor necrosis factor, tumor necrosis factor 2-methoxyethyl phosphorothioate oligonucleotide, tumor necrosis factor antibody, tumor necrosis factor kinoid, tumor necrosis factor oligonucleotide, tumor necrosis factor receptor superfamily, member 1B antibody, tumor necrosis factor receptor superfamily1B oligonucleotide, tumor necrosis factor superfamily, member 12 antibody, tumor necrosis factor superfamily, member 4 antibody, tumor protein p53 oligonucleotide, tumour necrosis factor alpha antibody, TuNEX, TXA127, TX-RAD, TYK2 inhibitors, Tysabri, ubidecarenone, Ucerase, ulodesine, Ultiflam, Ultrafastin, Ultrafen, Ultralan, U-Nice-B, Uniplus, Unitrexate, Unizen, Uphaxicam, UR13870, UR5269, UR67767, Uremol-HC, Urigon, U-Ritis, ustekinumab, V85546, Valcib, Valcox, valdecoxib, Valdez, Valdixx, Valdy, Valentac, Valoxib, Valtune, Valus AT, Valz, Valzer, Vamid, Vantal, Vantelin, VAP-1 SSAO Inhibitor, vapaliximab, varespladib methyl, Varicosin, Varidase, vascular adhesion protein-1 antibody, VB110, VB120, VB201, VBY285, Vectra-P, vedolizumab, Vefren, VEGFR-1 Antibody, Veldona, veltuzumab, Vendexine, VenimmunN, Venoforte, Venoglobulin-IH, Venozel, Veral, Verax, vercirnon, vero-Dexamethasone, VeroKladribin, Vetazone, VGX1027, VGX750, Vibex MTX, vidofludimus, Vifenac, Vimovo, Vimultisa, Vincort, Vingraf, Vioform-HC, Vioxl, Vioxx, Virobron, visilizumab, Vivaglobin, Vivalde Plus, Vivian-A, VLST002, VLST003, VLST004, VLST005, VLST007, Voalla, voclosporin, Vokam, Vokmor, Volmax, Volna-K, Voltadol, Voltagesic, Voltanase, Voltanec, Voltaren, Voltarile, Voltic, Voren, vorsetuzumab, Votan-SR, VR909, VRA002, VRP1008, VRS826, VRS826, VT111, VT214, VT224, VT310, VT346, VT362, VTX763, Vurdon, VX30 antibody, VX467, VXS, VX509, VX702, VX740, VX745, VX745, VX850, W54011, Walacort, Walix, WC3027, Wilgraf, Winflam, Winmol, Winpred, Winsolve, Wintogeno, WIP901, Woncox, WSB711 antibody, WSB712 antibody, WSB735, WSB961, X071NAB, X083NAB, Xantomicin Forte, Xedenol, Xefo, Xefocam, Xenar, Xepol, X-Flam, Xibra, Xicam, Xicotil, Xifaxan, XL499, XmAb5483, XmAb5485, XmAb5574, XmAb5871, XOMA052, Xpress, XPro1595, XtendTNF, XTo11, Xtra, Xylex-H, Xynofen SR, Yang Shu-IVIG, YHB14112, YM974, Youfeline, Youfenac, Yuma, Yumerol, Yuroben, YY piroxicam, Z104657A, Zacy, Zaltokin, zaltoprofen, Zap70 Inhibitor, Zeepain, Zeloxim Fort, Zema-Pak, Zempack, Zempred, Zenapax, Zenas, Zenol, Zenos, Zenoxone, Zerax, Zerocam, Zerospasm, ZFNs, zinc oxide, Zipsor, ziralimumab, Zitis, Zix-S, Zocort, Zodixam, Zoftadex, zoledronic acid, Zolfin, Zolterol, Zopyrin, Zoralone, ZORprin, Zortress, ZP1848, zucapsaicin, Zunovate, Zwitterionic polysaccharides, ZY1400, Zybodies, Zycel, Zyrofen, Zyrogen Inhibitors, Zyser, Zytrim, and Zywin-Forte. In addition, the anti-inflammatory drugs, as listed above, may be combined with one or more agents listed above or herein or with other agents known in the art.

In some embodiments, a drug that reduces, inhibits, prevents and/or ameliorates inflammation, for example, one of the drugs provided above, is delivered to the suprachoroidal space of the eye using the kits, devices, and methods disclosed herein, and is used to treat, prevent and/or ameliorate a disease or disorder selected from arthritis, degenerative arthritis, psoriatic arthritis, arthritic disorders, arthritic pain, arthrosis, autoimmune arthritis, autoimmune diseases, autoimmune disorders, axial spondyloarthritis, chronic prosthetic joint infection, collagen induced arthritis, osteoarthritis, rheumatoid arthritis, senile arthritis, seronegative oligoarthritis of the knee, allergic and autoimmune inflammatory diseases, inflammatory diseases, inflammatory disorders, collagen diseases, discoid Lupus Erythematosus, immune deficiencies, immune diseases, immune disorders, immunodeficiency diseases, immunodeficiency disorders, immunoglobulin (IgG2) deficiency, immunoglobulin deficiency, Inflammation, Lambert-Eaton myasthenia syndrome, polymyositis, dermatomyositis, polyneuritis, post-operative ocular inflammation, polychondritis, sporadic inclusion body myositis, Systemic Lupus Erythematosus, T cell deficiency, TNF-receptor associated periodic syndrome, tropical spastic paraparesis, Wegener Granulomatosis, X-linked severe combined immunodeficiency disease, Behcet's disease, Crohn's disease, Crohn's Fistula, cutaneous Lupus Erythematosus, acute inflammation, acute inflammatory edema, adrenocortical insufficiency, cerebral inflammation, chronic lung inflammation, corticoid-responsive inflammatory skin disorders, cutaneous inflammation, dermal inflammation, dry skin inflammatory disease, ear edema, ear inflammation, glossitis, inflammatory bowel disease, inflammatory degenerative disease, inflammatory disorders of the eye and/or ear, inflammatory lesions in fungal infections, inflammatory lesions, inflammatory pain, inflammatory skin diseases or disorders, mouth and gum inflammation, mouth and throat inflammation, musculoskeletal disorders, otitis, pelvic inflammatory disease, perianal inflammation, post operative inflammation, pulmonary inflammation, rectal inflammation, refractory idiopathic inflammatory myopathies, seborrhoeic dermatitis, swelling, aphthous ulcerations, chronic polyarthritis, juvenile rheumatoid arthritis, rheumatic diseases, Sjogren's syndrome, opthalmic for Sjogren's syndrome, transplant rejection, acute allograft rejection, chronic graft rejection, graft versus host disease, humoral rejection in heart transplantation, humoral rejection in kidney transplantation, organ rejection in renal transplantation, solid organ transplant rejection, bronchiolitis obliterans after lung transplantation, rejection of bone marrow transplant, chronic lung transplant rejection, Corneal graft rejection, delayed graft function in kidney transplantation, heart transplant rejection, Homotransplantation rejection, immune rejection of hESC-derived therapeutic grafts, kidney transplant rejection, liver transplant rejection, lung transplant rejection, organ rejection, pancreatic islet transplantation rejection in type I diabetes, renal transplant rejection and xenograft rejection.

In some embodiments, the drug delivered to the suprachoroidal space using the kits, devices, and methods disclosed herein treats, prevents, and/or ameliorates macular degeneration (e.g., age related macular degeneration, dry age related macular degeneration, exudative age-related macular degeneration, geographic atrophy associated with age related macular degeneration, neovascular (wet) age-related macular degeneration, neovascular maculopathy and age related macular degeneration, occult with no classic choroidal neovascularization (CNV) in age-related macular degeneration, Stargardt's disease, Subfoveal wet Age-Related macular degeneration, and Vitreomacular Adhesion (VMA) associated with Neovascular Age Related macular degeneration). Examples of drugs that treat, prevent and/or ameliorate macular degeneration that can be used in conjunction with the devices and methods described herein include, but are not limited to: A0003, A36 peptide, AAV2-sFLT01, ACE041, ACU02, ACU3223, ACU4429, AdPEDF, aflibercept, AG13958, aganirsen, AGN150998, AGN745, AL39324, AL78898A, AL8309B, ALN-VEG01, alprostadil, AM1101, amyloid beta antibody, anecortave acetate, Anti-VEGFR-2 Alterase, Aptocine, APX003, ARC1905, ARC1905 with Lucentis, ATG3, ATP-binding cassette, sub-family A, member 4 gene, ATXS10, Avastin with Visudyne, AVT101, AVT2, bertilimumab, bevacizumab with verteporfin, bevasiranib sodium, bevasiranib sodium; with ranibizumab, brimonidine tartrate, BVA301, canakinumab, Cand5, Cand5 with Lucentis, CERE140, ciliary neurotrophic factor, CLT009, CNTO2476, collagen monoclonal antibody, complement component 5 aptamer (pegylated), complement component 5 aptamer (pegylated) with ranibizumab, complement component C3, complement factor B antibody, complement factor D antibody, copper oxide with lutein, vitamin C, vitamin E, and zinc oxide, dalantercept, DE109, dexamethasone with ranibizumab and verteporfin, disitertide, DNA damage inducible transcript 4 oligonucleotide, E10030, E10030 with Lucentis, EC400, eculizumab, EGP, EHT204, embryonic stem cells, human stem cells, endoglin monoclonal antibody, EphB4 RTK Inhibitor, EphB4 Soluble Receptor, ESBA1008, ETX6991, Evizon, Eyebar, EyePromise Five, Eyevi, Eylea, F200, FCFD4514S, fenretinide, fluocinolone acetonide, fluocinolone acetonide with ranibizumab, fms-related tyrosine kinase 1 oligonucleotide, fms-related tyrosine kinase 1 oligonucleotide with kinase insert domain receptor 169, fosbretabulin tromethamine, Gamunex, GEM220, GS101, GSK933776, HC31496, Human n-CoDeR, HYB676, IBI-20089 with Lucentis, iCo-008, Icon1, I-Gold, Ilaris, Iluvien, Iluvien with Lucentis, immunoglobulins, integrin alpha5betAlimmunoglobulin fragments, Integrin inhibitor, IRIS Lutein, I-Sense Ocushield, Isonep, isopropyl unoprostone, JPE1375, JSM6427, KH902, LentiVue, LFG316, LP590, LPO1010AM, Lucentis, Lucentis with Visudyne, Lutein ekstra, Lutein with myrtillus extract, Lutein with zeaxanthin, M200, M200 with Lucentis, Macugen, MC1101, MCT355, mecamylamine, Microplasmin, motexafin lutetium, MP0112, NADPH oxidase inhibitors, Neoretna, neurotrophin 4 gene, Nova21012, Nova21013, NT501, NT503, Nutri-Stulln, ocriplasmin, OcuXan, Oftan Macula, Optrin, ORA102 with Avastin, P144, P17, Palomid 529, PAN90806, Panzem, Panzem, PARP Inhibitors, pazopanib hydrochloride, pegaptanib sodium, PF4523655, PG11047, piribedil, platelet-derived growth factor beta polypeptide aptamer (pegylated), platelet-derived growth factor beta polypeptide aptamer (pegylated) with ranibizumab, PLG101, PMX20005, PMX53, POT4, PRS055, PTK787, ranibizumab, ranibizumab with triamcinolone acetonide, ranibizumabwith verteporfin, ranibizumab with volociximab, RD27, Rescula, Retaane, retinal pigment epithelial cells, RetinoStat, RG7417, RN6G, RT101, RTU007, SB267268, serpin peptidase inhibitor, clade F, member 1 gene, shark cartilage extract, Shef1, SIR1046, SIR1076, Sirna027, sirolimus, SMTD004, Snelvit, SOD Mimetics, Soliris, sonepcizumab, squalamine lactate, ST602, StarGen, T2TrpRS, TA106, talaporfin sodium, Tauroursodeoxycholic acid, TG100801, TM, TLCx99, TRC093, TRC105, triamcinolone acetonide with verteporfin, Trivastal Retard, TT30, Ursa, ursodiol, Vangiolux, VAR10200, vascular endothelial growth factor antibody, vascular endothelial growth factor B, vascular endothelial growth factor kinoid, vascular endothelial growth factor oligonucleotide, VAST Compounds, vatalanib, VEGF Inhibitor, verteporfin, Visudyne, Visudyne with Lucentis and dexamethasone, Visudyne with triamcinolone acetonide, Vivis, volociximab, Votrient, XV615, zeaxanthin, ZFP TF, zinc-monocysteine and Zybrestat. In one embodiment, one or more of the macular degeneration treating drugs described above is combined with one or more agents listed above or herein or with other agents known in the art.

In one embodiment, the kits, methods, and devices provided hererin are used to deliver triamcinolone or triamcinolone acetonide to the suprachoroidal space of an eye of a patient in need thereof. In a further embodiment, the triamcinolone or triamcinolone acetonide is delivered for the treatment of sympathetic ophthalmia, temporal arteritis, uveitis and/or ocular inflammatory conditions. In one embodiment, triamcinolone or triamcinolone acetonide is delivered to the suprachoroidal space of the eye in a patient in need of treatment of sympathetic opthalmia with the methods and devices described herein. In another embodiment, triamcinolone or triamcinolone acetonide is delivered to the suprachoroidal space of the eye in a patient in need of treatment of temporal arteritis with the methods and devices described herein. In yet another embodiment, triamcinolone or triamcinolone acetonide is delivered to the suprachoroidal space of the eye in a patient in need of treatment of uveitis, with the methods and devices described herein. In another embodiment, triamcinolone or triamcinolone acetonide is delivered to the suprachoroidal space of the eye in a patient in need of treatment of one or more ocular inflammatory conditions, with the methods and devices described herein.

The triamcinolone composition provided herein, in one embodiment, is a suspension comprising microparticles or nanoparticles of triamcinolone or triamcinolone acetonide. The microparticles, in one embodiment, have a D50 of about 3 µm or less. In a further embodiment, the D50 is about 2 µm. In another embodiment, the D50 is about 2 µm or less. In even another embodiment, the D50 is about 1000 nm or less. The microparticles, in one embodiment, have a D99 of about 10 µm or less. In another embodiment, the D99 is about 10 µm. In another embodiment, the D99 is less than about 10 µm or less than about 9 µm or less.

In one embodiment, the triamcinolone composition comprises triamcinolone microparticles. In a further embodiment, the composition comprises polysorbate 80. In another embodiment, the triamcinolone composition comprises one or more of CaCl2, MgCl2, sodium acetate and sodium citrate. In one embodiment, the composition comprises polysorbate 80 at a w/v % of 0.02% or about 0.02%, 0.015% or about 0.015%.

In certain embodiments the drug delivered to ocular tissues using the kits, devices, and methods disclosed herein treats, prevents, and/or ameliorates fibrosis (e.g. myelofibrosis, fibrosis in diabetic nephropathy, cystic fibrosis, scarring, and skin fibrosis).

In some embodiments, a drug that treats, prevents and/or ameliorates fibrosis is used in conjunction with the kits, devices, and methods described herein, and is delivered to the suprachoroidal space of the eye. In a further embodiment, the drug is Actimmune with Pirfenidone, ACUHTR028, AlphaVBeta5, aminobenzoate potassium, amyloid P, ANG1122, ANG1170, ANG3062, ANG3281, ANG3298, ANG4011, Anti-CTGF RNAi, Aplidin, *Astragalus membranaceus* extract with salvia and schisandra chinensis, atherosclerotic plaque blocker, Azol, AZX100, BB3, connective tissue growth factor antibody, CT140, danazol, Esbriet, EXC001, EXC002, EXC003, EXC004, EXC005, F647, FG3019, Fibrocorin, Follistatin, FT011, Galectin-3 inhibitors, GKT137831, GMCT01, GMCT02, GRMD01, GRMD02, GRN510, Heberon Alfa R, interferon alfa-2b, interferon gamma-1b with pirfenidone, ITMN520, JKB119, JKB121, JKB122, KRX168, LPAlreceptor antagonist, MGN4220, MIA2, microRNA 29a oligonucleotide, MMI0100, noscapine, PBI4050, PBI4419, PDGFR inhibitor, PF-06473871, PGN0052, Pirespa, Pirfenex, pirfenidone, plitidepsin, PRM151, Px102, PYN17, PYN22 with PYN17, Relivergen, rhPTX2 Fusion Proteins, RXI109, secretin, STX100, TGF-beta Inhibitor, transforming growth factor, beta receptor 2 oligonucleotide, VA999260 or XV615. In one embodiment, one or more of the fibrosis treating drugs described above is combined with one or more agents listed above or herein or with other agents known in the art.

In some embodiments, a drug that treats, prevents and/or ameliorates diabetic macular edema is used in conjunction with the kits, devices, and methods described herein, and is delivered to the suprachoroidal space of the eye. In a further embodiment, the drug is AKB9778, bevasiranib sodium, Candy5, choline fenofibrate, Cortiject, c-raf 2-methoxyethyl phosphorothioate oligonucleotide, DE109, dexamethasone, DNA damage inducible transcript 4 oligonucleotide, FOV2304, iCo007, KH902, MP0112, NCX434, Optina, Ozurdex, PF4523655, SAR1118, sirolimus, SK0503 or Tri-Lipix. In one embodiment, one or more of the diabetic macular edema treating drugs described above is combined with one or more agents listed above or herein or with other agents known in the art.

In some embodiments, a drug that treats, prevents and/or ameliorates macular edema is used in conjunction with the kits, devices, and methods described herein, and is delivered to the suprachoroidal space of the eye. In a further embodiment, the drug is denufosol tetrasodium, dexamethasone, ecallantide, pegaptanib sodium, ranibizumab or triamcinolone. In addition, the drugs delivered to ocular tissues using the devices and methods disclosed herein which treat, prevent, and/or ameliorate macular edema, as listed above, may be combined with one or more agents listed above or herein or with other agents known in the art.

In some embodiments, a drug that treats, prevents and/or ameliorates ocular hypertension is used in conjunction with the kits, devices, and methods described herein and is delivered to the suprachoroidal space of the eye. In a further embodiment, the drug is 2-MeS-beta gamma-CC12-ATP, Aceta Diazol, acetazolamide, Aristomol, Arteoptic, AZD4017, Betalmic, betaxolol hydrochloride, Betimol, Betoptic S, Brimodin, Brimonal, brimonidine, brimonidine tartrate, Brinidin, Calte, carteolol hydrochloride, Cosopt, CS088, DE092, DE104, DE111, dorzolamide, dorzolamide hydrochloride, Dorzolamide hydrochloride with Timolol maleate, Droptimol, Fortinol, Glaumol, Hypadil, Ismotic, isopropyl unoprostone, isosorbide, Latalux, latanoprost, Latanoprost with Timolol maleate, levobunolol hydrochloride, Lotensin, Mannigen, mannitol, metipranolol, mifepristone, Mikelan, Minims Metipranolol, Mirol, nipradilol, Nor Tenz, Ocupress, olmesartan, Ophtalol, pilocarpine nitrate, Piobaj, Rescula, RU486, Rysmon TG, SAD448, Saflutan, Shemol, Taflotan, tafluprost, tafluprost with timolol, Thiaboot, Timocomod, timolol, Timolol Actavis, timolol hemihydrate, timolol maleate, Travast, travoprost, Unilat, Xalacom, Xalatan or Zomilol. In addition, the drugs delivered to ocular tissues using the devices and methods disclosed herein which treat, prevent, and/or ameliorate ocular hypertension, as listed above, may be combined with one or more agents listed above or herein or with other agents known in the art.

In one embodiment, a drug that inhibits angiogenesis is used in conjunction with the kits, devices, and methods described herein and is delivered to the suprachoroidal space of the eye and/or the subretinal space of the eye. In some embodiments, the angiogenesis inhibitor is an antagonist of a member of the platelet derived growth factor (PDGF) family, for example, a drug that inhibits, reduces or modulates the signaling and/or activity of PDGF-receptors (PDGFR). For example, the PDGF antagonist delivered to the suprachoroidal space for the treatment of a choroidal malady, in one embodiment, is an anti-PDGF aptamer, an anti-PDGF antibody or fragment thereof, an anti-PDGFR antibody or fragment thereof, or a small molecule antagonist. In one embodiment, the PDGF antagonist is an antagonist of the PDGFR-α or PDGFR-β. In one embodiment, the PDGF antagonist is the anti-PDGF-β aptamer E10030, sunitinib, axitinib, sorefenib, imatinib, imatinib mesylate, nintedanib, pazopanib HCl, ponatinib, MK-2461, dovitinib, pazopanib, crenolanib, PP-121, telatinib, imatinib, KRN 633, CP 673451, TSU-68, Ki8751, amuvatinib, tivozanib, masitinib, motesanib diphosphate, dovitinib dilactic acid, linifanib (ABT-869).

In certain embodiments one or more drugs may be delivered to ocular tissues and/or into the suprachoroidal space via the systems and devices described herein. Delivery of one or more drugs into the suprachoroidal space using the device described herein may be accomplished by using one or more devices, delivery members or the like. In addition, combinations of one of more drugs may be delivered to the suprachoroidal space using the device described herein in combination with delivery of one or more drugs via intravitreal (IVT) administration (e.g., intravitreal injection, intravitreal implant or eye drops). Methods of IVT administration are well known in the art. Examples of drugs that can be administered via IVT include, but are not limited to: A0003, A0006, Acedolone, AdPEDF, aflibercept, AG13958, aganirsen, AGN208397, AKB9778, AL78898A, amyloid P, Angiogenesis Inhibitor Gene Therapy, ARC1905, Aurocort, bevasiranib sodium, brimonidine, Brimonidine, brimonidine tartrate, bromfenac sodium, Candy5, CERE140, Ciganclor, CLT001, CLT003, CLT004, CLT005, complement component 5 aptamer (pegylated), complement factor D antibody, Cortiject, c-raf 2-methoxyethyl phosphorothioate oligonucleotide, cyclosporine, triamcinolone, DE109, denufosol tetrasodium, dexamethasone, dexamethasone phosphate, disitertide, DNA damage inducible transcript 4 oligonucleotide, E10030, ecallantide, EG3306, Eos013, ESBA1008, ESBA105, Eylea, FCFD4514S, fluocinolone acetonide, fms-related tyrosine kinase 1 oligonucleotide, fomivirsen sodium, fosbretabulin tromethamine, FOV2301, FOV2501, ganciclovir, ganciclovir sodium, GS101, GS156, hyaluronidase, IBI20089, iCo007, Iluvien, INS37217, Isonep, JSM6427, Kalbitor, KH902, lerdelimumab, LFG316, Lucentis, M200, Macugen, Makyueido, Microplasmin, MK0140, MP0112, NCX434, neurotrophin 4 gene, OC10X, ocriplasmin, ORA102, Ozurdex, P144, P17, Palomid 529, pazopanib hydrochloride, pegaptanib sodium, Plasma Kallikrein Inhibitors, platelet-derived growth factor beta polypeptide aptamer (pegylated), POT4, PRM167, PRS055, QPI1007, ranibizumab, resveratrol, Retilone, retinal pigment epithelium-specific protein 65 kDa gene, Retisert, rod derived cone viability factor, RPE65 Gene Therapy, RPGR Gene Therapy, RTP801, Sd-rxRNA, serpin peptidase inhibitor clade F member 1 gene, Sirna027, sirolimus, sonepcizumab, SRT501, STP601, TG100948, Trabio, triamcinolone, triamcinolone acetonide, Trivaris, tumor necrosis factor antibody, VEGF/rGel-Op, verteporfin, Visudyne, Vitrase, Vitrasert, Vitravene, Vitreals, volociximab, Votrient, XG102, Xibrom, XV615, and Zybrestat. Accordingly, the methods of the present invention include administrating via IVT one or more of the drugs listed above in combination with one or more drugs disclosed herein administered into the suprachoroidal space using the device described herein.

In some embodiments, the drug is formulated for storage and delivery via the kits, devices, and methods described herein. The "drug formulation" is a formulation of a drug, which typically includes one or more pharmaceutically acceptable excipient materials known in the art. The term "excipient" refers to any non-active ingredient of the formulation intended to facilitate handling, stability, dispersibility, wettability, release kinetics, and/or injection of the drug. In one embodiment, the excipient may include or consist of water or saline.

In some embodiments, the fluid drug formulation includes microparticles or nanoparticles, each of which can include at least one drug. Desirably, the microparticles or nanoparticles provide for the controlled release of drug into the ocular tissue. As used herein, the term "microparticle" encompasses microspheres, microcapsules, microparticles, and beads, having a number average diameter of 1 to 100 µm, most preferably 1 to 25 µm. The term "nanoparticles" are particles having a number average diameter of 1 to 1000 nm. Microparticles may or may not be spherical in shape. "Microcapsules" are defined as microparticles having an outer shell surrounding a core of another material. The core can be liquid, gel, solid, gas, or a combination thereof. In one case, the microcapsule may be a "microbubble" having an outer shell surrounding a core of gas, wherein the drug is disposed on the surface of the outer shell, in the outer shell itself, or in the core. Microbubbles may respond to acoustic vibrations as known in the art for diagnosis and/or can be used to burst the microbubble to release its payload at/into a select ocular tissue site. "Microspheres" can be solid spheres, can be porous and include a sponge-like or honeycomb structure formed by pores or voids in a matrix material or shell, or can include multiple discrete voids in a matrix material or shell. The microparticle or nanoparticles may further include a matrix material. The shell or matrix material may be a polymer, amino acid, saccharride, or other material known in the art of microencapsulation.

The drug-containing microparticles or nanoparticles may be suspended in an aqueous or non-aqueous liquid vehicle. The liquid vehicle may be a pharmaceutically acceptable aqueous solution, and optionally may further include a surfactant. The microparticles or nanoparticles of drug themselves may include an excipient material, such as a polymer, a polysaccharide, a surfactant, etc., which are known in the art to control the kinetics of drug release from particles.

In one embodiment, the fluid drug formulation further includes an agent effective to degrade collagen or GAG fibers in the sclera, which may enhance penetration/release of the drug into the ocular tissues. This agent may be, for example, an enzyme, such a hyaluronidase, a collagenase, or a combination thereof. In a variation of this method, the enzyme is administered to the ocular tissue in a separate step from—preceding or following—infusion of the drug. The enzyme and drug are administered at the same site.

In another embodiment, the drug formulation is one that undergoes a phase change upon administration. For instance, a liquid drug formulation may be injected through hollow microneedles into the suprachoroidal space, where it then gels and the drug diffuses out from the gel for controlled release.

While the embodiments and methods herein describe delivering a medicament to a target tissue, the embodiments described herein can be configured to facilitate removal of a substance from a target location.

While the embodiments have been described above in use on ocular tissue, in some instances, the embodiments and methods described herein can be used on any other suitable bodily tissue. For example, in some instances, the use of an adjustable length needle can be beneficial in conjunction with standard phlebotomy techniques during drug infusion and/or blood draw from a vein. Thus, while the embodiments and methods are specifically described above in use on ocular tissue, it should be understood that the embodiments and methods have been presented by way of example only, and not limitation Although various embodiments have been described as having particular features and/or combinations of components, other embodiments are possible having a combination of any features and/or components from any of embodiments where appropriate. For example, although the device 2000 is shown and described as including an energy source configured to produce a delivery pathway in other embodiments, the device 2000 can also include an energy source configured to facilitate transportation of the medicament after the initial delivery, as described in connection with the device 4000. As a further example, any of the embodiments shown and described herein can include a controller similar to the controller described above in connection with the devices shown in FIGS. 14-16 (e.g., delivery device 1000), 29, and 38-40. For example, in some embodiments, the medicament delivery device 7000 can include a controller configured to control and/or adjust the energy source to facilitate conveyance of the drug from the vitreous into the SCS and/or the SRS.

In some embodiments, a kit can include multiple medicament containers, delivery devices, or the like.

The invention claimed is:
1. An apparatus, comprising:
a housing having a distal end portion configured to contact a surface of an eye, the housing defining a reservoir configured to contain a medicament having an ionic charge, the reservoir having walls with a charge opposite a charge of the medicament such that the reservoir is configured to hold the medicament in the reservoir;

a puncture member fluidically coupled to the reservoir and configured to be inserted into and deliver the medicament to a target region within the eye;

an electrode operably coupled to the medicament disposed within the reservoir, the electrode configured to produce a charge sufficient to convey the medicament from the reservoir to a distal end of the puncture member within the target region within the eye, a controller configured to send a signal to the electrode to adjust the charge such that the medicament is conveyed from the reservoir; and a sensor, the sensor configured to detect at least one of the charge of the electrode, a level of the medicament within the reservoir, or an indication of delivery depth of the medicament.

2. The apparatus of claim 1, wherein the medicament delivery depth is within a predetermined range.

3. The apparatus of claim 2, wherein the predetermined range is between about 900 μm and about 1100 μm.

4. The apparatus of claim 1, further comprising:
a contact member coupled to the distal end portion of the housing and configured to move an outer portion of the eye to define a first pathway through which the distal end portion of the housing can be disposed, the electrode being configured to produce the charge sufficient to convey the medicament from the reservoir to the targeted region through a second pathway below the first pathway and the outer portion of the eye.

5. The apparatus of claim 1, wherein the reservoir contains the electrode.

6. The apparatus of claim 1, wherein the medicament is encapsulated in a carrier that is disposed within the reservoir, the carrier having an ionic charge.

7. The apparatus of claim 1, wherein an inner wall of the reservoir has an ionic charge that is opposite the ionic charge of the medicament.

8. The apparatus of claim 1, wherein the controller is configured to change an ionic charge of the reservoir to match the ionic charge of the medicament such that the medicament is repelled out of the reservoir.

9. The apparatus of claim 1, wherein the distal end portion of the housing defines a channel in fluid communication with the reservoir, inner walls of the channel define an opening, the apparatus further comprising:
a membrane covering the opening and having an ionic charge such that when the ionic charge of the membrane is similar to the ionic charge of the medicament, the membrane limits the medicament from passing therethrough, and when the ionic charge of the membrane is different from the ionic charge of the medicament, the medicament can pass therethrough, the electrode configured to produce the ionic charge of the membrane.

10. The apparatus of claim 1, further comprising a contact member movably coupled to the distal end portion of the housing, the contact member configured to move an outer portion of the eye to define a first pathway through which the distal end portion of the housing can be disposed.

11. The apparatus of claim 1, wherein the charge is sufficient to convey the medicament from the reservoir to a delivery depth within a predetermined range in the eye, the delivery depth dependent on an intensity of the charge.

12. An apparatus, comprising:
a housing having a distal end portion configured to contact a surface of an eye, the housing defining a reservoir configured to contain a medicament having an ionic charge, the reservoir having walls with a charge opposite a charge of the medicament such that the reservoir is configured to hold the medicament in the reservoir;

a puncture member defining a lumen, the puncture member fluidically coupled to the reservoir and configured to deliver the medicament to a target region within the eye;

an electrode operably coupled to the medicament disposed within the reservoir, the electrode configured to produce a charge sufficient to convey the medicament from the reservoir to a distal end of the puncture member within the target region within the eye through the lumen below an outer portion of the eye;

a controller configured to send a signal to the electrode to adjust the charge such that the medicament is conveyed from the reservoir; and a sensor, the sensor configured to detect at least one of the charge of the electrode, a level of the medicament within the reservoir, or an indication of delivery depth of the medicament.

13. The apparatus of claim 12, wherein the controller is configured to send a signal to the electrode to convey the medicament to a medicament delivery depth within a predetermined range between about 900 μm and about 1100 μm.

14. The apparatus of claim 12, wherein an inner wall of the reservoir has an ionic charge that is opposite the ionic charge of the medicament.

15. The apparatus of claim 12, wherein the distal end portion of the housing defines a channel in fluid communication with the reservoir, inner walls of the channel define an opening through which the medicament can be conveyed to the target region, the apparatus further comprising:
a membrane covering the opening and having an ionic charge such that when the ionic charge of the membrane is similar to the ionic charge of the medicament, the membrane limits the medicament from passing therethrough, and when the ionic charge of the membrane is different from the ionic charge of the medicament, the medicament can pass therethrough, the electrode configured to produce the ionic charge of the membrane.

16. The apparatus of claim 12, wherein the charge is sufficient to convey the medicament from the reservoir to a delivery depth within a predetermined range in the eye, the delivery depth dependent on an intensity of the charge.

17. The apparatus of claim 12, further comprising:
a contact member coupled to the housing, the contact member configured to move an outer portion of the eye to define a pathway through which the distal end portion of the housing is disposed.

18. The apparatus of claim 17, wherein the contact member is movably coupled to the housing between a first position in which the contact member is configured to initiate contact with the outer portion of the eye and a second position in which the contact member has moved the outer portion of the eye to define the pathway.

19. The apparatus of claim 17, wherein the contact member includes at least one of a sharp edge or blade configured to at least one of cut or move the outer portion of the eye to define the pathway.

20. The apparatus of claim 12, wherein the outer portion of the eye includes a conjunctiva.

21. An apparatus, comprising:
a housing having a distal end portion configured to contact a surface of an eye, the housing defining a reservoir configured to contain a medicament having an ionic charge, the reservoir having walls with a charge opposite a charge of the medicament such that the reservoir is configured to hold the medicament in the reservoir;
a puncture member defining a lumen, the puncture member fluidically coupled to the reservoir and configured to deliver the medicament to a target region within the eye;
an electrode coupled to the medicament disposed within the reservoir, the electrode configured to produce a charge sufficient to convey the medicament from the reservoir to a distal end of the puncture member at a delivery depth within a predetermined range in the eye, the delivery depth dependent on an intensity of the charge;
a controller configured to adjust the charge to convey the medicament to the predetermined delivery depth; and
a sensor, the sensor configured to detect at least one of a position of the distal end portion of the housing, a level of the medicament within the reservoir, or an indication of delivery depth of the medicament.

22. The apparatus of claim 21, wherein the predetermined range is between about 900 µm and about 1100 µm.

23. The apparatus of claim 21, further comprising:
a contact member coupled to the distal end portion of the housing and configured to cut an outer portion of the eye to define a first pathway through which the distal end portion of the housing can be disposed, the electrode configured to produce the charge sufficient to convey the medicament from the reservoir to a targeted region through a second pathway below the outer portion of the eye.

24. The apparatus of claim 21, wherein the medicament is encapsulated in a carrier that is disposed within the reservoir, the carrier having an ionic charge.

25. The apparatus of claim 21, wherein the distal end portion of the housing defines a channel in fluid communication with the reservoir, inner walls of the channel define an opening through which the medicament can be conveyed to a targeted region, the apparatus further comprising:
a membrane covering the opening and having an ionic charge such that when the ionic charge of the membrane is similar to the ionic charge of the medicament, the membrane limits the medicament from passing therethrough, and when the ionic charge of the membrane is different from the ionic charge of the medicament, the medicament can pass therethrough,
the electrode configured to produce the ionic charge of the membrane.

26. The apparatus of claim 21, further comprising:
a puncture member fluidically coupled to the reservoir and configured to deliver the medicament to the delivery depth within the predetermined range in the eye.

27. The apparatus of claim 21, wherein the predetermined range in the eye includes the suprachoroidal space of the eye.

28. An apparatus, comprising:
a housing having a distal end portion configured to contact a surface of an eye, the housing defining a reservoir configured to contain a medicament having an ionic charge, the reservoir having walls with a charge opposite a charge of the medicament such that the reservoir is configured to hold the medicament in the reservoir; the reservoir having walls with a charge opposite a charge of the medicament such that the reservoir is configured to hold the medicament in the reservoir;
a puncture member defining a lumen, the puncture member fluidically coupled to the reservoir and configured to deliver the medicament to a target region within the eye; and
an electrode operably coupled to the medicament disposed within the reservoir, the electrode configured to produce a charge sufficient to convey the medicament from the reservoir to a distal end of the puncture member at a delivery depth within a predetermined range in the eye, the delivery depth dependent on an intensity of the charge,
wherein the distal end portion of the housing defines a channel in fluid communication with the reservoir, inner walls of the channel define an opening through which the medicament can be conveyed to a targeted region, the apparatus further comprising:
a membrane covering the opening and having an ionic charge such that when the ionic charge of the membrane is similar to the ionic charge of the medicament, the membrane limits the medicament from passing therethrough, and when the ionic charge of the membrane is different from the ionic charge of the medicament, the medicament can pass therethrough,
the electrode configured to produce the ionic charge of the membrane.

29. The apparatus of claim 28, further comprising:
a puncture member defining a pathway, the puncture member fluidically coupleable to the reservoir and configured to deliver the medicament to the targeted region within the eye.

30. The apparatus of claim 28, wherein the predetermined range in the eye includes the suprachoroidal space of the eye.

31. An apparatus, comprising:
a housing having a distal end portion configured to contact a surface of an eye, the housing defining a reservoir configured to contain a medicament having an ionic charge;
an electrode coupled to the housing, the electrode configured to produce a charge sufficient to convey the medicament from the reservoir to a delivery depth within a predetermined range in the eye, the delivery depth dependent on an intensity of the charge; and a controller configured to adjust the charge to convey the medicament to the medicament delivery depth within the predetermined range;
a puncture member defining a pathway, the puncture member fluidically coupleable to the reservoir and configured to deliver the medicament to a targeted region within the eye; and
a contact member fixedly coupled to the housing, the contact member configured to move relative to the housing from a vertical orientation to a horizontal orientation to move an outer portion of the eye to define a pathway through which a distal end portion of the puncture member can be disposed,
the distal end portion of the housing defining a channel in fluid communication with the reservoir, inner walls of the channel defining an opening through which the medicament can be conveyed to the targeted region; and
a membrane covering the opening and having an ionic charge such that when the ionic charge of the membrane is similar to the ionic charge of the medicament, the membrane limits the medicament from passing therethrough, and when the ionic charge of the membrane is different from the ionic charge of the medicament, the medicament can pass therethrough, the electrode configured to produce the ionic charge of the membrane.

32. The apparatus of claim 31, wherein the predetermined range in the eye includes the subretinal space of the eye.

\* \* \* \* \*